United States Patent [19]

Bolin et al.

[11] Patent Number: 5,677,419
[45] Date of Patent: Oct. 14, 1997

[54] CYCLIC VASOACTIVE PEPTIDE ANALOGS

[75] Inventors: David Robert Bolin, Montclair; Margaret O'Donnell, Clifton, both of N.J.

[73] Assignee: Hoffmann-La Roche Inc., Nutley, N.J.

[21] Appl. No.: 308,729

[22] Filed: Sep. 19, 1994

Related U.S. Application Data

[63] Continuation of Ser. No. 153,530, Nov. 16, 1993, abandoned, which is a continuation of Ser. No. 773,747, Oct. 11, 1991, abandoned.

[51] Int. Cl.$^6$ ..................................................... C07K 7/60
[52] U.S. Cl. ...................... 530/317; 530/318; 530/324; 930/170; 930/270; 930/DIG. 546; 930/DIG. 548
[58] Field of Search ...................... 530/317, 318, 530/324; 930/170, 270, DIG. 546, DIG. 548

[56] References Cited

U.S. PATENT DOCUMENTS

| | | | |
|---|---|---|---|
| 4,737,487 | 4/1988 | Watts et al. | 514/15 |
| 4,835,252 | 5/1989 | Musso et al. | 530/324 |
| 5,084,442 | 1/1992 | Felix et al. | 530/317 |
| 5,141,924 | 8/1992 | Bolin | 530/324 |

FOREIGN PATENT DOCUMENTS

| | | |
|---|---|---|
| 325044 | 7/1989 | European Pat. Off. . |
| 405242 | 2/1991 | European Pat. Off. . |

OTHER PUBLICATIONS

Hornby, Life Sciences, vol. 31, pp. 189–199, (1982).
Felix et al, "Synthesis and biological activity of novel linear and cyclic GRF analogs", pp. 1–4.
Robberecht et al, Eur. J. Bio Chem., vol. 159, pp. 45–49, (1986).
Musso et al, Biochemistry, vol. 27, pp. 8174–8181, (1988).
Tachibana et al, Peptide Chemistry, pp. 481–486, (1987).
Felix, et al. Int. J. Peptide Protein Res. 31 pp. 231–238 (1988).
Smith et al. Int. J. Peptide Res. 21, pp. 127–134 (1983).
Smith, et al. Journal of Medicinal Chemistry, vol. 21 No. 1 pp. 117–120 (1978).
Chipens, et al., Int. J. Peptide Res. 18, pp. 302–311 (1981).
DiMaio, et al., J. Med. Chem. 25, pp. 1432–1438 (1982).

*Primary Examiner*—Christina Y. Chan
*Assistant Examiner*—T. D. Wessendorf
*Attorney, Agent, or Firm*—George W. Johnston; Dennis P. Tramaloni; Bruce A. Pokras

[57] ABSTRACT

Analogs of porcine Vasoactive Intestinal Peptide are disclosed. The analogs have been cyclized by the covalent attachment, via an amide bond, of the side-chain carboxy terminus of one amino acid in the peptide chain to the side-chain amino terminus of another amino acid in the peptide chain. The claimed compounds are useful for the treatment of asthma.

32 Claims, No Drawings

SEQUENCE LISTING ( 1 ) GENERAL INFORMATION:

( i i i ) NUMBER OF SEQUENCES: 73

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Sus scrofa ( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:1: FROM 18 TO 23

( x i ) SEQUENCE DESCRIPTION: SEQ ID NO:1:

```
His Ser Asp Ala Val Phe Thr Asp Asn Tyr Thr Arg Leu Arg Lys Gln
 1               5                  10                      15

Met Ala Val Lys Lys Tyr Leu Asn Ser Ile Leu Asn
             20                  25
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 8..12
        ( D ) OTHER INFORMATION: /note="Side chains of amino acids
            8 and 12 reacted to form cyclic structure"

( i x ) FEATURE:
        ( A ) NAME/KEY: Modified-site
        ( B ) LOCATION: 8
        ( D ) OTHER INFORMATION: /note="Xaa=Asp, Glu or Lys"

( i x ) FEATURE:
        ( A ) NAME/KEY: Modified-site
        ( B ) LOCATION: 12
        ( D ) OTHER INFORMATION: /note="Xaa=Arg, Lys, Orn or Asp"

( i x ) FEATURE:
        ( A ) NAME/KEY: Modified-site
        ( B ) LOCATION: 17
        ( D ) OTHER INFORMATION: /note="Xaa=Met or Nle"

( i x ) FEATURE:
        ( A ) NAME/KEY: Modified-site
        ( B ) LOCATION: 26
        ( D ) OTHER INFORMATION: /note="Xaa=Ile or Val"

( i x ) FEATURE:
        ( A ) NAME/KEY: Modified-site
        ( B ) LOCATION: 28
        ( D ) OTHER INFORMATION: /note="Xaa=Asn or Thr"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:2: FROM 18 TO 23

( x i ) SEQUENCE DESCRIPTION: SEQ ID NO:2:

His Ser Asp Ala Val Phe Thr Xaa Asn Tyr Thr Xaa Leu Arg Lys Gln
1               5                   10                  15

Xaa Ala Val Lys Lys Tyr Leu Asp Ser Xaa Leu Xaa
            20                  25

( 2 ) INFORMATION FOR SEQ ID NO:3:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 8..12
        ( D ) OTHER INFORMATION: /note="Side-chains of amino acids
            8 and 12 reacted to form cyclic structure"

( i x ) FEATURE:
    ( A ) NAME/KEY: Modified-site
    ( B ) LOCATION: 8
    ( D ) OTHER INFORMATION: /note="Xaa=Asp, Glu or Lys"

( i x ) FEATURE:
    ( A ) NAME/KEY: Modified-site
    ( B ) LOCATION: 12
    ( D ) OTHER INFORMATION: /note="Xaa=Arg, Lys, Orn or Asp"

( i x ) FEATURE:
    ( A ) NAME/KEY: Modified-site
    ( B ) LOCATION: 17
    ( D ) OTHER INFORMATION: /note="Xaa=Nle"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:3: FROM 18 TO 23

( x i ) SEQUENCE DESCRIPTION: SEQ ID NO:3:

```
His Ser Asp Ala Val Phe Thr Xaa Asn Tyr Thr Xaa Leu Arg Lys Gln
1               5                   10                  15

Xaa Ala Val Lys Lys Tyr Leu Asp Ser Val Leu Thr
            20                  25
```

( 2 ) INFORMATION FOR SEQ ID NO:4:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 9..12
        ( D ) OTHER INFORMATION: /note="Side-chains of amino acids
            9 and 12 reacted to form cyclic structure"

( i x ) FEATURE:
        ( A ) NAME/KEY: Modified-site
        ( B ) LOCATION: 8
        ( D ) OTHER INFORMATION: /note="Xaa=Asp or Asn"

( i x ) FEATURE:
        ( A ) NAME/KEY: Modified-site
        ( B ) LOCATION: 17
        ( D ) OTHER INFORMATION: /note="Xaa=Met or Nle"

( i x ) FEATURE:
        ( A ) NAME/KEY: Modified-site
        ( B ) LOCATION: 26
        ( D ) OTHER INFORMATION: /note="Xaa=Ile or Val"

( i x ) FEATURE:
        ( A ) NAME/KEY: Modified-site
        ( B ) LOCATION: 28
        ( D ) OTHER INFORMATION: /note="Xaa=Asn or Thr"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:4: FROM 18 TO 23

( x i ) SEQUENCE DESCRIPTION: SEQ ID NO:4:

```
His Ser Asp Ala Val Phe Thr Xaa Asn Tyr Thr Lys Leu Arg Lys Gln
1               5                   10                  15
```

```
Xaa  Ala  Val  Lys  Lys  Tyr  Leu  Asp  Ser  Xaa  Leu  Xaa
          20                         25
```

( 2 ) INFORMATION FOR SEQ ID NO:5:

( i ) SEQUENCE CHARACTERISTICS:
    ( A ) LENGTH: 28 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 9..12
    ( D ) OTHER INFORMATION: /note="Side chains of amino acids
      9 and 12 reacted to form cyclic structure"

( i x ) FEATURE:
    ( A ) NAME/KEY: Modified-site
    ( B ) LOCATION: 17
    ( D ) OTHER INFORMATION: /note="Xaa=Nle"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:5: FROM 18 TO 23

( x i ) SEQUENCE DESCRIPTION: SEQ ID NO:5:

```
His  Ser  Asp  Ala  Val  Phe  Thr  Asn  Asp  Tyr  Thr  Lys  Leu  Arg  Lys  Gln
1                   5                        10                        15

Xaa  Ala  Val  Lys  Lys  Tyr  Leu  Asp  Ser  Val  Leu  Thr
          20                         25
```

( 2 ) INFORMATION FOR SEQ ID NO:6:

( i ) SEQUENCE CHARACTERISTICS:
    ( A ) LENGTH: 28 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 12..16
    ( D ) OTHER INFORMATION: /note="Side-chains of amino acids
      12 and 16 reacted to form cyclic structure"

( i x ) FEATURE:
    ( A ) NAME/KEY: Modified-site
    ( B ) LOCATION: 17
    ( D ) OTHER INFORMATION: /note="Xaa=Met or Nle"

( i x ) FEATURE:
    ( A ) NAME/KEY: Modified-site
    ( B ) LOCATION: 26
    ( D ) OTHER INFORMATION: /note="Xaa=Ile or Val"

( i x ) FEATURE:
    ( A ) NAME/KEY: Modified-site
    ( B ) LOCATION: 28
    ( D ) OTHER INFORMATION: /note="Xaa=Asn or Thr"

( x ) PUBLICATION INFORMATION:
    ( H ) DOCUMENT NUMBER: EP 325 044 A A
    ( I ) FILING DATE: 22-DEC-1987

(J) PUBLICATION DATE: 26-JUL-1989
(K) RELEVANT RESIDUES IN SEQ ID NO:6: FROM 18 TO 23

(xi) SEQUENCE DESCRIPTION: SEQ ID NO:6:

```
His Ser Asp Ala Val Phe Thr Asp Asn Tyr Thr Lys Leu Arg Lys Glu
 1               5                  10                      15
Xaa Ala Val Lys Lys Tyr Leu Asp Ser Xaa Leu Xaa
             20                  25
```

(2) INFORMATION FOR SEQ ID NO:7:

(i) SEQUENCE CHARACTERISTICS:
        (A) LENGTH: 28 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 12..16
        (D) OTHER INFORMATION: /note="Side-chains of amino acids
            12 and 16 reacted to form cyclic structure"

(ix) FEATURE:
        (A) NAME/KEY: Modified-site
        (B) LOCATION: 17
        (D) OTHER INFORMATION: /note="Xaa=Nle"

(x) PUBLICATION INFORMATION:
        (H) DOCUMENT NUMBER: EP 325 044 A A
        (I) FILING DATE: 22-DEC-1987
        (J) PUBLICATION DATE: 26-JUL-1989
        (K) RELEVANT RESIDUES IN SEQ ID NO:7: FROM 18 TO 23

(xi) SEQUENCE DESCRIPTION: SEQ ID NO:7:

```
His Ser Asp Ala Val Phe Thr Asp Asn Tyr Thr Lys Leu Arg Lys Glu
 1               5                  10                      15
Xaa Ala Val Lys Lys Tyr Leu Asp Ser Val Leu Thr
             20                  25
```

(2) INFORMATION FOR SEQ ID NO:8:

(i) SEQUENCE CHARACTERISTICS:
        (A) LENGTH: 28 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 20..24
        (D) OTHER INFORMATION: /note="Side-chains of amino acids
            20 and 24 reacted to form cyclic structure"

(ix) FEATURE:
        (A) NAME/KEY: Modified-site
        (B) LOCATION: 12
        (D) OTHER INFORMATION: /note="Xaa=Arg or Lys"

(ix) FEATURE:
        (A) NAME/KEY: Modified-site
        (B) LOCATION: 17
        (D) OTHER INFORMATION: /note="Xaa=Met or Nle"

( i x ) FEATURE:
  ( A ) NAME/KEY: Modified-site
  ( B ) LOCATION: 26
  ( D ) OTHER INFORMATION: /note="Xaa=Ile or Val"

( i x ) FEATURE:
  ( A ) NAME/KEY: Modified-site
  ( B ) LOCATION: 28
  ( D ) OTHER INFORMATION: /note="Xaa=Asn or Thr"

( x ) PUBLICATION INFORMATION:
  ( H ) DOCUMENT NUMBER: EP 325 044 A A
  ( I ) FILING DATE: 22-DEC-1987
  ( J ) PUBLICATION DATE: 26-JUL-1989
  ( K ) RELEVANT RESIDUES IN SEQ ID NO:8: FROM 18 TO 23

( x i ) SEQUENCE DESCRIPTION: SEQ ID NO:8:

```
His Ser Asp Ala Val Phe Thr Asp Asn Tyr Thr Xaa Leu Arg Lys Gln
1               5                   10                  15
Xaa Ala Val Lys Lys Tyr Leu Asp Ser Xaa Leu Xaa
                20                  25
```

( 2 ) INFORMATION FOR SEQ ID NO:9:

( i ) SEQUENCE CHARACTERISTICS:
    ( A ) LENGTH: 28 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 20..24
    ( D ) OTHER INFORMATION: /note="Side-chains of amino acids 20 and 24 reacted to form cyclic structure"

( i x ) FEATURE:
    ( A ) NAME/KEY: Modified-site
    ( B ) LOCATION: 17
    ( D ) OTHER INFORMATION: /note="Xaa=Nle"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:9: FROM 18 TO 23

( x i ) SEQUENCE DESCRIPTION: SEQ ID NO:9:

```
His Ser Asp Ala Val Phe Thr Asp Asn Tyr Thr Lys Leu Arg Lys Gln
1               5                   10                  15
Xaa Ala Val Lys Lys Tyr Leu Asp Ser Val Leu Thr
                20                  25
```

( 2 ) INFORMATION FOR SEQ ID NO:10:

( i ) SEQUENCE CHARACTERISTICS:
    ( A ) LENGTH: 28 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 21..25

( D ) OTHER INFORMATION: /note="Side-chains of amino acids
21 and 25 reacted to form cyclic structure"

( i x ) FEATURE:
 ( A ) NAME/KEY: Modified-site
 ( B ) LOCATION: 1
 ( D ) OTHER INFORMATION: /note="Xaa=His or N-methyl-Ala"

( i x ) FEATURE:
 ( A ) NAME/KEY: Modified-site
 ( B ) LOCATION: 6
 ( D ) OTHER INFORMATION: /note="Xaa=an amino acid in
which the side-chain is methylcyclohexyl, methylphenyl or
ethylphenyl wherein the phenyl ring is substituted with
X1 and X2 independently selected from H, OH, OCH3, F, Cl,
I, CH3, CF3, NO2, N(CH3)2, NHCOCH3, NHCOC6H5, or C(CH3)3,
or methylnapthalene ( i x ) FEATURE:
 ( A ) NAME/KEY: Modified-site
 ( B ) LOCATION: 2
 ( D ) OTHER INFORMATION: /note="Xaa=Ser or Ala"

( i x ) FEATURE:
 ( A ) NAME/KEY: Modified-site
 ( B ) LOCATION: 8
 ( D ) OTHER INFORMATION: /note="Xaa=Asp, Glu or Ala"

( i x ) FEATURE:
 ( A ) NAME/KEY: Modified-site
 ( B ) LOCATION: 10
 ( D ) OTHER INFORMATION: /note="Xaa=Tyr or same as position
6"

( i x ) FEATURE:
 ( A ) NAME/KEY: Modified-site
 ( B ) LOCATION: 12
 ( D ) OTHER INFORMATION: /note="Xaa=Arg, Leu, Orn or Lys"

( i x ) FEATURE:
 ( A ) NAME/KEY: Modified-site
 ( B ) LOCATION: 16
 ( D ) OTHER INFORMATION: /note="Xaa=Gln or Ala"

( i x ) FEATURE:
 ( A ) NAME/KEY: Modified-site
 ( B ) LOCATION: 17
 ( D ) OTHER INFORMATION: /note="Xaa=Met, Nle or Ala"

( i x ) FEATURE:
 ( A ) NAME/KEY: Modified-site
 ( B ) LOCATION: 19
 ( D ) OTHER INFORMATION: /note="Xaa=Val or Ala"

( i x ) FEATURE:
 ( A ) NAME/KEY: Modified-site
 ( B ) LOCATION: 22
 ( D ) OTHER INFORMATION: /note="Xaa=Tyr or same as position
6"

( i x ) FEATURE:
 ( A ) NAME/KEY: Modified-site
 ( B ) LOCATION: 24
 ( D ) OTHER INFORMATION: /note="Xaa=Asn or Ala"

( i x ) FEATURE:
 ( A ) NAME/KEY: Modified-site
 ( B ) LOCATION: 26
 ( D ) OTHER INFORMATION: /note="Xaa=Ile, Val, or Leu"

( i x ) FEATURE:
 ( A ) NAME/KEY: Modified-site
 ( B ) LOCATION: 27
 ( D ) OTHER INFORMATION: /note="Xaa=Leu or Lys"

( i x ) FEATURE:
 ( A ) NAME/KEY: Modified-site
 ( B ) LOCATION: 28
 ( D ) OTHER INFORMATION: /note="Xaa=Asn, Thr or Lys"

-continued (x) PUBLICATION INFORMATION:
  (H) DOCUMENT NUMBER: EP 325 044 A A
  (I) FILING DATE: 22-DEC-1987
  (J) PUBLICATION DATE: 26-JUL-1989
  (K) RELEVANT RESIDUES IN SEQ ID NO:10: FROM 18 TO 23

(xi) SEQUENCE DESCRIPTION: SEQ ID NO:10:

```
Xaa Xaa Asp Ala Val Xaa Thr Xaa Asn Xaa Thr Xaa Leu Arg Lys Xaa
 1               5                  10                      15
Xaa Ala Xaa Lys Lys Xaa Leu Xaa Asp Xaa Xaa Xaa
          20                  25
```

(2) INFORMATION FOR SEQ ID NO:11:

(i) SEQUENCE CHARACTERISTICS:
    (A) LENGTH: 28 amino acids
    (B) TYPE: amino acid
    (D) TOPOLOGY: both (ii) MOLECULE TYPE: peptide (iii) HYPOTHETICAL: NO (iv) ANTI-SENSE: NO (ix) FEATURE:
    (A) NAME/KEY: Modified-site
    (B) LOCATION: 21..25
    (D) OTHER INFORMATION: /note="Side-chains of amino acids
        21 and 25 reacted to form cyclic structure"

(ix) FEATURE:
    (A) NAME/KEY: Modified-site
    (B) LOCATION: 1
    (D) OTHER INFORMATION: /note="Xaa=His or N-methyl-Ala"

(ix) FEATURE:
    (A) NAME/KEY: Modified-site
    (B) LOCATION: 6
    (D) OTHER INFORMATION: /note="Xaa=an amino acid wherein
        the side-chain is methylcyclohexyl, methylphenyl or
        ethylphenyl wherein the phenyl ring is substituted with
        X1 and X2 independently selected from H, OH, OCH3, F, Cl,
        I, CH3, CF3, NO2, N(CH3)2, NHCOCH3, NHCOC6H5, or C(CH3)3,
        or methylnapthalene (ix) FEATURE:
    (A) NAME/KEY: Modified-site
    (B) LOCATION: 2
    (D) OTHER INFORMATION: /note="Xaa=Ser or Ala"

(ix) FEATURE:
    (A) NAME/KEY: Modified-site
    (B) LOCATION: 8
    (D) OTHER INFORMATION: /note="Xaa=Asp, Glu or Ala"

(ix) FEATURE:
    (A) NAME/KEY: Modified-site
    (B) LOCATION: 10
    (D) OTHER INFORMATION: /note="Xaa=Tyr or same as position
        6"

(ix) FEATURE:
    (A) NAME/KEY: Modified-site
    (B) LOCATION: 12
    (D) OTHER INFORMATION: /note="Xaa=Arg, Leu, Orn or Lys"

(ix) FEATURE:
    (A) NAME/KEY: Modified-site
    (B) LOCATION: 16
    (D) OTHER INFORMATION: /note="Xaa=Gln or Ala"

(ix) FEATURE:
    (A) NAME/KEY: Modified-site
    (B) LOCATION: 17
    (D) OTHER INFORMATION: /note="Xaa=Met, Nle or Ala"

( i x ) FEATURE:
    ( A ) NAME/KEY: Modified-site
    ( B ) LOCATION: 19
    ( D ) OTHER INFORMATION: /note="Xaa=Val or Ala"

( i x ) FEATURE:
    ( A ) NAME/KEY: Modified-site
    ( B ) LOCATION: 22
    ( D ) OTHER INFORMATION: /note="Xaa=Tyr or same as position 6"

( i x ) FEATURE:
    ( A ) NAME/KEY: Modified-site
    ( B ) LOCATION: 24
    ( D ) OTHER INFORMATION: /note="Xaa=Asn or Ala"

( i x ) FEATURE:
    ( A ) NAME/KEY: Modified-site
    ( B ) LOCATION: 27
    ( D ) OTHER INFORMATION: /note="Xaa=Leu or Lys"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:11: FROM 18 TO 23

( x i ) SEQUENCE DESCRIPTION: SEQ ID NO:11:

Xaa Xaa Asp Ala Val Xaa Thr Xaa Asn Xaa Thr Xaa Leu Arg Lys Xaa
1               5                   10                      15

Xaa Ala Xaa Lys Lys Xaa Leu Xaa Asp Val Xaa Thr
        20              25

( 2 ) INFORMATION FOR SEQ ID NO:12:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids 21 and 25 reacted to form cyclic structure"

( i x ) FEATURE:
        ( A ) NAME/KEY: Modified-site
        ( B ) LOCATION: 1
        ( D ) OTHER INFORMATION: /note="Xaa=His or N-methyl-Ala"

( i x ) FEATURE:
        ( A ) NAME/KEY: Modified-site
        ( B ) LOCATION: 6
        ( D ) OTHER INFORMATION: /note="Xaa=an amino acid wherein the side-chain is methylcyclohexyl, methylphenyl or ethylphenyl wherein the phenyl ring is substituted with X1 and X2 independently selected from H, OH, OCH3, F, Cl, I, CH3, CF3, NO2, N(CH3)2, NHCOCH3, NHCOC6H5, or C(CH3)3, or methylnapthalene ( i x ) FEATURE:
        ( A ) NAME/KEY: Modified-site
        ( B ) LOCATION: 2
        ( D ) OTHER INFORMATION: /note="Xaa=Ser or Ala"

( i x ) FEATURE:
        ( A ) NAME/KEY: Modified-site
        ( B ) LOCATION: 8
        ( D ) OTHER INFORMATION: /note="Xaa=Asp, Glu or Ala"

( i x ) FEATURE:
  ( A ) NAME/KEY: Modified-site
  ( B ) LOCATION: 10
  ( D ) OTHER INFORMATION: /note="Xaa=Tyr or same as position
    6"

( i x ) FEATURE:
  ( A ) NAME/KEY: Modified-site
  ( B ) LOCATION: 12
  ( D ) OTHER INFORMATION: /note="Xaa=Arg, Leu, Orn or Lys"

( i x ) FEATURE:
  ( A ) NAME/KEY: Modified-site
  ( B ) LOCATION: 16
  ( D ) OTHER INFORMATION: /note="Xaa=Gln or Ala"

( i x ) FEATURE:
  ( A ) NAME/KEY: Modified-site
  ( B ) LOCATION: 17
  ( D ) OTHER INFORMATION: /note="Xaa=Nle"

( i x ) FEATURE:
  ( A ) NAME/KEY: Modified-site
  ( B ) LOCATION: 19
  ( D ) OTHER INFORMATION: /note="Xaa=Val or Ala"

( i x ) FEATURE:
  ( A ) NAME/KEY: Modified-site
  ( B ) LOCATION: 22
  ( D ) OTHER INFORMATION: /note="Xaa=Tyr or same as position
    6"

( i x ) FEATURE:
  ( A ) NAME/KEY: Modified-site
  ( B ) LOCATION: 24
  ( D ) OTHER INFORMATION: /note="Xaa=Asn or Ala"

( i x ) FEATURE:
  ( A ) NAME/KEY: Modified-site
  ( B ) LOCATION: 27
  ( D ) OTHER INFORMATION: /note="Xaa=Leu or Lys"

( x ) PUBLICATION INFORMATION:
  ( H ) DOCUMENT NUMBER: EP 325 044 A A
  ( I ) FILING DATE: 22-DEC-1987
  ( J ) PUBLICATION DATE: 26-JUL- 1989
  ( K ) RELEVANT RESIDUES IN SEQ ID NO:12: FROM 18 TO 23

( x i ) SEQUENCE DESCRIPTION: SEQ ID NO:12:

```
Xaa Xaa Asp Ala Val Xaa Thr Xaa Asn Xaa Thr Xaa Leu Arg Lys Xaa
1               5                   10                  15

Xaa Ala Xaa Lys Lys Xaa Leu Xaa Asp Val Xaa Thr
            20                  25
```

( 2 ) INFORMATION FOR SEQ ID NO:13:

( i ) SEQUENCE CHARACTERISTICS:
    ( A ) LENGTH: 28 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 21..25
    ( D ) OTHER INFORMATION: /note="Side-chains of amino acids
      21 and 25 reacted to form cyclic structure"

( i x ) FEATURE:
    ( A ) NAME/KEY: Modified-site
    ( B ) LOCATION: 1
    ( D ) OTHER INFORMATION: /note="Xaa=His or N-methyl-Ala"

( i x ) FEATURE:
    ( A ) NAME/KEY: Modified-site
    ( B ) LOCATION: 6
    ( D ) OTHER INFORMATION: /note="Xaa=an amino acid wherein the side- chain is methylcyclohexyl, methylphenyl or ethylphenyl wherein the phenyl ring is substituted with X1 and X2 independently selected from H, OH, OCH3, F, Cl, I, CH3, CF3, NO2, N(CH3)2, NHCOCH3, NHCOC6H5, or C(CH3)3, or methylnapthalene ( i x ) FEATURE:
    ( A ) NAME/KEY: Modified-site
    ( B ) LOCATION: 2
    ( D ) OTHER INFORMATION: /note="Xaa=Ser or Ala"

( i x ) FEATURE:
    ( A ) NAME/KEY: Modified-site
    ( B ) LOCATION: 8
    ( D ) OTHER INFORMATION: /note="Xaa=Asp, Glu or Ala"

( i x ) FEATURE:
    ( A ) NAME/KEY: Modified-site
    ( B ) LOCATION: 10
    ( D ) OTHER INFORMATION: /note="Xaa=Tyr or same as position 6"

( i x ) FEATURE:
    ( A ) NAME/KEY: Modified-site
    ( B ) LOCATION: 16
    ( D ) OTHER INFORMATION: /note="Xaa=Gln or Ala"

( i x ) FEATURE:
    ( A ) NAME/KEY: Modified-site
    ( B ) LOCATION: 17
    ( D ) OTHER INFORMATION: /note="Xaa=Nle"

( i x ) FEATURE:
    ( A ) NAME/KEY: Modified-site
    ( B ) LOCATION: 22
    ( D ) OTHER INFORMATION: /note="Xaa=Tyr or same as position 6"

( i x ) FEATURE:
    ( A ) NAME/KEY: Modified-site
    ( B ) LOCATION: 24
    ( D ) OTHER INFORMATION: /note="Xaa=Asn or Ala"

( i x ) FEATURE:
    ( A ) NAME/KEY: Modified-site
    ( B ) LOCATION: 27
    ( D ) OTHER INFORMATION: /note="Xaa=Leu or Lys"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:13: FROM 18 TO 23

( x i ) SEQUENCE DESCRIPTION: SEQ ID NO:13:

Xaa Xaa Asp Ala Val Xaa Thr Xaa Asn Xaa Thr Leu Leu Arg Lys Xaa
1                      5                            10                          15

Xaa Ala Ala Lys Lys Xaa Leu Xaa Asp Val Xaa Thr
              20                            25

( 2 ) INFORMATION FOR SEQ ID NO:14:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO 5,677,419

( i x ) FEATURE:
    ( A ) NAME/KEY: Modified-site
    ( B ) LOCATION: 21..25
    ( D ) OTHER INFORMATION: /note="Side-chains of amino acids
        21 and 25 reacted to form cyclic structure"

( i x ) FEATURE:
    ( A ) NAME/KEY: Modified-site
    ( B ) LOCATION: 1
    ( D ) OTHER INFORMATION: /note="Xaa=His or N-methyl-Ala"

( i x ) FEATURE:
    ( A ) NAME/KEY: Modified-site
    ( B ) LOCATION: 6
    ( D ) OTHER INFORMATION: /note="Xaa=an amino acid wherein
        the side- chain is methylcyclohexyl, methylphenyl or
        ethylphenyl wherein the phenyl ring is substituted with
        X1 and X2 independently selected from H, OH, OCH3, F, Cl,
        I, CH3, CF3, NO2, N(CH3)2, NHCOCH3, NHCOC6H5, or C(CH3)3,
        or methylnapthalene ( i x ) FEATURE:
    ( A ) NAME/KEY: Modified-site
    ( B ) LOCATION: 2
    ( D ) OTHER INFORMATION: /note="Xaa=Ser or Ala"

( i x ) FEATURE:
    ( A ) NAME/KEY: Modified-site
    ( B ) LOCATION: 8
    ( D ) OTHER INFORMATION: /note="Xaa=Asp, Glu or Ala"

( i x ) FEATURE:
    ( A ) NAME/KEY: Modified-site
    ( B ) LOCATION: 10
    ( D ) OTHER INFORMATION: /note="Xaa=Tyr or same as position 6"

( i x ) FEATURE:
    ( A ) NAME/KEY: Modified-site
    ( B ) LOCATION: 16
    ( D ) OTHER INFORMATION: /note="Xaa=Gln or Ala"

( i x ) FEATURE:
    ( A ) NAME/KEY: Modified-site
    ( B ) LOCATION: 17
    ( D ) OTHER INFORMATION: /note="Xaa=Nle"

( i x ) FEATURE:
    ( A ) NAME/KEY: Modified-site
    ( B ) LOCATION: 19
    ( D ) OTHER INFORMATION: /note="Xaa=Val or Ala"

( i x ) FEATURE:
    ( A ) NAME/KEY: Modified-site
    ( B ) LOCATION: 22
    ( D ) OTHER INFORMATION: /note="Xaa=Tyr or same as position 6"

( i x ) FEATURE:
    ( A ) NAME/KEY: Modified-site
    ( B ) LOCATION: 24
    ( D ) OTHER INFORMATION: /note="Xaa=Asn or Ala"

( i x ) FEATURE:
    ( A ) NAME/KEY: Modified-site
    ( B ) LOCATION: 27
    ( D ) OTHER INFORMATION: /note="Xaa=Leu or Lys"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL- 1989
    ( K ) RELEVANT RESIDUES IN SEQ ID NO:14: FROM 18 TO 23

( x i ) SEQUENCE DESCRIPTION: SEQ ID NO:14:

```
Xaa  Xaa  Asp  Ala  Val  Xaa  Thr  Xaa  Asn  Xaa  Thr  Lys  Leu  Arg  Lys  Xaa
 1              5                        10                           15
```

```
Xaa Ala Xaa Lys Lys Xaa Leu Xaa Asp Val Xaa Thr
         20              25
```

(2) INFORMATION FOR SEQ ID NO:15:

(i) SEQUENCE CHARACTERISTICS:
    (A) LENGTH: 28 amino acids
    (B) TYPE: amino acid
    (D) TOPOLOGY: both (ii) MOLECULE TYPE: peptide (iii) HYPOTHETICAL: NO (iv) ANTI-SENSE: NO (ix) FEATURE:
    (A) NAME/KEY: Modified-site
    (B) LOCATION: 21..25
    (D) OTHER INFORMATION: /note="Side-chains of amino acids
        21 and 25 reacted to form cyclic structure"

(ix) FEATURE:
    (A) NAME/KEY: Modified-site
    (B) LOCATION: 1
    (D) OTHER INFORMATION: /note="Xaa=His or N-methyl-Ala"

(ix) FEATURE:
    (A) NAME/KEY: Modified-site
    (B) LOCATION: 6
    (D) OTHER INFORMATION: /note="Xaa=an amino acid wherein
        the side-chain is methylcyclohexyl, methylphenyl or
        ethylphenyl wherein the phenyl ring is substituted with
        X1 and X2 independently selected from H, OH, OCH3, F, Cl,
        I, CH3, CF3, NO2, N(CH3)2, NHCOCH3, NHCOC6H5, or C(CH3)3,
        or methylnapthalene (ix) FEATURE:
    (A) NAME/KEY: Modified-site
    (B) LOCATION: 2
    (D) OTHER INFORMATION: /note="Xaa=Ser or Ala"

(ix) FEATURE:
    (A) NAME/KEY: Modified-site
    (B) LOCATION: 8
    (D) OTHER INFORMATION: /note="Xaa=Asp, Glu or Ala"

(ix) FEATURE:
    (A) NAME/KEY: Modified-site
    (B) LOCATION: 10
    (D) OTHER INFORMATION: /note="Xaa=Tyr or same as position
        6"

(ix) FEATURE:
    (A) NAME/KEY: Modified-site
    (B) LOCATION: 16
    (D) OTHER INFORMATION: /note="Xaa=Gln or Ala"

(ix) FEATURE:
    (A) NAME/KEY: Modified-site
    (B) LOCATION: 17
    (D) OTHER INFORMATION: /note="Xaa=Nle"

(ix) FEATURE:
    (A) NAME/KEY: Modified-site
    (B) LOCATION: 22
    (D) OTHER INFORMATION: /note="Xaa=Tyr or same as position
        6"

(ix) FEATURE:
    (A) NAME/KEY: Modified-site
    (B) LOCATION: 24
    (D) OTHER INFORMATION: /note="Xaa=Asn or Ala"

(ix) FEATURE:
    (A) NAME/KEY: Modified-site
    (B) LOCATION: 27
    (D) OTHER INFORMATION: /note="Xaa=Leu or Lys"

( x ) PUBLICATION INFORMATION:
  ( H ) DOCUMENT NUMBER: EP 325 044 A A
  ( I ) FILING DATE: 22-DEC-1987
  ( J ) PUBLICATION DATE: 26-JUL-1989
  ( K ) RELEVANT RESIDUES IN SEQ ID NO:15: FROM 18 TO 23

( x i ) SEQUENCE DESCRIPTION: SEQ ID NO:15:

```
Xaa Xaa Asp Ala Val Xaa Thr Xaa Asn Xaa Thr Lys Leu Arg Lys Xaa
 1               5                   10                  15
Xaa Ala Ala Lys Lys Xaa Leu Xaa Asp Val Xaa Thr
             20              25
```

( 2 ) INFORMATION FOR SEQ ID NO:16:

( i ) SEQUENCE CHARACTERISTICS:
    ( A ) LENGTH: 28 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 21..25
    ( D ) OTHER INFORMATION: /note="Side-chains of amino acids
          21 and 25 reacted to form cyclic structure"

( i x ) FEATURE:
    ( A ) NAME/KEY: Modified-site
    ( B ) LOCATION: 1
    ( D ) OTHER INFORMATION: /note="Xaa=His or N-methyl-Ala"

( i x ) FEATURE:
    ( A ) NAME/KEY: Modified-site
    ( B ) LOCATION: 6
    ( D ) OTHER INFORMATION: /note="Xaa=an amino acid wherein
          the side-chain is methylcyclohexyl, methylphenyl or
          ethylphenyl wherein the phenyl ring is substituted with
          X1 and X2 independently selected from H, OH, OCH3, F, Cl,
          I, CH3, CF3, NO2, N(CH3)2, NHCOCH3, NHCOC6H5, or C(CH3)3,
          or methylnapthalene ( i x ) FEATURE:
    ( A ) NAME/KEY: Modified-site
    ( B ) LOCATION: 2
    ( D ) OTHER INFORMATION: /note="Xaa=Ser or Ala"

( i x ) FEATURE:
    ( A ) NAME/KEY: Modified-site
    ( B ) LOCATION: 8
    ( D ) OTHER INFORMATION: /note="Xaa=Asp, Glu or Ala"

( i x ) FEATURE:
    ( A ) NAME/KEY: Modified-site
    ( B ) LOCATION: 10
    ( D ) OTHER INFORMATION: /note="Xaa=Tyr or same as position
          6"

( i x ) FEATURE:
    ( A ) NAME/KEY: Modified-site
    ( B ) LOCATION: 12
    ( D ) OTHER INFORMATION: /note="Xaa=Arg, Leu, Orn or Lys"

( i x ) FEATURE:
    ( A ) NAME/KEY: Modified-site
    ( B ) LOCATION: 16
    ( D ) OTHER INFORMATION: /note="Xaa=Gln or Ala"

( i x ) FEATURE:
    ( A ) NAME/KEY: Modified-site
    ( B ) LOCATION: 17
    ( D ) OTHER INFORMATION: /note="Xaa=Met, Nle or Ala"

( i x ) FEATURE:
    ( A ) NAME/KEY: Modified-site
    ( B ) LOCATION: 19
    ( D ) OTHER INFORMATION: /note="Xaa=Val or Ala"

( i x ) FEATURE:
    ( A ) NAME/KEY: Modified-site
    ( B ) LOCATION: 22
    ( D ) OTHER INFORMATION: /note="Xaa=Tyr or same as position 6"

( i x ) FEATURE:
    ( A ) NAME/KEY: Modified-site
    ( B ) LOCATION: 24
    ( D ) OTHER INFORMATION: /note="Xaa=Asn or Ala"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:16: FROM 18 TO 23

( x i ) SEQUENCE DESCRIPTION: SEQ ID NO:16:

```
Xaa Xaa Asp Ala Val Xaa Thr Xaa Asn Xaa Thr Xaa Leu Arg Lys Xaa
 1               5                   10                  15
Xaa Ala Xaa Lys Lys Xaa Leu Xaa Asp Leu Lys Lys
            20                  25
```

( 2 ) INFORMATION FOR SEQ ID NO:17:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids 21 and 25 reacted to form cyclic structure"

( i x ) FEATURE:
        ( A ) NAME/KEY: Modified-site
        ( B ) LOCATION: 1
        ( D ) OTHER INFORMATION: /note="Xaa=His or N-methyl-Ala"

( i x ) FEATURE:
        ( A ) NAME/KEY: Modified-site
        ( B ) LOCATION: 6
        ( D ) OTHER INFORMATION: /note="Xaa=an amino acid wherein the side-chain is methylcyclohexyl, methylphenyl or ethylphenyl wherein the phenyl ring is substituted with X1 and X2 independently selected from H, OH, OCH3, F, Cl, I, CH3, CF3, NO2, N(CH3)2, NHCOCH3, NHCOC6H5, or C(CH3)3, or methylnapthalene"

( i x ) FEATURE:
        ( A ) NAME/KEY: Modified-site
        ( B ) LOCATION: 2
        ( D ) OTHER INFORMATION: /note="Xaa=Ser or Ala"

( i x ) FEATURE:
        ( A ) NAME/KEY: Modified-site
        ( B ) LOCATION: 8
        ( D ) OTHER INFORMATION: /note="Xaa=Asp, Glu or Ala"

( i x ) FEATURE:
        ( A ) NAME/KEY: Modified-site
        ( B ) LOCATION: 10
        ( D ) OTHER INFORMATION: /note="Xaa=Tyr or same as position 6"

( i x ) FEATURE:
     ( A ) NAME/KEY: Modified-site
     ( B ) LOCATION: 16
     ( D ) OTHER INFORMATION: /note="Xaa=Gln or Ala"

( i x ) FEATURE:
     ( A ) NAME/KEY: Modified-site
     ( B ) LOCATION: 22
     ( D ) OTHER INFORMATION: /note="Xaa=Tyr or same as position 6"

( i x ) FEATURE:
     ( A ) NAME/KEY: Modified-site
     ( B ) LOCATION: 24
     ( D ) OTHER INFORMATION: /note="Xaa=Asn or Ala"

( x ) PUBLICATION INFORMATION:
     ( H ) DOCUMENT NUMBER: EP 325 044 A A
     ( I ) FILING DATE: 22-DEC-1987
     ( J ) PUBLICATION DATE: 26-JUL-1989
     ( K ) RELEVANT RESIDUES IN SEQ ID NO:17: FROM 18 TO 23

( x i ) SEQUENCE DESCRIPTION: SEQ ID NO:17:

```
Xaa Xaa Asp Ala Val Xaa Thr Xaa Asn Xaa Thr Lys Leu Arg Lys Xaa
 1               5                   10                      15
Ala Ala Ala Lys Lys Xaa Leu Xaa Asp Leu Lys Lys
            20              25
```

( 2 ) INFORMATION FOR SEQ ID NO:18:

( i ) SEQUENCE CHARACTERISTICS:
     ( A ) LENGTH: 28 amino acids
     ( B ) TYPE: amino acid
     ( D ) TOPOLOGY: both ( i i ) MOLECULE TYPE: peptide ( i i i ) HYPOTHETICAL: NO ( i v ) ANTI-SENSE: NO ( i x ) FEATURE:
     ( A ) NAME/KEY: Modified-site
     ( B ) LOCATION: 21..25
     ( D ) OTHER INFORMATION: /note="Side-chains of amino acids 21 and 25 reacted to form cyclic structure"

( i x ) FEATURE:
     ( A ) NAME/KEY: Modified-site
     ( B ) LOCATION: 1
     ( D ) OTHER INFORMATION: /note="Xaa=His or N-methyl-Ala"

( i x ) FEATURE:
     ( A ) NAME/KEY: Modified-site
     ( B ) LOCATION: 6
     ( D ) OTHER INFORMATION: /note="Xaa=an amino acid wherein the side-chain is methylcyclohexyl, methylphenyl or ethylphenyl wherein the phenyl ring is substituted with X1 and X2 independently selected from H, OH, OCH3, F, Cl, I, CH3, CF3, NO2, N(CH3)2, NHCOCH3, NHCOC6H5, or C(CH3)3, or methylnapthalene"

( i x ) FEATURE:
     ( A ) NAME/KEY: Modified-site
     ( B ) LOCATION: 2
     ( D ) OTHER INFORMATION: /note="Xaa=Ser or Ala"

( i x ) FEATURE:
     ( A ) NAME/KEY: Modified-site
     ( B ) LOCATION: 8
     ( D ) OTHER INFORMATION: /note="Xaa=Asp, Glu or Ala"

( i x ) FEATURE:
     ( A ) NAME/KEY: Modified-site
     ( B ) LOCATION: 10
     ( D ) OTHER INFORMATION: /note="Xaa=Tyr or same as position ( i x ) FEATURE:
    ( A ) NAME/KEY: Modified-site
    ( B ) LOCATION: 16
    ( D ) OTHER INFORMATION: /note="Xaa=Gln or Ala"

( i x ) FEATURE:
    ( A ) NAME/KEY: Modified-site
    ( B ) LOCATION: 17
    ( D ) OTHER INFORMATION: /note="Xaa=Nle"

( i x ) FEATURE:
    ( A ) NAME/KEY: Modified-site
    ( B ) LOCATION: 19
    ( D ) OTHER INFORMATION: /note="Xaa=Val or Ala"

( i x ) FEATURE:
    ( A ) NAME/KEY: Modified-site
    ( B ) LOCATION: 22
    ( D ) OTHER INFORMATION: /note="Xaa=Tyr or same as position 6"

( i x ) FEATURE:
    ( A ) NAME/KEY: Modified-site
    ( B ) LOCATION: 24
    ( D ) OTHER INFORMATION: /note="Xaa=Asn or Ala"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:18: FROM 18 TO 23

( x i ) SEQUENCE DESCRIPTION: SEQ ID NO:18:

```
Xaa Xaa Asp Ala Val Xaa Thr Xaa Asn Xaa Thr Lys Leu Arg Lys Xaa
 1               5                  10                  15
Xaa Ala Xaa Lys Lys Xaa Leu Xaa Asp Leu Lys Lys
             20                  25
```

( 2 ) INFORMATION FOR SEQ ID NO:19:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids 21 and 25 reacted to form cyclic structure"

( i x ) FEATURE:
        ( A ) NAME/KEY: Modified-site
        ( B ) LOCATION: 1
        ( D ) OTHER INFORMATION: /note="Xaa=His or N-methyl-Ala"

( i x ) FEATURE:
        ( A ) NAME/KEY: Modified-site
        ( B ) LOCATION: 6
        ( D ) OTHER INFORMATION: /note="Xaa=an amino acid wherein the side-chain is methylcyclohexyl, methylphenyl or ethylphenyl wherein the phenyl ring is substituted with X1 and X2 independently selected from H, OH, OCH3, F, Cl, I, CH3, CF3, NO2, N(CH3)2, NHCOCH3, NHCOC6H5, or C(CH3)3, or methylnapthalene"

( i x ) FEATURE:
        ( A ) NAME/KEY: Modified-site
        ( B ) LOCATION: 2

( D ) OTHER INFORMATION: /note="Xaa=Ser or Ala"

( i x ) FEATURE:
    ( A ) NAME/KEY: Modified-site
    ( B ) LOCATION: 8
    ( D ) OTHER INFORMATION: /note="Xaa=Asp, Glu or Ala"

( i x ) FEATURE:
    ( A ) NAME/KEY: Modified-site
    ( B ) LOCATION: 10
    ( D ) OTHER INFORMATION: /note="Xaa=Tyr or same as position 6"

( i x ) FEATURE:
    ( A ) NAME/KEY: Modified-site
    ( B ) LOCATION: 16
    ( D ) OTHER INFORMATION: /note="Xaa=Gln or Ala"

( i x ) FEATURE:
    ( A ) NAME/KEY: Modified-site
    ( B ) LOCATION: 17
    ( D ) OTHER INFORMATION: /note="Xaa=Nle"

( i x ) FEATURE:
    ( A ) NAME/KEY: Modified-site
    ( B ) LOCATION: 22
    ( D ) OTHER INFORMATION: /note="Xaa=Tyr or same as position 6"

( i x ) FEATURE:
    ( A ) NAME/KEY: Modified-site
    ( B ) LOCATION: 24
    ( D ) OTHER INFORMATION: /note="Xaa=Asn or Ala"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:19: FROM 18 TO 23

( x i ) SEQUENCE DESCRIPTION: SEQ ID NO:19:

```
Xaa Xaa Asp Ala Val Xaa Thr Xaa Asn Xaa Thr Lys Leu Arg Lys Xaa
 1               5                  10                      15
Xaa Ala Ala Lys Lys Xaa Leu Xaa Asp Leu Lys Lys
              20              25
```

( 2 ) INFORMATION FOR SEQ ID NO:20:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 8..12
        ( D ) OTHER INFORMATION: /note="Side-chains of amino acids 8 and 12 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:20: FROM 18 TO 23

( x i ) SEQUENCE DESCRIPTION: SEQ ID NO:20:

```
His Ser Asp Ala Val Phe Thr Asp Asn Tyr Thr Lys Leu Arg Lys Gln
 1               5                   10                  15

Xaa Ala Val Lys Lys Tyr Leu Asp Ser Val Leu Thr
            20              25
```

(2) INFORMATION FOR SEQ ID NO:21:

(i) SEQUENCE CHARACTERISTICS:
        (A) LENGTH: 28 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 8..12
        (D) OTHER INFORMATION: /note="Side-chains of amino acids
            8 and 12 reacted to form cyclic structure"

(ix) FEATURE:
        (A) NAME/KEY: Modified-site
        (B) LOCATION: 17
        (D) OTHER INFORMATION: /note="Xaa=Nle"

(x) PUBLICATION INFORMATION:
        (H) DOCUMENT NUMBER: EP 325 044 A A
        (I) FILING DATE: 22-DEC-1987
        (J) PUBLICATION DATE: 26-JUL-1989
        (K) RELEVANT RESIDUES IN SEQ ID NO:21: FROM 18 TO 23

(xi) SEQUENCE DESCRIPTION: SEQ ID NO:21:

```
His Ser Asp Ala Val Phe Thr Glu Asn Tyr Thr Lys Leu Arg Lys Gln
 1               5                   10                  15

Xaa Ala Val Lys Lys Tyr Leu Asn Ser Val Leu Thr
            20              25
```

(2) INFORMATION FOR SEQ ID NO:22:

(i) SEQUENCE CHARACTERISTICS:
        (A) LENGTH: 28 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 9..12
        (D) OTHER INFORMATION: /note="Side-chains of amino acids
            9 and 12 reacted to form cyclic structure"

(ix) FEATURE:
        (A) NAME/KEY: Modified-site
        (B) LOCATION: 17
        (D) OTHER INFORMATION: /note="Xaa=Nle"

(x) PUBLICATION INFORMATION:
        (H) DOCUMENT NUMBER: EP 325 044 A A
        (I) FILING DATE: 22-DEC-1987
        (J) PUBLICATION DATE: 26-JUL-1989
        (K) RELEVANT RESIDUES IN SEQ ID NO:22: FROM 18 TO 23

(xi) SEQUENCE DESCRIPTION: SEQ ID NO:22:

```
His Ser Asp Ala Val Phe Thr Asn Asp Tyr Thr Lys Leu Arg Lys Gln
```

Xaa Ala Val Lys Lys Tyr Leu Asn Ser Val Leu Thr
            20                      25

( 2 ) INFORMATION FOR SEQ ID NO:23:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 8..12
        ( D ) OTHER INFORMATION: /note="Side-chains of amino acids
            8 and 12 reacted to form cyclic structure"

( i x ) FEATURE:
        ( A ) NAME/KEY: Modified-site
        ( B ) LOCATION: 12
        ( D ) OTHER INFORMATION: /note="Xaa=Orn"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:23: FROM 18 TO 23

( x i ) SEQUENCE DESCRIPTION: SEQ ID NO:23:

His Ser Asp Ala Val Phe Thr Asp Asn Tyr Thr Xaa Leu Arg Lys Gln
1               5                   10                  15
Xaa Ala Val Lys Lys Tyr Leu Asn Ser Val Leu Thr
            20                      25

( 2 ) INFORMATION FOR SEQ ID NO:24:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 8..12
        ( D ) OTHER INFORMATION: /note="Side-chains of amino acids
            8 and 12 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:24: FROM 18 TO 23

( x i ) SEQUENCE DESCRIPTION: SEQ ID NO:24:

His Ser Asp Ala Val Phe Thr Lys Asn Tyr Thr Asp Leu Arg Lys Gln
1               5                   10                  15

Xaa Ala Val Lys Lys Tyr Leu Asn Ser Val Leu Thr
            20              25

( 2 ) INFORMATION FOR SEQ ID NO:25:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 8..12
        ( D ) OTHER INFORMATION: /note="Side-chains of amino acids
            8 and 12 reacted to form cyclic structure"

( i x ) FEATURE:
        ( A ) NAME/KEY: Modified-site
        ( B ) LOCATION: 12
        ( D ) OTHER INFORMATION: /note="Xaa=Orn"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:25: FROM 18 TO 23

( x i ) SEQUENCE DESCRIPTION: SEQ ID NO:25:

His Ser Asp Ala Val Phe Thr Glu Asn Tyr Thr Xaa Leu Arg Lys Gln
1               5                   10                  15

Xaa Ala Val Lys Lys Tyr Leu Asn Ser Val Leu Thr
            20              25

( 2 ) INFORMATION FOR SEQ ID NO:26:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 12..16
        ( D ) OTHER INFORMATION: /note="Side-chains of amino acids
            12 and 16 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987

( J ) PUBLICATION DATE: 26-JUL- 1989
( K ) RELEVANT RESIDUES IN SEQ ID NO:26: FROM 18 TO 23

( x i ) SEQUENCE DESCRIPTION: SEQ ID NO:26:

```
His Ser Asp Ala Val Phe Thr Asp Asn Tyr Thr Lys Leu Arg Lys Glu
1               5                   10                  15
Xaa Ala Val Lys Lys Tyr Leu Asn Ser Val Leu Thr
            20                  25
```

( 2 ) INFORMATION FOR SEQ ID NO:27:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 20..24
        ( D ) OTHER INFORMATION: /note="Side-chains of amino acids 20 and 24 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL- 1989
        ( K ) RELEVANT RESIDUES IN SEQ ID NO:27: FROM 18 TO 23

( x i ) SEQUENCE DESCRIPTION: SEQ ID NO:27:

```
His Ser Asp Ala Val Phe Thr Asp Asn Tyr Thr Lys Leu Arg Lys Gln
1               5                   10                  15
Xaa Ala Val Lys Lys Tyr Leu Asp Ser Val Leu Thr
            20                  25
```

( 2 ) INFORMATION FOR SEQ ID NO:28:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids 21 and 25 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:28: FROM 18 TO 23

( x i ) SEQUENCE DESCRIPTION: SEQ ID NO:28:

His Ser Asp Ala Val Phe Thr Asp Asn Tyr Thr Lys Leu Arg Lys Gln
1               5                   10                  15

Xaa Ala Val Lys Lys Tyr Leu Asn Asp Val Leu Thr
            20              25

( 2 ) INFORMATION FOR SEQ ID NO:29:

( i ) SEQUENCE CHARACTERISTICS:
       ( A ) LENGTH: 28 amino acids
       ( B ) TYPE: amino acid
       ( D ) TOPOLOGY: both ( i i ) MOLECULE TYPE: peptide ( i i i ) HYPOTHETICAL: NO ( i v ) ANTI-SENSE: NO ( i x ) FEATURE:
       ( A ) NAME/KEY: Modified-site
       ( B ) LOCATION: 21..25
       ( D ) OTHER INFORMATION: /note="Side-chains of amino acids
           21 and 25 reacted to form cyclic structure"

( i x ) FEATURE:
       ( A ) NAME/KEY: Modified-site
       ( B ) LOCATION: 17
       ( D ) OTHER INFORMATION: /note="Xaa=Nle"

( x ) PUBLICATION INFORMATION:
       ( H ) DOCUMENT NUMBER: EP 325 044 A A
       ( I ) FILING DATE: 22-DEC-1987
       ( J ) PUBLICATION DATE: 26-JUL-1989
       ( K ) RELEVANT RESIDUES IN SEQ ID NO:29: FROM 18 TO 23

( x i ) SEQUENCE DESCRIPTION: SEQ ID NO:29:

His Ser Asp Ala Val Phe Thr Asp Asn Tyr Thr Lys Leu Arg Lys Gln
1               5                   10                  15

Xaa Ala Ala Lys Lys Tyr Leu Asn Asp Val Leu Thr
            20              25

( 2 ) INFORMATION FOR SEQ ID NO:30:

( i ) SEQUENCE CHARACTERISTICS:
       ( A ) LENGTH: 31 amino acids
       ( B ) TYPE: amino acid
       ( D ) TOPOLOGY: both ( i i ) MOLECULE TYPE: peptide ( i i i ) HYPOTHETICAL: NO ( i v ) ANTI-SENSE: NO ( i x ) FEATURE:
       ( A ) NAME/KEY: Modified-site
       ( B ) LOCATION: 21..25
       ( D ) OTHER INFORMATION: /note="Side-chains of amino acids
           21 and 25 reacted to form cyclic structure"

( i x ) FEATURE:
       ( A ) NAME/KEY: Modified-site
       ( B ) LOCATION: 17
       ( D ) OTHER INFORMATION: /note="Xaa=Nle"

( i x ) FEATURE:
       ( A ) NAME/KEY: Modified-site
       ( B ) LOCATION: 6
       ( D ) OTHER INFORMATION: /note="Xaa=p-F-Phe"

( i x ) FEATURE:
       ( A ) NAME/KEY: Modified-site ( B ) LOCATION: 10
            ( D ) OTHER INFORMATION: /note="Xaa=2-Nal"

( x ) PUBLICATION INFORMATION:
            ( H ) DOCUMENT NUMBER: EP 325 044 A A
            ( I ) FILING DATE: 22-DEC-1987
            ( J ) PUBLICATION DATE: 26-JUL- 1989
            ( K ) RELEVANT RESIDUES IN SEQ ID NO:30: FROM 18 TO 23

( x i ) SEQUENCE DESCRIPTION: SEQ ID NO:30:

His Ser Asp Ala Val Xaa Thr Asp Asn Xaa Thr Lys Leu Arg Lys Gln
    1               5                   10                  15

Xaa Ala Val Lys Lys Tyr Leu Asn Asp Val Leu Thr Gly Gly Met
                    20                  25                  30

( 2 ) INFORMATION FOR SEQ ID NO:31:

( i ) SEQUENCE CHARACTERISTICS:
            ( A ) LENGTH: 28 amino acids
            ( B ) TYPE: amino acid
            ( D ) TOPOLOGY: both ( i i ) MOLECULE TYPE: peptide ( i i i ) HYPOTHETICAL: NO ( i v ) ANTI-SENSE: NO ( i x ) FEATURE:
            ( A ) NAME/KEY: Modified-site
            ( B ) LOCATION: 21..25
            ( D ) OTHER INFORMATION: /note="Side-chains of amino acids
                    21 and 25 reacted to form cyclic structure"

( i x ) FEATURE:
            ( A ) NAME/KEY: Modified-site
            ( B ) LOCATION: 17
            ( D ) OTHER INFORMATION: /note="Xaa=Nle"

( i x ) FEATURE:
            ( A ) NAME/KEY: Modified-site
            ( B ) LOCATION: 12
            ( D ) OTHER INFORMATION: /note="Xaa=Orn"

( x ) PUBLICATION INFORMATION:
            ( H ) DOCUMENT NUMBER: EP 325 044 A A
            ( I ) FILING DATE: 22-DEC-1987
            ( J ) PUBLICATION DATE: 26-JUL- 1989
            ( K ) RELEVANT RESIDUES IN SEQ ID NO:31: FROM 18 TO 23

( x i ) SEQUENCE DESCRIPTION: SEQ ID NO:31:

His Ser Asp Ala Val Phe Thr Glu Asn Tyr Thr Xaa Leu Arg Lys Gln
    1               5                   10                  15

Xaa Ala Val Lys Lys Tyr Leu Asn Asp Val Leu Thr
                    20                  25

( 2 ) INFORMATION FOR SEQ ID NO:32:

( i ) SEQUENCE CHARACTERISTICS:
            ( A ) LENGTH: 31 amino acids
            ( B ) TYPE: amino acid
            ( D ) TOPOLOGY: both ( i i ) MOLECULE TYPE: peptide ( i i i ) HYPOTHETICAL: NO ( i v ) ANTI-SENSE: NO ( i x ) FEATURE:
            ( A ) NAME/KEY: Modified-site
            ( B ) LOCATION: 21..25
            ( D ) OTHER INFORMATION: /note="Side-chains of amino acids
                    21 and 25 reacted to form cyclic structure"

( i x ) FEATURE:
    ( A ) NAME/KEY: Modified-site
    ( B ) LOCATION: 17
    ( D ) OTHER INFORMATION: /note="Xaa=Nle"

( i x ) FEATURE:
    ( A ) NAME/KEY: Modified-site
    ( B ) LOCATION: 6
    ( D ) OTHER INFORMATION: /note="Xaa=p-F-Phe"

( i x ) FEATURE:
    ( A ) NAME/KEY: Modified-site
    ( B ) LOCATION: 31
    ( D ) OTHER INFORMATION: /note="Xaa=Cys(Acm)"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:32: FROM 18 TO 23

( x i ) SEQUENCE DESCRIPTION: SEQ ID NO:32:

```
His Ser Asp Ala Val Xaa Thr Asp Asn Tyr Thr Lys Leu Arg Lys Gln
 1               5                  10                  15
Xaa Ala Ala Lys Lys Tyr Leu Asn Asp Val Leu Thr Gly Gly Xaa
            20                  25                  30
```

( 2 ) INFORMATION FOR SEQ ID NO:33:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids
            21 and 25 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:33: FROM 18 TO 23

( x i ) SEQUENCE DESCRIPTION: SEQ ID NO:33:

```
His Ala Asp Ala Val Phe Thr Asp Asn Tyr Thr Lys Leu Arg Lys Gln
 1               5                  10                  15
Xaa Ala Ala Lys Lys Tyr Leu Asn Asp Val Leu Thr
            20                  25
```

( 2 ) INFORMATION FOR SEQ ID NO:34:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 21..25
    ( D ) OTHER INFORMATION: /note="Side-chains of amino acids
        21 and 25 reacted to form cyclic structure"

( i x ) FEATURE:
    ( A ) NAME/KEY: Modified-site
    ( B ) LOCATION: 17
    ( D ) OTHER INFORMATION: /note="Xaa=Nle"

( i x ) FEATURE:
    ( A ) NAME/KEY: Modified-site
    ( B ) LOCATION: 1
    ( D ) OTHER INFORMATION: /note="Xaa=N-methyl-Ala"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:34: FROM 18 TO 23

( x i ) SEQUENCE DESCRIPTION: SEQ ID NO:34:

```
Xaa  Ser  Asp  Ala  Val  Phe  Thr  Asp  Asn  Tyr  Thr  Lys  Leu  Arg  Lys  Gln
1                   5                        10                            15

Xaa  Ala  Ala  Lys  Lys  Tyr  Leu  Asn  Asp  Val  Leu  Thr
                20                       25
```

( 2 ) INFORMATION FOR SEQ ID NO:35:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 21..25
    ( D ) OTHER INFORMATION: /note="Side-chains of amino acids
        21 and 25 reacted to form cyclic structure"

( i x ) FEATURE:
    ( A ) NAME/KEY: Modified-site
    ( B ) LOCATION: 17
    ( D ) OTHER INFORMATION: /note="Xaa=Nle"

( i x ) FEATURE:
    ( A ) NAME/KEY: Modified-site
    ( B ) LOCATION: 10
    ( D ) OTHER INFORMATION: /note="Xaa=2-Nal"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:35: FROM 18 TO 23

( x i ) SEQUENCE DESCRIPTION: SEQ ID NO:35:

```
His  Ser  Asp  Ala  Val  Phe  Thr  Asp  Asn  Xaa  Thr  Leu  Leu  Arg  Lys  Gln
1                   5                        10                            15

Xaa  Ala  Ala  Lys  Lys  Tyr  Leu  Asn  Asp  Val  Leu  Thr
                20                       25
```

( 2 ) INFORMATION FOR SEQ ID NO:36:

( i ) SEQUENCE CHARACTERISTICS:
    ( A ) LENGTH: 28 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 21..25
    ( D ) OTHER INFORMATION: /note="Side-chains of amino acids
        21 and 25 reacted to form cyclic structure"

( i x ) FEATURE:
    ( A ) NAME/KEY: Modified-site
    ( B ) LOCATION: 17
    ( D ) OTHER INFORMATION: /note="Xaa=Nle"

( i x ) FEATURE:
    ( A ) NAME/KEY: Modified-site
    ( B ) LOCATION: 10
    ( D ) OTHER INFORMATION: /note="Xaa=O-Methyl-Tyr"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:36: FROM 18 TO 23

( x i ) SEQUENCE DESCRIPTION: SEQ ID NO:36:

His  Ser  Asp  Ala  Val  Phe  Thr  Asp  Asn  Xaa  Thr  Leu  Leu  Arg  Lys  Gln
1                   5                        10                       15

Xaa  Ala  Ala  Lys  Lys  Tyr  Leu  Asn  Asp  Val  Leu  Thr
               20                   25

( 2 ) INFORMATION FOR SEQ ID NO:37:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids
            21 and 25 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( i x ) FEATURE:
        ( A ) NAME/KEY: Modified-site
        ( B ) LOCATION: 6
        ( D ) OTHER INFORMATION: /note="Xaa=p-F-Phe"

( i x ) FEATURE:
        ( A ) NAME/KEY: Modified-site
        ( B ) LOCATION: 10
        ( D ) OTHER INFORMATION: /note="Xaa=p-NH2-Phe"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989

5,677,419

117

118

-continued ( K ) RELEVANT RESIDUES IN SEQ ID NO:37: FROM 18 TO 23

( x i ) SEQUENCE DESCRIPTION: SEQ ID NO:37:

```
His  Ser  Asp  Ala  Val  Xaa  Thr  Asp  Asn  Xaa  Thr  Leu  Leu  Arg  Lys  Gln
1                  5                        10                            15

Xaa  Ala  Ala  Lys  Lys  Tyr  Leu  Asn  Asp  Val  Leu  Thr
               20                       25
```

( 2 ) INFORMATION FOR SEQ ID NO:38:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids
            21 and 25 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:38: FROM 18 TO 23

( x i ) SEQUENCE DESCRIPTION: SEQ ID NO:38:

```
His  Ser  Asp  Ala  Val  Phe  Thr  Asp  Asn  Tyr  Thr  Lys  Leu  Arg  Lys  Gln
1                  5                        10                            15

Xaa  Ala  Ala  Lys  Lys  Tyr  Leu  Asn  Asp  Leu  Lys  Lys
               20                       25
```

( 2 ) INFORMATION FOR SEQ ID NO:39:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids
            21 and 25 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( i x ) FEATURE:
        ( A ) NAME/KEY: Modified-site
        ( B ) LOCATION: 1
        ( D ) OTHER INFORMATION: /note="Xaa=N-methyl-Ala"

( x ) PUBLICATION INFORMATION:

( H ) DOCUMENT NUMBER: EP 325 044 A A
            ( I ) FILING DATE: 22-DEC-1987
            ( J ) PUBLICATION DATE: 26-JUL- 1989
            ( K ) RELEVANT RESIDUES IN SEQ ID NO:39: FROM 18 TO 23

( x i ) SEQUENCE DESCRIPTION: SEQ ID NO:39:

```
Xaa  Ser  Asp  Ala  Val  Phe  Thr  Asp  Asn  Tyr  Thr  Lys  Leu  Arg  Lys  Gln
1                   5                        10                       15

Xaa  Ala  Ala  Lys  Lys  Tyr  Leu  Asn  Asp  Leu  Lys  Lys
               20                       25
```

( 2 ) INFORMATION FOR SEQ ID NO:40:

( i ) SEQUENCE CHARACTERISTICS:
            ( A ) LENGTH: 28 amino acids
            ( B ) TYPE: amino acid
            ( D ) TOPOLOGY: both ( i i ) MOLECULE TYPE: peptide ( i i i ) HYPOTHETICAL: NO ( i v ) ANTI-SENSE: NO ( i x ) FEATURE:
            ( A ) NAME/KEY: Modified-site
            ( B ) LOCATION: 21..25
            ( D ) OTHER INFORMATION: /note="Side-chains of amino acids
                    21 and 25 reacted to form cyclic structure"

( i x ) FEATURE:
            ( A ) NAME/KEY: Modified-site
            ( B ) LOCATION: 17
            ( D ) OTHER INFORMATION: /note="Xaa=Nle"

( x ) PUBLICATION INFORMATION:
            ( H ) DOCUMENT NUMBER: EP 325 044 A A
            ( I ) FILING DATE: 22-DEC-1987
            ( J ) PUBLICATION DATE: 26-JUL- 1989
            ( K ) RELEVANT RESIDUES IN SEQ ID NO:40: FROM 18 TO 23

( x i ) SEQUENCE DESCRIPTION: SEQ ID NO:40:

```
His  Ser  Asp  Ala  Val  Phe  Thr  Glu  Asn  Tyr  Thr  Lys  Leu  Arg  Lys  Gln
1                   5                        10                       15

Xaa  Ala  Ala  Lys  Lys  Tyr  Leu  Asn  Asp  Leu  Lys  Lys
               20                       25
```

( 2 ) INFORMATION FOR SEQ ID NO:41:

( i ) SEQUENCE CHARACTERISTICS:
            ( A ) LENGTH: 28 amino acids
            ( B ) TYPE: amino acid
            ( D ) TOPOLOGY: both ( i i ) MOLECULE TYPE: peptide ( i i i ) HYPOTHETICAL: NO ( i v ) ANTI-SENSE: NO ( i x ) FEATURE:
            ( A ) NAME/KEY: Modified-site
            ( B ) LOCATION: 21..25
            ( D ) OTHER INFORMATION: /note="Side-chains of amino acids
                    21 and 25 reacted to form cyclic structure"

( i x ) FEATURE:
            ( A ) NAME/KEY: Modified-site
            ( B ) LOCATION: 17
            ( D ) OTHER INFORMATION: /note="Xaa=Nle"

( i x ) FEATURE:
            ( A ) NAME/KEY: Modified-site
            ( B ) LOCATION: 10

(D) OTHER INFORMATION: /note="Xaa=O-methyl-Tyr"

(x) PUBLICATION INFORMATION:
(H) DOCUMENT NUMBER: EP 325 044 A A
(I) FILING DATE: 22-DEC-1987
(J) PUBLICATION DATE: 26-JUL-1989
(K) RELEVANT RESIDUES IN SEQ ID NO:41: FROM 18 TO 23

(xi) SEQUENCE DESCRIPTION: SEQ ID NO:41:

His Ser Asp Ala Val Phe Thr Asp Asn Xaa Thr Lys Leu Arg Lys Gln
1               5                   10                  15

Xaa Ala Ala Lys Lys Tyr Leu Asn Asp Val Leu Thr
            20                  25

(2) INFORMATION FOR SEQ ID NO:42:

(i) SEQUENCE CHARACTERISTICS:
(A) LENGTH: 31 amino acids
(B) TYPE: amino acid
(D) TOPOLOGY: both (ii) MOLECULE TYPE: peptide (iii) HYPOTHETICAL: NO (iv) ANTI-SENSE: NO (ix) FEATURE:
(A) NAME/KEY: Modified-site
(B) LOCATION: 21..25
(D) OTHER INFORMATION: /note="Side-chains of amino acids
    21 and 25 reacted to form cyclic structure"

(ix) FEATURE:
(A) NAME/KEY: Modified-site
(B) LOCATION: 17
(D) OTHER INFORMATION: /note="Xaa=Nle"

(x) PUBLICATION INFORMATION:
(H) DOCUMENT NUMBER: EP 325 044 A A
(I) FILING DATE: 22-DEC-1987
(J) PUBLICATION DATE: 26-JUL-1989
(K) RELEVANT RESIDUES IN SEQ ID NO:42: FROM 18 TO 23

(xi) SEQUENCE DESCRIPTION: SEQ ID NO:42:

His Ser Asp Ala Val Phe Thr Glu Asn Tyr Thr Lys Leu Arg Lys Gln
1               5                   10                  15

Xaa Ala Ala Lys Lys Tyr Leu Asn Asp Leu Lys Lys Ala Ala Ala
            20                  25                  30

(2) INFORMATION FOR SEQ ID NO:43:

(i) SEQUENCE CHARACTERISTICS:
(A) LENGTH: 31 amino acids
(B) TYPE: amino acid
(D) TOPOLOGY: both (ii) MOLECULE TYPE: peptide (iii) HYPOTHETICAL: NO (iv) ANTI-SENSE: NO (ix) FEATURE:
(A) NAME/KEY: Modified-site
(B) LOCATION: 21..25
(D) OTHER INFORMATION: /note="Side-chains of amino acids
    21 and 25 reacted to form cyclic structure"

(ix) FEATURE:
(A) NAME/KEY: Modified-site
(B) LOCATION: 17
(D) OTHER INFORMATION: /note="Xaa=Nle"

( x ) PUBLICATION INFORMATION:
          ( H ) DOCUMENT NUMBER: EP 325 044 A A
          ( I ) FILING DATE: 22-DEC-1987
          ( J ) PUBLICATION DATE: 26-JUL-1989
          ( K ) RELEVANT RESIDUES IN SEQ ID NO:43: FROM 18 TO 23

( x i ) SEQUENCE DESCRIPTION: SEQ ID NO:43:

```
His Ala Asp Ala Val Phe Thr Glu Asn Tyr Thr Lys Leu Arg Lys Gln
1                5                   10                  15

Xaa Ala Ala Lys Lys Tyr Leu Asn Asp Leu Lys Lys Ala Ala Ala
                20                  25                  30
```

( 2 ) INFORMATION FOR SEQ ID NO:44:

( i ) SEQUENCE CHARACTERISTICS:
          ( A ) LENGTH: 28 amino acids
          ( B ) TYPE: amino acid
          ( D ) TOPOLOGY: both ( i i ) MOLECULE TYPE: peptide ( i i i ) HYPOTHETICAL: NO ( i v ) ANTI-SENSE: NO ( i x ) FEATURE:
          ( A ) NAME/KEY: Modified-site
          ( B ) LOCATION: 21..25
          ( D ) OTHER INFORMATION: /note="Side-chains of amino acids
                21 and 25 reacted to form cyclic structure"

( i x ) FEATURE:
          ( A ) NAME/KEY: Modified-site
          ( B ) LOCATION: 17
          ( D ) OTHER INFORMATION: /note="Xaa=Nle"

( i x ) FEATURE:
          ( A ) NAME/KEY: Modified-site
          ( B ) LOCATION: 1
          ( D ) OTHER INFORMATION: /note="Xaa=N-methyl-Ala"

( x ) PUBLICATION INFORMATION:
          ( H ) DOCUMENT NUMBER: EP 325 044 A A
          ( I ) FILING DATE: 22-DEC-1987
          ( J ) PUBLICATION DATE: 26-JUL-1989
          ( K ) RELEVANT RESIDUES IN SEQ ID NO:44: FROM 18 TO 23

( x i ) SEQUENCE DESCRIPTION: SEQ ID NO:44:

```
Xaa Ser Asp Ala Val Phe Thr Glu Asn Tyr Thr Lys Leu Arg Lys Gln
1                5                   10                  15

Xaa Ala Ala Lys Lys Tyr Leu Asn Asp Leu Lys Lys
                20                  25
```

( 2 ) INFORMATION FOR SEQ ID NO:45:

( i ) SEQUENCE CHARACTERISTICS:
          ( A ) LENGTH: 28 amino acids
          ( B ) TYPE: amino acid
          ( D ) TOPOLOGY: both ( i i ) MOLECULE TYPE: peptide ( i i i ) HYPOTHETICAL: NO ( i v ) ANTI-SENSE: NO ( i x ) FEATURE:
          ( A ) NAME/KEY: Modified-site
          ( B ) LOCATION: 21..25
          ( D ) OTHER INFORMATION: /note="Side-chains of amino acids
                21 and 25 reacted to form cyclic structure"

( i x ) FEATURE:
          ( A ) NAME/KEY: Modified-site ( B ) LOCATION: 17
( D ) OTHER INFORMATION: /note="Xaa=Nle"

( i x ) FEATURE:
( A ) NAME/KEY: Modified-site
( B ) LOCATION: 6
( D ) OTHER INFORMATION: /note="Xaa=p-F-Phe"

( x ) PUBLICATION INFORMATION:
( H ) DOCUMENT NUMBER: EP 325 044 A A
( I ) FILING DATE: 22-DEC-1987
( J ) PUBLICATION DATE: 26-JUL-1989
( K ) RELEVANT RESIDUES IN SEQ ID NO:45: FROM 18 TO 23

( x i ) SEQUENCE DESCRIPTION: SEQ ID NO:45:

His Ser Asp Ala Val Xaa Thr Glu Asn Tyr Thr Lys Leu Arg Lys Gln
1               5                   10                  15
Xaa Ala Ala Lys Lys Tyr Leu Asn Asp Leu Lys Lys
            20                  25

( 2 ) INFORMATION FOR SEQ ID NO:46:

( i ) SEQUENCE CHARACTERISTICS:
( A ) LENGTH: 28 amino acids
( B ) TYPE: amino acid
( D ) TOPOLOGY: both ( i i ) MOLECULE TYPE: peptide ( i i i ) HYPOTHETICAL: NO ( i v ) ANTI-SENSE: NO ( i x ) FEATURE:
( A ) NAME/KEY: Modified-site
( B ) LOCATION: 21..25
( D ) OTHER INFORMATION: /note="Side-chains of amino acids
21 and 25 reacted to form cyclic structure"

( i x ) FEATURE:
( A ) NAME/KEY: Modified-site
( B ) LOCATION: 17
( D ) OTHER INFORMATION: /note="Xaa=Nle"

( i x ) FEATURE:
( A ) NAME/KEY: Modified-site
( B ) LOCATION: 6
( D ) OTHER INFORMATION: /note="Xaa=1-Nal"

( x ) PUBLICATION INFORMATION:
( H ) DOCUMENT NUMBER: EP 325 044 A A
( I ) FILING DATE: 22-DEC-1987
( J ) PUBLICATION DATE: 26-JUL-1989
( K ) RELEVANT RESIDUES IN SEQ ID NO:46: FROM 18 TO 23

( x i ) SEQUENCE DESCRIPTION: SEQ ID NO:46:

His Ser Asp Ala Val Xaa Thr Glu Asn Tyr Thr Lys Leu Arg Lys Gln
1               5                   10                  15
Xaa Ala Ala Lys Lys Tyr Leu Asn Asp Leu Lys Lys
            20                  25

( 2 ) INFORMATION FOR SEQ ID NO:47:

( i ) SEQUENCE CHARACTERISTICS:
( A ) LENGTH: 28 amino acids
( B ) TYPE: amino acid
( D ) TOPOLOGY: both ( i i ) MOLECULE TYPE: peptide ( i i i ) HYPOTHETICAL: NO ( i v ) ANTI-SENSE: NO (ix) FEATURE:
    (A) NAME/KEY: Modified-site
    (B) LOCATION: 21..25
    (D) OTHER INFORMATION: /note="Side-chains of amino acids
        21 and 25 reacted to form cyclic structure"

(ix) FEATURE:
    (A) NAME/KEY: Modified-site
    (B) LOCATION: 17
    (D) OTHER INFORMATION: /note="Xaa=Nle"

(ix) FEATURE:
    (A) NAME/KEY: Modified-site
    (B) LOCATION: 10
    (D) OTHER INFORMATION: /note="Xaa=p-NH2-Phe"

(x) PUBLICATION INFORMATION:
    (H) DOCUMENT NUMBER: EP 325 044 A A
    (I) FILING DATE: 22-DEC-1987
    (J) PUBLICATION DATE: 26-JUL-1989
    (K) RELEVANT RESIDUES IN SEQ ID NO:47: FROM 18 TO 23

(xi) SEQUENCE DESCRIPTION: SEQ ID NO:47:

His Ser Asp Ala Val Phe Thr Glu Asn Xaa Thr Lys Leu Arg Lys Gln
1               5                   10                  15
Xaa Ala Ala Lys Lys Tyr Leu Asn Asp Leu Lys Lys
            20                  25

(2) INFORMATION FOR SEQ ID NO:48:

(i) SEQUENCE CHARACTERISTICS:
        (A) LENGTH: 28 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 21..25
        (D) OTHER INFORMATION: /note="Side-chains of amino acids
            21 and 25 reacted to form cyclic structure"

(ix) FEATURE:
        (A) NAME/KEY: Modified-site
        (B) LOCATION: 17
        (D) OTHER INFORMATION: /note="Xaa=Nle"

(ix) FEATURE:
        (A) NAME/KEY: Modified-site
        (B) LOCATION: 10
        (D) OTHER INFORMATION: /note="Xaa=O-methyl-Tyr"

(x) PUBLICATION INFORMATION:
        (H) DOCUMENT NUMBER: EP 325 044 A A
        (I) FILING DATE: 22-DEC-1987
        (J) PUBLICATION DATE: 26-JUL-1989
        (K) RELEVANT RESIDUES IN SEQ ID NO:48: FROM 18 TO 23

(xi) SEQUENCE DESCRIPTION: SEQ ID NO:48:

His Ser Asp Ala Val Phe Thr Glu Asn Xaa Thr Lys Leu Arg Lys Gln
1               5                   10                  15
Xaa Ala Ala Lys Lys Tyr Leu Asn Asp Leu Lys Lys
            20                  25

(2) INFORMATION FOR SEQ ID NO:49:

(i) SEQUENCE CHARACTERISTICS:
        (A) LENGTH: 28 amino acids
        (B) TYPE: amino acid (D) TOPOLOGY: both (ii) MOLECULE TYPE: peptide (iii) HYPOTHETICAL: NO (iv) ANTI-SENSE: NO (ix) FEATURE:
    (A) NAME/KEY: Modified-site
    (B) LOCATION: 21..25
    (D) OTHER INFORMATION: /note="Side-chains of amino acids
        21 and 25 reacted to form cyclic structure"

(ix) FEATURE:
    (A) NAME/KEY: Modified-site
    (B) LOCATION: 17
    (D) OTHER INFORMATION: /note="Xaa=Nle"

(ix) FEATURE:
    (A) NAME/KEY: Modified-site
    (B) LOCATION: 6
    (D) OTHER INFORMATION: /note="Xaa=p-F-Phe"

(x) PUBLICATION INFORMATION:
    (H) DOCUMENT NUMBER: EP 325 044 A A
    (I) FILING DATE: 22-DEC-1987
    (J) PUBLICATION DATE: 26-JUL-1989
    (K) RELEVANT RESIDUES IN SEQ ID NO:49: FROM 18 TO 23

(xi) SEQUENCE DESCRIPTION: SEQ ID NO:49:

His Ser Asp Ala Val Xaa Thr Asp Asn Tyr Thr Lys Leu Arg Lys Gln
1               5                   10                  15

Xaa Ala Ala Lys Lys Tyr Leu Asn Asp Val Leu Thr
            20                  25

(2) INFORMATION FOR SEQ ID NO:50:

(i) SEQUENCE CHARACTERISTICS:
        (A) LENGTH: 28 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 21..25
        (D) OTHER INFORMATION: /note="Side-chains of amino acids
            21 and 25 reacted to form cyclic structure"

(ix) FEATURE:
        (A) NAME/KEY: Modified-site
        (B) LOCATION: 17
        (D) OTHER INFORMATION: /note="Xaa=Nle"

(ix) FEATURE:
        (A) NAME/KEY: Modified-site
        (B) LOCATION: 6
        (D) OTHER INFORMATION: /note="Xaa=1-Nal"

(x) PUBLICATION INFORMATION:
        (H) DOCUMENT NUMBER: EP 325 044 A A
        (I) FILING DATE: 22-DEC-1987
        (J) PUBLICATION DATE: 26-JUL-1989
        (K) RELEVANT RESIDUES IN SEQ ID NO:50: FROM 18 TO 23

(xi) SEQUENCE DESCRIPTION: SEQ ID NO:50:

His Ser Asp Ala Val Xaa Thr Asp Asn Tyr Thr Lys Leu Arg Lys Gln
1               5                   10                  15

Xaa Ala Ala Lys Lys Tyr Leu Asn Asp Val Leu Thr (2) INFORMATION FOR SEQ ID NO:51:

(i) SEQUENCE CHARACTERISTICS:
        (A) LENGTH: 31 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 21..25
        (D) OTHER INFORMATION: /note="Side-chains of amino acids
            21 and 25 reacted to form cyclic structure"

(ix) FEATURE:
        (A) NAME/KEY: Modified-site
        (B) LOCATION: 17
        (D) OTHER INFORMATION: /note="Xaa=Nle"

(x) PUBLICATION INFORMATION:
        (H) DOCUMENT NUMBER: EP 325 044 A A
        (I) FILING DATE: 22-DEC-1987
        (J) PUBLICATION DATE: 26-JUL-1989
        (K) RELEVANT RESIDUES IN SEQ ID NO:51: FROM 18 TO 23

(xi) SEQUENCE DESCRIPTION: SEQ ID NO:51:

```
His Ala Asp Ala Val Phe Thr Glu Asn Tyr Thr Lys Leu Arg Lys Gln
1               5                   10                  15
Xaa Ala Ala Lys Lys Tyr Leu Asn Asp Leu Lys Lys Gly Gly Thr
            20                  25                  30
```

(2) INFORMATION FOR SEQ ID NO:52:

(i) SEQUENCE CHARACTERISTICS:
        (A) LENGTH: 31 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 21..25
        (D) OTHER INFORMATION: /note="Side-chains of amino acids
            21 and 25 reacted to form cyclic structure"

(ix) FEATURE:
        (A) NAME/KEY: Modified-site
        (B) LOCATION: 17
        (D) OTHER INFORMATION: /note="Xaa=Nle"

(x) PUBLICATION INFORMATION:
        (H) DOCUMENT NUMBER: EP 325 044 A A
        (I) FILING DATE: 22-DEC-1987
        (J) PUBLICATION DATE: 26-JUL-1989
        (K) RELEVANT RESIDUES IN SEQ ID NO:52: FROM 18 TO 23

(xi) SEQUENCE DESCRIPTION: SEQ ID NO:52:

```
His Ser Asp Ala Val Phe Thr Glu Asn Tyr Thr Lys Leu Arg Lys Gln
1               5                   10                  15
Xaa Ala Ala Lys Lys Tyr Leu Asn Asp Leu Lys Lys Gly Gly Thr
            20                  25                  30
```

( 2 ) INFORMATION FOR SEQ ID NO:53:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids
            21 and 25 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:53: FROM 18 TO 23

( x i ) SEQUENCE DESCRIPTION: SEQ ID NO:53:

```
His Ala Asp Ala Val Phe Thr Glu Asn Tyr Thr Lys Leu Arg Lys Gln
 1               5                  10                  15
Xaa Ala Ala Lys Lys Tyr Leu Asn Asp Leu Lys Lys
            20                  25
```

( 2 ) INFORMATION FOR SEQ ID NO:54:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids
            21 and 25 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( i x ) FEATURE:
        ( A ) NAME/KEY: Modified-site
        ( B ) LOCATION: 10
        ( D ) OTHER INFORMATION: /note="Xaa=p-NH2-Phe"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:54: FROM 18 TO 23

( x i ) SEQUENCE DESCRIPTION: SEQ ID NO:54:

```
His Ser Asp Ala Val Phe Thr Asp Asn Xaa Thr Lys Leu Arg Lys Gln
 1               5                  10                  15
```

```
Xaa  Ala  Ala  Lys  Lys  Tyr  Leu  Asn  Asp  Val  Leu  Thr
          20                      25
```

(2) INFORMATION FOR SEQ ID NO:55:

(i) SEQUENCE CHARACTERISTICS:
        (A) LENGTH: 28 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 21..25
        (D) OTHER INFORMATION: /note="Side-chains of amino acids
            21 and 25 reacted to form cyclic structure"

(ix) FEATURE:
        (A) NAME/KEY: Modified-site
        (B) LOCATION: 17
        (D) OTHER INFORMATION: /note="Xaa=Nle"

(ix) FEATURE:
        (A) NAME/KEY: Modified-site
        (B) LOCATION: 22
        (D) OTHER INFORMATION: /note="Xaa=m-OCH3-Tyr"

(x) PUBLICATION INFORMATION:
        (H) DOCUMENT NUMBER: EP 325 044 A A
        (I) FILING DATE: 22-DEC-1987
        (J) PUBLICATION DATE: 26-JUL-1989
        (K) RELEVANT RESIDUES IN SEQ ID NO:55: FROM 18 TO 23

(xi) SEQUENCE DESCRIPTION: SEQ ID NO:55:

```
His  Ser  Asp  Ala  Val  Phe  Thr  Asp  Asn  Tyr  Thr  Lys  Leu  Arg  Lys  Gln
1                   5                        10                           15

Xaa  Ala  Ala  Lys  Lys  Xaa  Leu  Asn  Asp  Val  Leu  Thr
          20                      25
```

(2) INFORMATION FOR SEQ ID NO:56:

(i) SEQUENCE CHARACTERISTICS:
        (A) LENGTH: 28 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 21..25
        (D) OTHER INFORMATION: /note="Side-chains of amino acids
            21 and 25 reacted to form cyclic structure"

(ix) FEATURE:
        (A) NAME/KEY: Modified-site
        (B) LOCATION: 17
        (D) OTHER INFORMATION: /note="Xaa=Nle"

(ix) FEATURE:
        (A) NAME/KEY: Modified-site
        (B) LOCATION: 22
        (D) OTHER INFORMATION: /note="Xaa=m-F-L-Tyr"

(x) PUBLICATION INFORMATION:
        (H) DOCUMENT NUMBER: EP 325 044 A A
        (I) FILING DATE: 22-DEC-1987

(J) PUBLICATION DATE: 26-JUL-1989
(K) RELEVANT RESIDUES IN SEQ ID NO:56: FROM 18 TO 23

(x i) SEQUENCE DESCRIPTION: SEQ ID NO:56:

His Ser Asp Ala Val Phe Thr Asp Asn Tyr Thr Lys Leu Arg Lys Gln
1               5                   10                      15

Xaa Ala Ala Lys Lys Xaa Leu Asn Asp Val Leu Thr
            20              25

(2) INFORMATION FOR SEQ ID NO:57:

(i) SEQUENCE CHARACTERISTICS:
    (A) LENGTH: 28 amino acids
    (B) TYPE: amino acid
    (D) TOPOLOGY: both (ii) MOLECULE TYPE: peptide (iii) HYPOTHETICAL: NO (iv) ANTI-SENSE: NO (ix) FEATURE:
    (A) NAME/KEY: Modified-site
    (B) LOCATION: 21..25
    (D) OTHER INFORMATION: /note="Side-chains of amino acids
        21 and 25 reacted to form cyclic structure"

(ix) FEATURE:
    (A) NAME/KEY: Modified-site
    (B) LOCATION: 17
    (D) OTHER INFORMATION: /note="Xaa=Nle"

(ix) FEATURE:
    (A) NAME/KEY: Modified-site
    (B) LOCATION: 22
    (D) OTHER INFORMATION: /note="Xaa=m-methoxy-Tyr"

(x) PUBLICATION INFORMATION:
    (H) DOCUMENT NUMBER: EP 325 044 A A
    (I) FILING DATE: 22-DEC-1987
    (J) PUBLICATION DATE: 26-JUL-1989
    (K) RELEVANT RESIDUES IN SEQ ID NO:57: FROM 18 TO 23

(x i) SEQUENCE DESCRIPTION: SEQ ID NO:57:

His Ser Asp Ala Val Phe Thr Glu Asn Tyr Thr Lys Leu Arg Lys Gln
1               5                   10                      15

Xaa Ala Ala Lys Lys Xaa Leu Asn Asp Leu Lys Lys
            20              25

(2) INFORMATION FOR SEQ ID NO:58:

(i) SEQUENCE CHARACTERISTICS:
    (A) LENGTH: 28 amino acids
    (B) TYPE: amino acid
    (D) TOPOLOGY: both (ii) MOLECULE TYPE: peptide (iii) HYPOTHETICAL: NO (iv) ANTI-SENSE: NO (ix) FEATURE:
    (A) NAME/KEY: Modified-site
    (B) LOCATION: 21..25
    (D) OTHER INFORMATION: /note="Side-chains of amino acids
        21 and 25 reacted to form cyclic structure"

(ix) FEATURE:
    (A) NAME/KEY: Modified-site
    (B) LOCATION: 17
    (D) OTHER INFORMATION: /note="Xaa=Nle"

( i x ) FEATURE:
    ( A ) NAME/KEY: Modified-site
    ( B ) LOCATION: 22
    ( D ) OTHER INFORMATION: /note="Xaa=m-F-L-Tyr"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL- 1989
    ( K ) RELEVANT RESIDUES IN SEQ ID NO:58: FROM 18 TO 23

( x i ) SEQUENCE DESCRIPTION: SEQ ID NO:58:

```
His  Ser  Asp  Ala  Val  Phe  Thr  Glu  Asn  Tyr  Thr  Lys  Leu  Arg  Lys  Gln
1                  5                       10                            15

Xaa  Ala  Ala  Lys  Lys  Xaa  Leu  Asn  Asp  Leu  Lys  Lys
              20                       25
```

( 2 ) INFORMATION FOR SEQ ID NO:59:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids
            21 and 25 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL- 1989
        ( K ) RELEVANT RESIDUES IN SEQ ID NO:59: FROM 18 TO 23

( x i ) SEQUENCE DESCRIPTION: SEQ ID NO:59:

```
His  Ser  Asp  Ala  Val  Phe  Thr  Ala  Asn  Tyr  Thr  Lys  Leu  Arg  Lys  Gln
1                  5                       10                            15

Xaa  Ala  Ala  Lys  Lys  Tyr  Leu  Ala  Asp  Leu  Lys  Lys
              20                       25
```

( 2 ) INFORMATION FOR SEQ ID NO:60:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids
            21 and 25 reacted to form cyclic structure"

( x ) PUBLICATION INFORMATION:
        ( H ) DOCUMENT NUMBER: EP 325 044 A A (I) FILING DATE: 22-DEC-1987
(J) PUBLICATION DATE: 26-JUL-1989
(K) RELEVANT RESIDUES IN SEQ ID NO:60: FROM 18 TO 23

(xi) SEQUENCE DESCRIPTION: SEQ ID NO:60:

His Ser Asp Ala Val Phe Thr Glu Asn Tyr Thr Lys Leu Arg Lys Ala
1               5                   10                  15

Ala Ala Ala Lys Lys Tyr Leu Asn Asp Leu Lys Lys
            20              25

(2) INFORMATION FOR SEQ ID NO:61:

(i) SEQUENCE CHARACTERISTICS:
    (A) LENGTH: 28 amino acids
    (B) TYPE: amino acid
    (D) TOPOLOGY: both (ii) MOLECULE TYPE: peptide (iii) HYPOTHETICAL: NO (iv) ANTI-SENSE: NO (ix) FEATURE:
    (A) NAME/KEY: Modified-site
    (B) LOCATION: 21..25
    (D) OTHER INFORMATION: /note="Side-chains of amino acids
        21 and 25 reacted to form cyclic structure"

(ix) FEATURE:
    (A) NAME/KEY: Modified-site
    (B) LOCATION: 17
    (D) OTHER INFORMATION: /note="Xaa=Nle"

(x) PUBLICATION INFORMATION:
    (H) DOCUMENT NUMBER: EP 325 044 A A
    (I) FILING DATE: 22-DEC-1987
    (J) PUBLICATION DATE: 26-JUL-1989
    (K) RELEVANT RESIDUES IN SEQ ID NO:61: FROM 18 TO 23

(xi) SEQUENCE DESCRIPTION: SEQ ID NO:61:

His Ser Asp Ala Val Phe Thr Ala Asn Tyr Thr Lys Leu Arg Lys Ala
1               5                   10                  15

Xaa Ala Ala Lys Lys Tyr Leu Ala Asp Leu Lys Lys
            20              25

(2) INFORMATION FOR SEQ ID NO:62:

(i) SEQUENCE CHARACTERISTICS:
    (A) LENGTH: 28 amino acids
    (B) TYPE: amino acid
    (D) TOPOLOGY: both (ii) MOLECULE TYPE: peptide (iii) HYPOTHETICAL: NO (iv) ANTI-SENSE: NO (ix) FEATURE:
    (A) NAME/KEY: Modified-site
    (B) LOCATION: 21..25
    (D) OTHER INFORMATION: /note="Side-chains of amino acids
        21 and 25 reacted to form cyclic structure"

(x) PUBLICATION INFORMATION:
    (H) DOCUMENT NUMBER: EP 325 044 A A
    (I) FILING DATE: 22-DEC-1987
    (J) PUBLICATION DATE: 26-JUL-1989
    (K) RELEVANT RESIDUES IN SEQ ID NO:12: FROM 18 TO 23

(xi) SEQUENCE DESCRIPTION: SEQ ID NO:62:

His Ser Asp Ala Val Phe Thr Ala Asn Tyr Thr Lys Leu Arg Lys Ala

```
         1                5                    10                       15
       Ala  Ala  Ala  Lys  Lys  Tyr  Leu  Ala  Asp  Leu  Lys  Lys
                      20                  25
```

( 2 ) INFORMATION FOR SEQ ID NO:63:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids
            21 and 25 reacted to form cyclic structure"

( i x ) FEATURE:
        ( A ) NAME/KEY: Modified-site
        ( B ) LOCATION: 17
        ( D ) OTHER INFORMATION: /note="Xaa=Nle"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:63: FROM 18 TO 23

( x i ) SEQUENCE DESCRIPTION: SEQ ID NO:63:

```
       His  Ser  Asp  Ala  Val  Phe  Thr  Glu  Asn  Tyr  Thr  Lys  Leu  Arg  Lys  Ala
       1                 5                        10                        15

Xaa  Ala  Ala  Lys  Lys  Tyr  Leu  Asn  Asp  Leu  Lys  Lys
                      20                  25
```

( 2 ) INFORMATION FOR SEQ ID NO:64:

( i ) SEQUENCE CHARACTERISTICS:
        ( A ) LENGTH: 28 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 21..25
        ( D ) OTHER INFORMATION: /note="Side-chains of amino acids
            21 and 25 reacted to form cyclic structure"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:64: FROM 18 TO 23

( x i ) SEQUENCE DESCRIPTION: SEQ ID NO:64:

```
       His  Ser  Asp  Ala  Val  Phe  Thr  Glu  Asn  Tyr  Thr  Lys  Leu  Arg  Lys  Ala
       1                 5                        10                        15

Ala  Ala  Ala  Lys  Lys  Tyr  Leu  Ala  Asp  Leu  Lys  Lys
                      20                  25
```

( 2 ) INFORMATION FOR SEQ ID NO:65:

( i ) SEQUENCE CHARACTERISTICS:
    ( A ) LENGTH: 31 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 21..25
    ( D ) OTHER INFORMATION: /note="Side-chains of amino acids
        21 and 25 reacted to form cyclic structure"

( i x ) FEATURE:
    ( A ) NAME/KEY: Modified-site
    ( B ) LOCATION: 17
    ( D ) OTHER INFORMATION: /note="Xaa=Nle"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:65: FROM 18 TO 23

( x i ) SEQUENCE DESCRIPTION: SEQ ID NO:65:

His Ser Asp Ala Val Phe Thr Glu Asn Tyr Thr Lys Leu Arg Lys Gln
1               5                   10                  15

Xaa Ala Ala Lys Lys Tyr Leu Asn Asp Val Leu Thr Gly Gly Thr
            20                  25                  30

( 2 ) INFORMATION FOR SEQ ID NO:66:

( i ) SEQUENCE CHARACTERISTICS:
    ( A ) LENGTH: 31 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 21..25
    ( D ) OTHER INFORMATION: /note="Side-chains of amino acids
        21 and 25 reacted to form cyclic structure"

( i x ) FEATURE:
    ( A ) NAME/KEY: Modified-site
    ( B ) LOCATION: 6
    ( D ) OTHER INFORMATION: /note="Xaa=p-F-Phe"

( i x ) FEATURE:
    ( A ) NAME/KEY: Modified-site
    ( B ) LOCATION: 17
    ( D ) OTHER INFORMATION: /note="Xaa=Nle"

( x ) PUBLICATION INFORMATION:
    ( H ) DOCUMENT NUMBER: EP 325 044 A A
    ( I ) FILING DATE: 22-DEC-1987
    ( J ) PUBLICATION DATE: 26-JUL-1989
    ( K ) RELEVANT RESIDUES IN SEQ ID NO:66: FROM 18 TO 23

( x i ) SEQUENCE DESCRIPTION: SEQ ID NO:66:

His Ser Asp Ala Val Xaa Thr Glu Asn Tyr Thr Lys Leu Arg Lys Gln
1               5                   10                  15

Xaa Ala Val Lys Lys Tyr Leu Asn Asp Val Leu Thr Gly Gly Thr
            20                  25                  30

( 2 ) INFORMATION FOR SEQ ID NO:67:

( i ) SEQUENCE CHARACTERISTICS:
( A ) LENGTH: 31 amino acids
( B ) TYPE: amino acid
( D ) TOPOLOGY: both ( i i ) MOLECULE TYPE: peptide ( i i i ) HYPOTHETICAL: NO ( i v ) ANTI-SENSE: NO ( i x ) FEATURE:
( A ) NAME/KEY: Modified-site
( B ) LOCATION: 21..25
( D ) OTHER INFORMATION: /note="Side-chains of amino acids
21 and 25 reacted to form cyclic structure"

( i x ) FEATURE:
( A ) NAME/KEY: Modified-site
( B ) LOCATION: 17
( D ) OTHER INFORMATION: /note="Xaa=Nle"

( x ) PUBLICATION INFORMATION:
( H ) DOCUMENT NUMBER: EP 325 044 A A
( I ) FILING DATE: 22-DEC-1987
( J ) PUBLICATION DATE: 26-JUL-1989
( K ) RELEVANT RESIDUES IN SEQ ID NO:67: FROM 18 TO 23

( x i ) SEQUENCE DESCRIPTION: SEQ ID NO:67:

```
His Ala Asp Ala Val Phe Thr Glu Asn Tyr Thr Lys Leu Arg Lys Gln
1               5                   10                  15
Xaa Ala Val Lys Lys Tyr Leu Asn Asp Leu Lys Lys Gly Gly Thr
            20                  25                  30
```

( 2 ) INFORMATION FOR SEQ ID NO:68:

( i ) SEQUENCE CHARACTERISTICS:
( A ) LENGTH: 31 amino acids
( B ) TYPE: amino acid
( D ) TOPOLOGY: both ( i i ) MOLECULE TYPE: peptide ( i i i ) HYPOTHETICAL: NO ( i v ) ANTI-SENSE: NO ( i x ) FEATURE:
( A ) NAME/KEY: Modified-site
( B ) LOCATION: 21..25
( D ) OTHER INFORMATION: /note="Side-chains of amino acids
21 and 25 reacted to form cyclic structure"

( i x ) FEATURE:
( A ) NAME/KEY: Modified-site
( B ) LOCATION: 17
( D ) OTHER INFORMATION: /note="Xaa=Nle"

( x ) PUBLICATION INFORMATION:
( H ) DOCUMENT NUMBER: EP 325 044 A A
( I ) FILING DATE: 22-DEC-1987
( J ) PUBLICATION DATE: 26-JUL-1989
( K ) RELEVANT RESIDUES IN SEQ ID NO:68: FROM 18 TO 23

( x i ) SEQUENCE DESCRIPTION: SEQ ID NO:68:

```
His Ser Asp Ala Val Phe Thr Glu Asn Tyr Thr Lys Leu Arg Lys Gln
1               5                   10                  15
Xaa Ala Val Lys Lys Tyr Leu Asn Asp Leu Lys Lys Gly Gly Thr
            20                  25                  30
```

(2) INFORMATION FOR SEQ ID NO:69:

(i) SEQUENCE CHARACTERISTICS:
        (A) LENGTH: 31 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 21..25
        (D) OTHER INFORMATION: /note="Side-chains of amino acids
            21 and 25 reacted to form cyclic structure"

(ix) FEATURE:
        (A) NAME/KEY: Modified-site
        (B) LOCATION: 17
        (D) OTHER INFORMATION: /note="Xaa=Nle"

(x) PUBLICATION INFORMATION:
        (H) DOCUMENT NUMBER: EP 325 044 A A
        (I) FILING DATE: 22-DEC-1987
        (J) PUBLICATION DATE: 26-JUL-1989
        (K) RELEVANT RESIDUES IN SEQ ID NO:69: FROM 18 TO 23

(xi) SEQUENCE DESCRIPTION: SEQ ID NO:69:

```
His Ser Asp Ala Val Phe Thr Asp Asn Tyr Thr Lys Leu Arg Lys Gln
 1               5                  10                  15
Xaa Ala Ala Lys Lys Tyr Leu Asn Asp Leu Lys Lys Ala Ala Ala
                20                  25                  30
```

(2) INFORMATION FOR SEQ ID NO:70:

(i) SEQUENCE CHARACTERISTICS:
        (A) LENGTH: 28 amino acids
        (B) TYPE: amino acid
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 21..25
        (D) OTHER INFORMATION: /note="Side-chains of amino acids
            21 and 25 reacted to form cyclic structure"

(ix) FEATURE:
        (A) NAME/KEY: Modified-site
        (B) LOCATION: 1
        (D) OTHER INFORMATION: /note="Xaa=His or N-methyl-Ala"

(ix) FEATURE:
        (A) NAME/KEY: Modified-site
        (B) LOCATION: 6
        (D) OTHER INFORMATION: /note="Xaa=an amino acid wherein
            the side-chain is methylcyclohexyl, methyl or
            ethylphenyl wherein the phenyl ring is substituted with
            X1 and X2 independently selected from H, OH, OCH3, F, Cl,
            I, CH3, CF3, NO2, N(CH3)2, NHCOCH3, NHCOC6H5, or C(CH3)3,
            or methylnapthalene (ix) FEATURE:
        (A) NAME/KEY: Modified-site
        (B) LOCATION: 2
        (D) OTHER INFORMATION: /note="Xaa=Ser or Ala"

(ix) FEATURE:
        (A) NAME/KEY: Modified-site ( B ) LOCATION: 8
              ( D ) OTHER INFORMATION: /note="Xaa=Asp, Glu or Ala"

( i x ) FEATURE:
              ( A ) NAME/KEY: Modified-site
              ( B ) LOCATION: 10
              ( D ) OTHER INFORMATION: /note="Xaa=Tyr or same as position
                    6"

( i x ) FEATURE:
              ( A ) NAME/KEY: Modified-site
              ( B ) LOCATION: 17
              ( D ) OTHER INFORMATION: /note="Xaa=Nle"

( i x ) FEATURE:
              ( A ) NAME/KEY: Modified-site
              ( B ) LOCATION: 22
              ( D ) OTHER INFORMATION: /note="Xaa=Tyr or same as position
                    6"

( i x ) FEATURE:
              ( A ) NAME/KEY: Modified-site
              ( B ) LOCATION: 24
              ( D ) OTHER INFORMATION: /note="Xaa=Asn or Ala"

( x ) PUBLICATION INFORMATION:
              ( H ) DOCUMENT NUMBER: EP 325 044 A A
              ( I ) FILING DATE: 22-DEC-1987
              ( J ) PUBLICATION DATE: 26-JUL-1989
              ( K ) RELEVANT RESIDUES IN SEQ ID NO:70: FROM 18 TO 23

( x i ) SEQUENCE DESCRIPTION: SEQ ID NO:70:

Xaa Xaa Asp Ala Val Xaa Thr Xaa Asn Xaa Thr Lys Leu Arg Lys Gln
 1               5                   1 0                   1 5

Xaa Ala Ala Lys Lys Xaa Leu Xaa Asp Leu Lys Lys
              2 0               2 5

( 2 ) INFORMATION FOR SEQ ID NO:71:

( i ) SEQUENCE CHARACTERISTICS:
              ( A ) LENGTH: 28 amino acids
              ( B ) TYPE: amino acid
              ( D ) TOPOLOGY: both ( i i ) MOLECULE TYPE: peptide ( i i i ) HYPOTHETICAL: NO ( i v ) ANTI-SENSE: NO ( i x ) FEATURE:
              ( A ) NAME/KEY: Modified-site
              ( B ) LOCATION: 21..25
              ( D ) OTHER INFORMATION: /note="Side-chains of amino acids
                    21 and 25 reacted to form cyclic structure"

( i x ) FEATURE:
              ( A ) NAME/KEY: Modified-site
              ( B ) LOCATION: 1
              ( D ) OTHER INFORMATION: /note="Xaa=His or N-methyl-Ala"

( i x ) FEATURE:
              ( A ) NAME/KEY: Modified-site
              ( B ) LOCATION: 6
              ( D ) OTHER INFORMATION: /note="Xaa=an amino acid wherein
                    the side- chain is methylcyclohexyl, methyl or
                    ethylphenyl wherein the phenyl ring is substituted with
                    X1 and X2 independently selected from H, OH, OCH3, F, Cl,
                    I, CH3, CF3, NO2, N(CH3)2, NHCOCH3, NHCOC6H5, or C(CH3)3,
                    or methylnapthalene ( i x ) FEATURE:
              ( A ) NAME/KEY: Modified-site
              ( B ) LOCATION: 8
              ( D ) OTHER INFORMATION: /note="Xaa=Asp, Glu or Ala"

( i x ) FEATURE:

(A) NAME/KEY: Modified-site
(B) LOCATION: 10
(D) OTHER INFORMATION: /note="Xaa=Tyr or same as position 6"

(ix) FEATURE:
(A) NAME/KEY: Modified-site
(B) LOCATION: 17
(D) OTHER INFORMATION: /note="Xaa=Nle"

(ix) FEATURE:
(A) NAME/KEY: Modified-site
(B) LOCATION: 22
(D) OTHER INFORMATION: /note="Xaa=Tyr or same as position 6"

(ix) FEATURE:
(A) NAME/KEY: Modified-site
(B) LOCATION: 24
(D) OTHER INFORMATION: /note="Xaa=Asn or Ala"

(x) PUBLICATION INFORMATION:
(H) DOCUMENT NUMBER: EP 325 044 A A
(I) FILING DATE: 22-DEC-1987
(J) PUBLICATION DATE: 26-JUL-1989
(K) RELEVANT RESIDUES IN SEQ ID NO:71: FROM 18 TO 23

(xi) SEQUENCE DESCRIPTION: SEQ ID NO:71:

Xaa Ser Asp Ala Val Xaa Thr Xaa Asn Xaa Thr Lys Leu Arg Lys Gln
1               5                   10                  15

Xaa Ala Ala Lys Lys Xaa Leu Xaa Asp Leu Lys Lys
            20              25

(2) INFORMATION FOR SEQ ID NO:72:

(i) SEQUENCE CHARACTERISTICS:
(A) LENGTH: 28 amino acids
(B) TYPE: amino acid
(D) TOPOLOGY: both (ii) MOLECULE TYPE: peptide (iii) HYPOTHETICAL: NO (iv) ANTI-SENSE: NO (ix) FEATURE:
(A) NAME/KEY: Modified-site
(B) LOCATION: 21..25
(D) OTHER INFORMATION: /note="Side-chains of amino acids 21 and 25 reacted to form cyclic structure"

(ix) FEATURE:
(A) NAME/KEY: Modified-site
(B) LOCATION: 1
(D) OTHER INFORMATION: /note="Xaa=His or N-methyl-Ala"

(ix) FEATURE:
(A) NAME/KEY: Modified-site
(B) LOCATION: 6
(D) OTHER INFORMATION: /note="Xaa=an amino acid wherein the side- chain is methylcyclohexyl, methyl or ethylphenyl wherein the phenyl ring is substituted with X1 and X2 independently selected from H, OH, OCH3, F, Cl, I, CH3, CF3, NO2, N(CH3)2, NHCOCH3, NHCOC6H5, or C(CH3)3, or methylnapthalene"

(ix) FEATURE:
(A) NAME/KEY: Modified-site
(B) LOCATION: 8
(D) OTHER INFORMATION: /note="Xaa=Asp, Glu or Ala"

(ix) FEATURE:
(A) NAME/KEY: Modified-site
(B) LOCATION: 10
(D) OTHER INFORMATION: /note="Xaa=Tyr or same as position 6"

( i x ) FEATURE:
        ( A ) NAME/KEY: Modified-site
        ( B ) LOCATION: 17
        ( D ) OTHER INFORMATION: /note="Xaa=Nle"

( i x ) FEATURE:
        ( A ) NAME/KEY: Modified-site
        ( B ) LOCATION: 22
        ( D ) OTHER INFORMATION: /note="Xaa=Tyr or same as position
              6"

( i x ) FEATURE:
        ( A ) NAME/KEY: Modified-site
        ( B ) LOCATION: 24
        ( D ) OTHER INFORMATION: /note="Xaa=Asn or Ala"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL-1989
        ( K ) RELEVANT RESIDUES IN SEQ ID NO:72: FROM 18 TO 23

( x i ) SEQUENCE DESCRIPTION: SEQ ID NO:72:

Xaa Ala Asp Ala Val Xaa Thr Xaa Asn Xaa Thr Lys Leu Arg Lys Gln
1                5                    10                   15

Xaa Ala Ala Lys Lys Xaa Leu Xaa Asp Leu Lys Lys
    20                   25

( 2 ) INFORMATION FOR SEQ ID NO:73:

( i ) SEQUENCE CHARACTERISTICS:
            ( A ) LENGTH: 28 amino acids
            ( B ) TYPE: amino acid
            ( D ) TOPOLOGY: both ( i i ) MOLECULE TYPE: peptide ( i i i ) HYPOTHETICAL: NO ( i v ) ANTI-SENSE: NO ( i x ) FEATURE:
            ( A ) NAME/KEY: Modified-site
            ( B ) LOCATION: 21..25
            ( D ) OTHER INFORMATION: /note="Side-chains of amino acids
                  21 and 25 reacted to form cyclic structure"

( i x ) FEATURE:
            ( A ) NAME/KEY: Modified-site
            ( B ) LOCATION: 1
            ( D ) OTHER INFORMATION: /note="Xaa=His or N-methyl-Ala"

( i x ) FEATURE:
            ( A ) NAME/KEY: Modified-site
            ( B ) LOCATION: 6
            ( D ) OTHER INFORMATION: /note="Xaa=an amino acid wherein
                  the side- chain is methylcyclohexyl, methyl or
                  ethylphenyl wherein the phenyl ring is substituted with
                  X1 and X2 independently selected from H, OH, OCH3, F, Cl,
                  I, CH3, CF3, NO2, N(CH3)2, NHCOCH3, NHCOC6H5, or C(CH3)3,
                  or methylnapthalene ( i x ) FEATURE:
            ( A ) NAME/KEY: Modified-site
            ( B ) LOCATION: 2
            ( D ) OTHER INFORMATION: /note="Xaa=Ser or Ala"

( i x ) FEATURE:
            ( A ) NAME/KEY: Modified-site
            ( B ) LOCATION: 8
            ( D ) OTHER INFORMATION: /note="Xaa=Asp, Glu or Ala"

( i x ) FEATURE:
            ( A ) NAME/KEY: Modified-site
            ( B ) LOCATION: 10
            ( D ) OTHER INFORMATION: /note="Xaa=Tyr or same as position

```
                                          6"

( i x ) FEATURE:
        ( A ) NAME/KEY: Modified-site
        ( B ) LOCATION: 17
        ( D ) OTHER INFORMATION: /note="Xaa=Nle"

( i x ) FEATURE:
        ( A ) NAME/KEY: Modified-site
        ( B ) LOCATION: 22
        ( D ) OTHER INFORMATION: /note="Xaa=Tyr or same as position
                                        6"

( i x ) FEATURE:
        ( A ) NAME/KEY: Modified-site
        ( B ) LOCATION: 24
        ( D ) OTHER INFORMATION: /note="Xaa=Asn or Ala"

( x ) PUBLICATION INFORMATION:
        ( H ) DOCUMENT NUMBER: EP 325 044 A A
        ( I ) FILING DATE: 22-DEC-1987
        ( J ) PUBLICATION DATE: 26-JUL- 1989
        ( K ) RELEVANT RESIDUES IN SEQ ID NO:73: FROM 18 TO 23

( x i ) SEQUENCE DESCRIPTION: SEQ ID NO:73:

Xaa  Xaa  Asp  Ala  Val  Xaa  Thr  Xaa  Asn  Xaa  Thr  Lys  Leu  Arg  Lys  Ala
 1                   5                        10                         15

Xaa  Ala  Ala  Lys  Lys  Xaa  Leu  Xaa  Asp  Leu  Lys  Lys
          20                        25
```

CYCLIC VASOACTIVE PEPTIDE ANALOGS

This is a continuation of application Ser. No. 08/153,530, filed Nov. 16, 1993, abandoned, which is a continuation of Ser. No. 07/773,747, filed Oct. 11, 1991, now abandoned.

BACKGROUND OF THE INVENTION

Vasoactive intestinal peptide (VIP) was first discovered, isolated and purified from porcine intestine. [U.S. Pat. No. 3,879,371]. The peptide has twenty-eight (28) amino acids and bears extensive homology to secretin and glucagon. [Carlquist et al., Horm. Metab. Res., 14, 28–29 (1982)]. The amino acid sequence of VIP is as follows:

His—Ser—Asp—Ala—Val—Phe—Thr—Asp—Asn—Tyr—Thr—Arg—Leu—Arg—Lys—Gln—Met—Ala—Val—Lys—Lys—Tyr—Leu—Asn—Ser—Ile—Leu—Asn—NH$_2$
[(SEQ ID NO:1)—NH$_2$]

VIP is known to exhibit a wide range of biological activities throughout the gastrointestinal tract and circulatory system. In light of its similarity to gastrointestinal hormones, VIP has been found to stimulate pancreatic and biliary secretion, hepatic glycogenolysis, glucagon and insulin secretion and to activate pancreatic bicarbonate release. [Kerrins, C. and Said, S. I., Proc. Soc. Exp. Biol. Med., 142, 1014–1017 (1972); Domschke, S. et al., Gastroenterology, 73, 478–480 (1977)].

Neurons containing VIP have been localized by immunoassay in cells of the endocrine and exocrine systems, intestine and smooth muscle. [Polak, J. M. et al., Gut, 15, 720–724 (1974)]. VIP has been found to be a neuroeffector causing the release of several hormones including prolactin [Frawley, L. S., et al., Neuroendocrinology, 33, 79–83 (1981)], thyroxine [Ahren, B., et al., Nature, 287, 343–345 (1980)], and insulin and glucagon [Schebalin, M., et al., Am. J. Physiology E., 232, 197–200 (1977)]. VIP has also been found to stimulate renin release from the kidney in vivo and in vitro. [Porter, J. P., et al., Neuroendocrinology, 36, 404–408 (1983)]. VIP has been found to be present in nerves and nerve terminals in the airways of various animal species and man. [Dey, R. D., and Said, S. I., Fed. Proc., 39, 1062 (1980); Said, S. I., et al., Ann. N.Y. Acad. Sci., 221, 103–114 (1974)]. VIP's cardiovascular and bronchopulmonary effects are of interest as VIP has been found to be a powerful vasodilator and potent smooth muscle relaxant, acting on peripheral, pulmonary, and coronary vascular beds. [Said, S. I., et al., Clin. Res., 20, 29 (1972)]. VIP has been found to have a vasodilatory effect on cerebral blood vessels. [Lee, T. J. and Berszin, I., Science, 224, 898–900 (1984)]. In vitro studies have demonstrated that vasoactive intestinal peptide, applied exogenously to cerebral arteries, induced vasodilation, suggesting VIP as a possible transmitter for cerebral vasodilation. [Lee, T. and Saito, A., Science, 224, 898–901 (1984)]. In the eye, VIP has also been shown to be a potent vasodilator [Nilsson, S. F. E. and Bill, A., Acta Physiol. Scand., 121, 385–392 (1984)].

VIP may have regulatory effects on the immune system. O'Dorisio et al. have shown that VIP can modulate the proliferation and migration of lymphocytes. [J. Immunol., 135, 792s–796s (1985)].

Since VIP has been found to relax smooth muscle and it is normally present in airway tissues, as noted above, it has been hypothesized that VIP may be an endogenous mediator of bronchial smooth muscle relaxation. [Dey, R. D. and Said, S. I., Fed. Proc., 39, 1962 (1980)]. It has been shown that tissues from asthmatic patients contain no immunoreactive VIP, as compared to tissue from normal patients. This may be indicative of a loss of VIP or VIPergic nerve fibers associated with the disease of asthma. [Ollerenshaw, S. et al., New England J. Med., 320, 1244–1248 (1989)]. In vitro and in vivo testing have shown VIP to relax tracheal smooth muscle and protect against bronchoconstrictor agents such as histamine and prostaglandin $F_{2\alpha}$. [Wasserman, M. A. et al., in Vasoactive Intestinal Peptide, S. I. Said, ed., Raven Press, New York, 1982, pp 177–184; Said, S. I. et al., Ann. N.Y. Acad. Sci., 221, 103–114 (1974)]. When giving intravenously, VIP has been found to protect against bronchoconstrictor agents such as histamine, prostaglandin $F_{2\alpha}$, leukotrienes, platelet activating factor as well as antigen-induced bronchoconstrictions. [Said, S. I., et al., supra, (1982)]. VIP has also been found to inhibit mucus secretion in human airway tissue in vitro. [Coles, S. J. et al., Am. Rev. Respir. Dis., 124, 531–536 (1981)].

In man, when administered by intravenous infusion to asthmatic patients, VIP has been shown to cause an increase in peak expiratory flow rate and protect against histamine-induced bronchodilation. [Morice, A. H. and Sever, P. S., Peptides, 7, 279–280 (1986); Morice, A. et al., The Lancet, II 1225–1227 (1983)]. The pulmonary effects observed by this intravenous infusion of VIP were, however, accompanied by cardiovascular side-effects, most notably hypotension and tachycardia and also facial flushing. When given in intravenous doses which did not cause cardiovascular effects, VIP failed to alter specific airway conductance. [Palmer, J. B. D., et al., Thorax, 41, 663–666 (1986)]. The lack of activity was explained as being due to the low dose administered and possibly due to rapid degradation of the compound.

When administered by aerosol to humans, native VIP has been only marginally effective in protecting against histamine-induced bronchoconstriction. [Altieri et al., Pharmacologist, 25, 123 (1983)]. VIP was found to have no significant effect on baseline airway parameters but did have a protective effect against histamine-induced bronchoconstriction when given by inhalation to humans. [Barnes, P. J. and Dixon, C. M. S., Am. Rev. Respir. Dis., 130, 162–166 (1984)]. VIP, when given by aerosol, has been reported to display no tachycardia or hypotensive effects in conjunction with the bronchodilation. [Said, S. I. et al., in Vasoactive Intestinal Peptide, S. I. Said, ed., Raven Press, New York, 1928, pp 185–191].

Because of the interesting and potential clinically useful biological activities of VIP, the substance has been the target of several reported synthetic programs with the goal of enhancing one or more of the properties of this molecule. Takeyama et al. have reported a VIP analog having a glutamic acid substituted for aspartic acid at position 8. This compound was found to be less potent than native VIP. [Chem. Pharm. Bull., 28, 2265–2269 (1980)]. Wendlberger et al. have disclosed the preparation of a VIP analog having norleucine substituted at position 17 for methionine. [Peptide, Proc. 16th Eur. Pept. Symp., 290–295 (1980)]. The peptide was found to be equipotent to native VIP for its ability to displace radioiodinated VIP from liver membrane preparations. Watts and Wooton have reported a series of linear and cyclic VIP fragments, containing between six and twelve residues from the native sequence. [Eur. Pat. Nos. 184309 and 325044; U.S. Pat. Nos. 4,737,487 and 4,866,039]. Turner et al. have reported that the fragment VIP(10-28) is an antagonist to VIP. [Peptides, 7, 849–854 (1986)]. The substituted analog [4-Cl-D-Phe$^6$,Leu$^{17}$]-VIP has also been reported to bind to the VIP receptor and antagonize the activity of VIP. [Pandol, S. et al., Gastrointest. Liver Physiol., 13, G553–G557 (1986)]. Gozes et al. have reported that the analog [Lys$^1$,Pro$^2$,Arg$^3$,Arg$^4$,Pro$^5$,Tyr$^6$]-VIP is a competitive inhibitor of VIP binding to its receptor on glial cells. [Endocrinology, 125, 2945–2949 (1989)]. Robberecht et al. have reported several VIP analogs with D-residues substituted in the N-terminus of native VIP. [Peptides, 9, 339–345 (1988)]. All of these analogs bound less tightly to the VIP receptor and showed lower activity than native VIP in c-AMP activation. Tachibana and Ito have reported several VIP analogs of the precursor molecule. [in Peptide Chem., T. Shiba and S. Sakakibara, eds., Prot. Res. Foundation, 1988, pp. 481–486, Jap. Pat. No. 1083012, U.S. Pat. No. 4,822,774]. These compounds were shown to be 1- to 3-fold more potent bronchodilators than VIP and had a 1- to 2-fold higher level of hypotensive activity. Musso et al. have also reported several VIP analogs have substitutions at positions 6–7, 9–13, 15–17, and 19–28. [Biochemistry, 27, 8174–8181 (1988); Eur. Pat. No. 8271141; U.S. Pat. No. 4,835,252]. These compounds were found to be equal to or less potent than native VIP in binding to the VIP receptor and in biological response. Bartfai et al. have reported a series of multiply substituted [Leu$^{17}$]-VIP analogs. [World Pat. No. 8905857].

SUMMARY OF THE INVENTION

The present invention comprises cyclic vasoactive peptide analogs. A cyclic peptide is a peptide wherein the side chain carboxy terminus of one amino acid in the peptide chain is attached covalently to the side chain amino terminus of another amino acid in the peptide chain via the formation of an amide bond. The covalent bonding between the two amino acid residues in the peptide chain yields a ring structure.

The biological activity of cyclic peptides may be substantially different compared to those of the parent linear analogs. Cyclic peptides are conformationally more rigid, possessing more well defined structures. These changes are reflected in the biological profiles of the cyclic peptides. Cyclization of a peptide analog may extend the duration of action of the peptide due to the enhanced rigidity which renders it less susceptible to chemical and enzymatic degradation. Bioavailability of cyclic peptides may be increased due to changes in the physical properties of the peptide as the result of rigidification of the structure. Further, the well defined shape of the cyclic peptide may allow greater specificity for the target receptor than that of linear peptides, thus reducing the propensity for undesirable biological activities concomitant with the desired one.

The present invention comprises novel cyclic peptides of the formula:

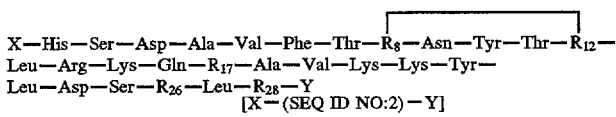

```
X—His—Ser—Asp—Ala—Val—Phe—Thr—R8—Asn—Tyr—Thr—R12—
Leu—Arg—Lys—Gln—R17—Ala—Val—Lys—Lys—Tyr—
Leu—Asp—Ser—R26—Leu—R28—Y
          [X—(SEQ ID NO:2)—Y]
```
I.

wherein $R_8$ is Asp, Glu or Lys; $R_{12}$ is Arg, Lys, Orn or Asp; $R_{17}$ is Met or Nle; $R_{26}$ is Ile or Val; $R_{28}$ is Asn or Thr; X is hydrogen or a hydrolyzable amino protecting group; Y is hydroxyl or a hydrolyzable carboxy protecting group; or pharmaceutically acceptable salts thereof.

Preferred are peptides of the formula:

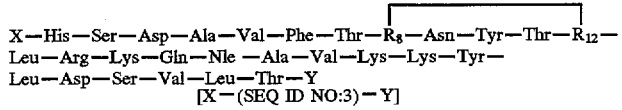

```
X—His—Ser—Asp—Ala—Val—Phe—Thr—R8—Asn—Tyr—Thr—R12—
Leu—Arg—Lys—Gln—Nle—Ala—Val—Lys—Lys—Tyr—
Leu—Asp—Ser—Val—Leu—Thr—Y
          [X—(SEQ ID NO:3)—Y]
``` wherein X, Y, $R_8$ and $R_{12}$ are as above for Formula I.

The present invention also comprises novel cyclic peptides of the formula:

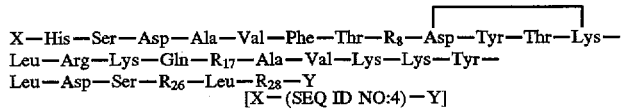

```
X—His—Ser—Asp—Ala—Val—Phe—Thr—R8—Asp—Tyr—Thr—Lys—
Leu—Arg—Lys—Gln—R17—Ala—Val—Lys—Lys—Tyr—
Leu—Asp—Ser—R26—Leu—R28—Y
          [X—(SEQ ID NO:4)—Y]
```
II.

wherein $R_8$ is Asp or Asn; $R_{17}$ is Met or Nle; $R_{26}$ is Ile or Val; $R_{28}$ is Asn or Thr; X is hydrogen or a hydrolyzable amino protecting group; Y is hydroxyl or a hydrolyzable carboxy protecting group; or pharmaceutically acceptable salts thereof.

Preferred is a peptide of the formula:

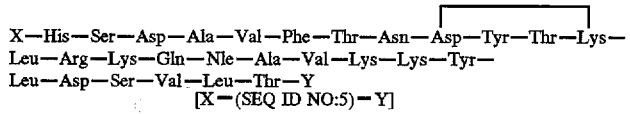

[X—(SEQ ID NO:5)—Y]

wherein X and Y are as above for Formula II.

The present invention also comprises cyclic novel peptides of the formula:

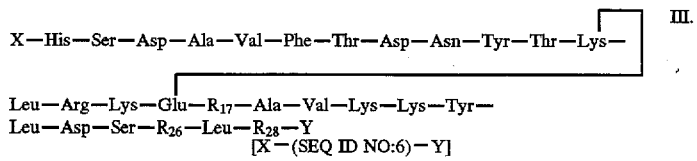 III.

[X—(SEQ ID NO:6)—Y]

wherein $R_{17}$ is Met or Nle; $R_{26}$ is Ile or Val; $R_{28}$ is Asn or Thr; X is hydrogen or a hydrolyzable amino protecting group; Y is hydroxyl or a hydrolyzable carboxy protecting group; or pharmaceutically acceptable salts thereof.

Preferred are peptides of the formula:

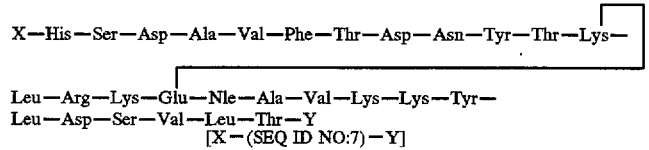

[X—(SEQ ID NO:7)—Y]

wherein X and Y are as above for Formula III.

The present invention also comprises novel cyclic peptides of the formula:

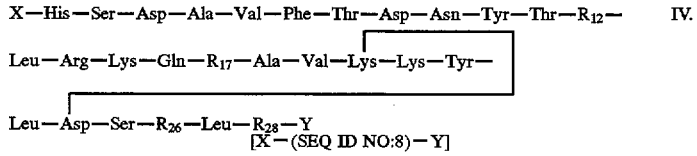 IV.

[X—(SEQ ID NO:8)—Y]

wherein $R_{12}$ is Arg or Lys; $R_{17}$ is Met or Nle; $R_{26}$ is Ile or Val; $R_{28}$ is Asn or Thr; X is hydrogen or a hydroyzable amino protecting group; Y is hydroxyl or a hydrolyzable carboxy protecting group; or pharmaceutically acceptable salts thereof.

Preferred are peptides of the formula:

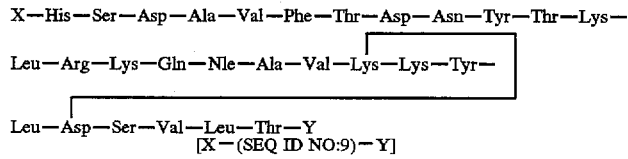

[X—(SEQ ID NO:9)—Y]

wherein X and Y are as above for Formula IV.

The present invention also comprises novel cyclic peptides of the formula:

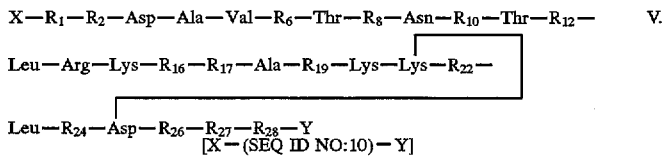

V.

wherein $R_1$ is His, N-CH$_3$-Ala; $R_2$ is Ser or Ala; $R_6$ is

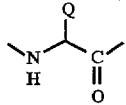

where Q is cyclohexyl lower alkyl or aryl lower alkyl; $R_8$ is Asp, Glu or Ala; $R_{10}$ is Tyr or $R_6$; $R_{12}$ is Arg, Leu, Orn or Lys; $R_{16}$ is Gln or Ala; $R_{17}$ is Met, Nle or Ala; $R_{19}$ is Val or Ala; $R_{22}$ is Tyr or $R_6$; $R_{24}$ is Asn or Ala; $R_{26}$ is Ile, Val, or Leu; $R_{27}$ is Leu or Lys; $R_{28}$ is Asn, Thr, or Lys; X is hydrogen or a hydrolyzable amino protecting group; Y is hydroxyl, a hydrolyzable carboxy protecting group, or $R_{29}$—$R_{30}$—$R_{31}$—Z; $R_{29}$ is Gly or Ala; $R_{30}$ is Gly or Ala; $R_{31}$ is Ala, Met, Cys(Acm), or Thr; Z is hydroxyl or a hydrolyzable carboxy protecting group; or pharmaceutically acceptable salts thereof.

Q is preferably: methyl cyclohexyl, $C_{1-2}$ alkyl phenyl in which the phenyl ring is unsubstituted or substituted with one or more substitutents selected from the group consisting of OH, OCH$_3$, F, Cl, I, CH$_3$, CF$_3$, NO$_2$, NH$_2$, N(CH$_3$)$_2$, NHCOCH$_3$, NHCOC$_6$H$_5$, and C(CH$_3$)$_3$, or $C_{1-2}$ alkyl naphthyl in which the naphthyl rings are unsubstituted or substituted with one or more substituents selected from the group consisting of OH, OCH$_3$, F, Cl, I, CH$_3$, CF$_3$, NO$_2$, NH$_2$, N(CH$_3$)$_2$, NHCOCH$_3$, NHCOC$_6$H$_5$, and C(CH$_3$)$_3$.

More preferably, Q is benzyl, p-fluoro benzyl, p-amino benzyl, p-hydroxy benzyl, p-methoxy-benzyl, 1-methyl naphthyl or 2-methyl napthyl. Q is most preferably benzyl.

Preferred are peptides of the Formulas:

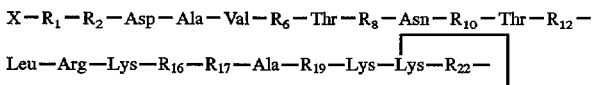

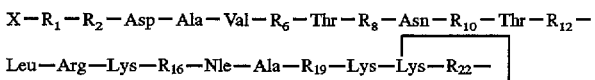

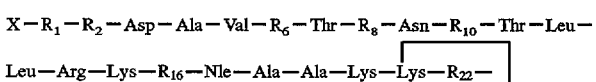

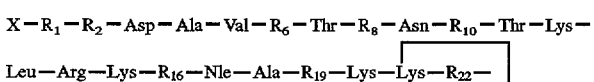

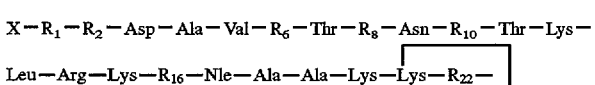

$$X-R_1-R_2-Asp-Ala-Val-R_6-Thr-R_8-Asn-R_{10}-Thr-R_{12}-$$
$$Leu-Arg-Lys-R_{16}-R_{17}-Ala-R_{19}-Lys-Lys-R_{22}-$$
$$Leu-R_{24}-Asp-Leu-Lys-Lys-Y$$
[X—(SEQ ID NO:16)—Y]

$$X-R_1-R_2-Asp-Ala-Val-R_6-Thr-R_8-Asn-R_{10}-Thr-Lys-$$
$$Leu-Arg-Lys-R_{16}-Ala-Ala-Ala-Lys-Lys-R_{22}-$$
$$Leu-R_{24}-Asp-Leu-Lys-Lys-Y$$
[X—(SEQ ID NO:17)—Y]

$$X-R_1-R_2-Asp-Ala-Val-R_6-Thr-R_8-Asn-R_{10}-Thr-Lys-$$
$$Leu-Arg-Lys-R_{16}-Nle-Ala-R_{19}-Lys-Lys-R_{22}-$$
$$Leu-R_{24}-Asp-Leu-Lys-Lys-Y$$
[X—(SEQ ID NO:18)—Y]

$$X-R_1-R_2-Asp-Ala-Val-R_6-Thr-R_8-Asn-R_{10}-Thr-Lys-$$
$$Leu-Arg-Lys-R_{16}-Nle-Ala-Ala-Lys-Lys-R_{22}-$$
$$Leu-R_{24}-Asp-Leu-Lys-Lys-Y$$
[X—(SEQ ID NO:19)—Y]

$$X-R_1-R_2-Asp-Ala-Val-R_6-Thr-R_8-Asn-R_{10}-Thr-Lys-$$
$$Leu-Arg-Lys-Gln-Nle-Ala-Ala-Lys-Lys-R_{22}-$$
$$Leu-R_{24}-Asp-Leu-Lys-Lys-Y$$
[X—(SEQ ID NO:70)—Y]

$$X-R_1-Ser-Asp-Ala-Val-R_6-Thr-R_8-Asn-R_{10}-Thr-Lys-$$
$$Leu-Arg-Lys-Gln-Nle-Ala-Ala-Lys-Lys-R_{22}-$$
$$Leu-R_{24}-Asp-Leu-Lys-Lys-Y$$
[X—(SEQ ID NO:71)—Y]

$$X-R_1-Ala-Asp-Ala-Val-R_6-Thr-R_8-Asn-R_{10}-Thr-Lys-$$
$$Leu-Arg-Lys-Gln-Nle-Ala-Ala-Lys-Lys-R_{22}-$$
$$Leu-R_{24}-Asp-Leu-Lys-Lys-Y$$
[X—(SEQ ID NO:72)—Y]

$$X-R_1-R_2-Asp-Ala-Val-R_6-Thr-R_8-Asn-R_{10}-Thr-Lys-$$
$$Leu-Arg-Lys-Ala-Nle-Ala-Ala-Lys-Lys-R_{22}-$$
$$Leu-R_{24}-Asp-Leu-Lys-Lys-Y$$
[X—(SEQ ID NO:73)—Y]

wherein X, Y, $R_1$, $R_2$, $R_6$, $R_8$, $R_{10}$, $R_{12}$, $R_{16}$, $R_{17}$, $R_{19}$, $R_{22}$, $R_{24}$, and $R_{27}$ are as above for Formula V.

The peptides of the invention produce sustained relaxation of tracheobronchial smooth muscle without cardiovascular side effects and, thus, are useful in the treatment of bronchoconstrictive disorders such as asthma.

DETAILED DESCRIPTION OF THE INVENTION

The present invention relates to novel analogs of vasoactive intestinal peptide (VIP), which have enhanced sustainable bronchodilation activity without observable side effects.

As used herein, the term "lower alkyl" includes straight chain and branched chain saturated aliphatic hydrocarbon groups containing 1–6 carbon atoms. The preferred lower alkyl group is methyl.

As used herein, the term "aryl" signifies mono-nuclear aromatic hydrocarbon groups such as phenyl, which can be unsubstituted or substituted in one or more positions with lower alkyl, lower alkoxy, amino, nitro, hydroxyl, fluoro, chloro, iodo, $CF_3$, mono-or di-lower alkylamino, lower alkyl amido or phenyl amido. "Aryl" also signifies polynuclear aryl groups, such as napthyl, which may be substituted with one or more of the aforementioned moieties. The preferred aryl groups are phenyl, unsubstituted or monosubstituted with fluorine, or unsubstituted naphthyl.

As used herein X is a substituent on the amino nitrogen of the amino-terminal amino acid, and Y is a substituent on the carbonyl group of the carboxy terminal amino acid. X may be hydrogen or a hydroxlyzable amino protecting group. Y may be hydroxyl or a hydrolyzable carboxy protecting group.

With respect to the terms "hydrolyzable amino protecting group" and "hydrolyzable carboxy protecting group", any conventional protecting groups which can be removed by hydrolysis can be utilized in accordance with this invention. Examples of such groups appear hereinafter. Preferred amino protecting groups are

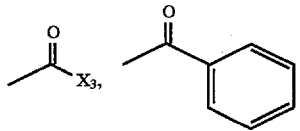

wherein $X_3$ is lower alkyl or halo lower alkyl. Of these protecting groups, those wherein $X_3$ is $C_{1-3}$ alkyl or halo $C_{1-3}$ alkyl are especially preferred.

Preferred carboxy protecting groups are lower alkyl esters, $NH_2$ and lower alkyl amides, with $C_{1-3}$ alkyl esters, $NH_2$ and $C_{1-3}$ alkyl amides being especially preferred.

The present invention comprises novel cyclic peptides of the formula:

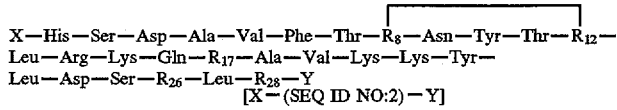

I.

[X−(SEQ ID NO:2)−Y]

wherein $R_8$ is Asp, Glu or Lys; $R_{12}$ is Arg, Lys, Orn or Asp; $R_{17}$ is Met or Nle; $R_{26}$ is Ile or Val; $R_{28}$ is Asn or Thr; X is hydrogen or a hydrolyzable amino protecting group; Y is hydroxyl or a hydrolyzable carboxy protecting group; or pharmaceutically acceptable salts thereof.

Preferred are peptides of the formula:

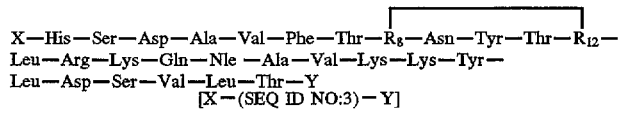

[X−(SEQ ID NO:3)−Y]

wherein X, Y, $R_8$ and $R_{12}$ are as above for Formula I.

The present invention also comprises novel cyclic peptides of the formula:

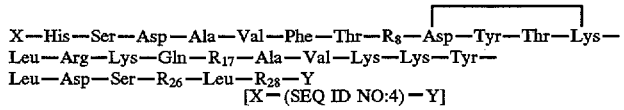

II.

[X−(SEQ ID NO:4)−Y]

wherein $R_8$ is Asp or Asn; $R_{17}$ is Met or Nle; $R_{26}$ is Ile or Val; $R_{28}$ is Asn or Thr; X is hydrogen or a hydrolyzable amino protecting group; Y is hydroxyl or a hydrolyzable carboxy protecting group; or pharmaceutically acceptable salts thereof.

Preferred is a peptide of the formula:

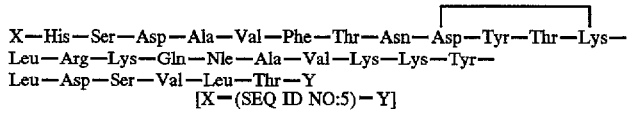

[X—(SEQ ID NO:5)—Y]

wherein X and Y are as above for Formula II.

The present invention also comprises cyclic novel peptides of the formula:

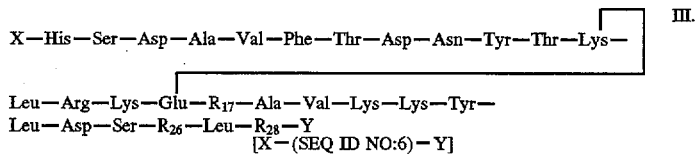

[X—(SEQ ID NO:6)—Y]

wherein $R_{17}$ is Met or Nle; $R_{26}$ is Ile or Val; $R_{28}$ is Asn or Thr; X is hydrogen or a hydrolyzable amino protecting group; Y is hydroxyl or a hydrolyzable carboxy protecting group; or pharmaceutically acceptable salts thereof.

Preferred are peptides of the formula:

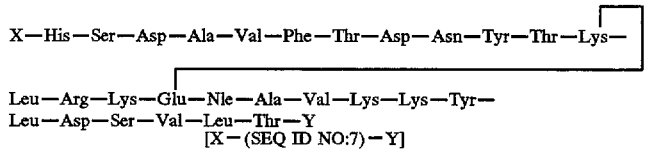

[X—(SEQ ID NO:7)—Y]

wherein X and Y are as above for Formula III.

The present invention also comprises novel cyclic peptides of the formula:

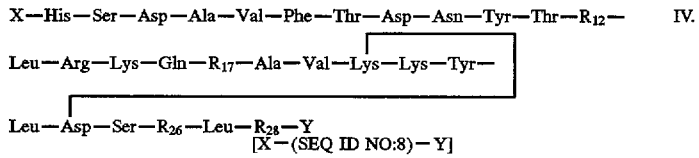

[X—(SEQ ID NO:8)—Y]

wherein $R_{12}$ is Arg or Lys; $R_{17}$ is Met or Nle; $R_{26}$ is Ile or Val; $R_{28}$ is Asn or Thr; X is hydrogen or a hydroyzable amino protecting group; Y is hydroxyl or a hydrolyzable carboxy protecting group; or pharmaceutically acceptable salts thereof.

Preferred are peptides of the formula:

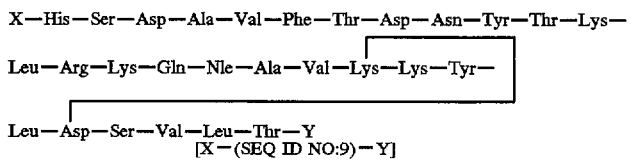

[X—(SEQ ID NO:9)—Y]

wherein X and Y are as above for Formula IV.

The present invention also comprises novel cyclic peptides of the formula:

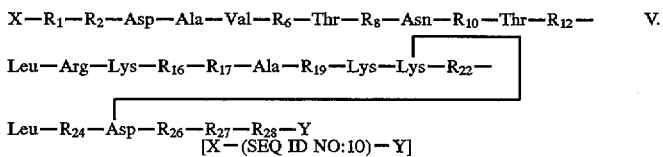 V.

[X—(SEQ ID NO:10)—Y]

wherein $R_1$ is His, N-CH$_3$-Ala; $R_2$ is Ser or Ala; $R_6$ is

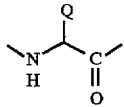

where Q is cyclohexyl lower alkyl or aryl lower alkyl;

$R_8$ is Asp, Glu or Ala; $R_{10}$ is Tyr or $R_6$; $R_{12}$ is Arg or Lys; $R_{16}$ is Gln or Ala; $R_{17}$ is Met, Nle or Ala; $R_{19}$ is Val or Ala; $R_{22}$ is Tyr or $R_6$; $R_{24}$ is Asn or Ala; $R_{26}$ is Ile, Val, or Leu; $R_{27}$ is Leu or Lys; $R_{28}$ is Asn, Thr, or Lys; X is hydrogen or a hydrolyzable amino protecting group; Y is hydroxyl, a hydrolyzable carboxy protecting group, or $R_{29}$—$R_{30}$—$R_{31}$—Z; $R_{29}$ is Gly or Ala; $R_{30}$ is Gly or Ala; $R_{31}$ is Ala, Met, Cys(Acm), or Thr; Z is hydroxyl or a hydrolyzable carboxy protecting group; or pharmaceutically acceptable salts thereof.

Q is preferably: methyl cyclohexyl, $C_{1-2}$ alkyl phenyl in which the phenyl ring is unsubstituted or substituted with one or more substitutents selected from the group consisting of OH, OCH$_3$, F, Cl, I, CH$_3$, CF$_3$, NO$_2$, NH$_2$, N(CH$_3$)$_2$, NHCOCH$_3$, NHCOC$_6$H$_5$, and C(CH$_3$)$_3$, or $C_{1-2}$ alkyl naphthyl in which the naphthyl rings are unsubstituted or substituted with one or more substituents selected from the group consisting of OH, OCH$_3$, F, Cl, I, CH$_3$, CF$_3$, NO$_2$, NH$_2$, N(CH$_3$)$_2$, NHCOCH$_3$, NHCOC$_6$H$_5$, and C(CH$_3$)$_3$.

More preferably, Q is benzyl, p-fluoro benzyl, p-amino benzyl, p-hydroxy benzyl, p-methoxy-benzyl, 1-methyl naphthyl or 2-methyl napthyl. Q is most preferably benzyl.

Preferred are peptides of the Formulas:

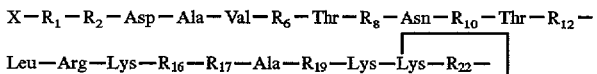

[X—(SEQ ID NO:11)—Y]

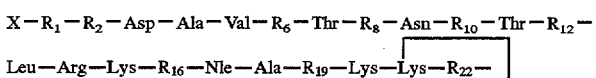

[X—(SEQ ID NO:12)—Y]

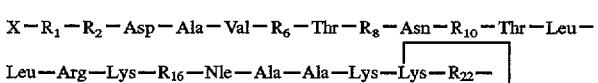

[X—(SEQ ID NO:13)—Y]

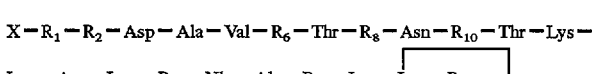

[X—(SEQ ID NO:14)—Y]

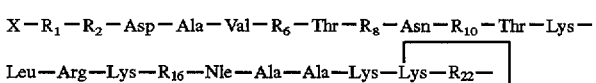

[X—(SEQ ID NO:15)—Y]

-continued

X—R$_1$—R$_2$—Asp—Ala—Val—R$_6$—Thr—R$_8$—Asn—R$_{10}$—Thr—R$_{12}$—
Leu—Arg—Lys—R$_{16}$—R$_{17}$—Ala—R$_{19}$—Lys—Lys—R$_{22}$—

Leu—R$_{24}$—Asp—Leu—Lys—Lys—Y

[X—(SEQ ID NO:16)—Y]

X—R$_1$—R$_2$—Asp—Ala—Val—R$_6$—Thr—R$_8$—Asn—R$_{10}$—Thr—Lys—
Leu—Arg—Lys—R$_{16}$—Ala—Ala—Ala—Lys—Lys—R$_{22}$—

Leu—R$_{24}$—Asp—Leu—Lys—Lys—Y

[X—(SEQ ID NO:17)—Y]

X—R$_1$—R$_2$—Asp—Ala—Val—R$_6$—Thr—R$_8$—Asn—R$_{10}$—Thr—Lys—
Leu—Arg—Lys—R$_{16}$—Nle—Ala—R$_{19}$—Lys—Lys—R$_{22}$—

Leu—R$_{24}$—Asp—Leu—Lys—Lys—Y

[X—(SEQ ID NO:18)—Y]

X—R$_1$—R$_2$—Asp—Ala—Val—R$_6$—Thr—R$_8$—Asn—R$_{10}$—Thr—Lys—
Leu—Arg—Lys—R$_{16}$—Nle—Ala—Ala—Lys—Lys—R$_{22}$—

Leu—R$_{24}$—Asp—Leu—Lys—Lys—Y

[X—(SEQ ID NO:19)—Y]

X—R$_1$—R$_2$—Asp—Ala—Val—R$_6$—Thr—R$_8$—Asn—R$_{10}$—Thr—Lys—
Leu—Arg—Lys—Gln—Nle—Ala—Ala—Lys—Lys—R$_{22}$—

Leu—R$_{24}$—Asp—Leu—Lys—Lys—Y

[X—(SEQ ID NO:70)—Y]

X—R$_1$—Ser—Asp—Ala—Val—R$_6$—Thr—R$_8$—Asn—R$_{10}$—Thr—Lys—
Leu—Arg—Lys—Gln—Nle—Ala—Ala—Lys—Lys—R$_{22}$—

Leu—R$_{24}$—Asp—Leu—Lys—Lys—Y

[X—(SEQ ID NO:71)—Y]

X—R$_1$—Ala—Asp—Ala—Val—R$_6$—Thr—R$_8$—Asn—R$_{10}$—Thr—Lys—
Leu—Arg—Lys—Gln—Nle—Ala—Ala—Lys—Lys—R$_{22}$—

Leu—R$_{24}$—Asp—Leu—Lys—Lys—Y

[X—(SEQ ID NO:72)—Y]

X—R$_1$—R$_2$—Asp—Ala—Val—R$_6$—Thr—R$_8$—Asn—R$_{10}$—Thr—Lys—
Leu—Arg—Lys—Ala—Nle—Ala—Ala—Lys—Lys—R$_{22}$—

Leu—R$_{24}$—Asp—Leu—Lys—Lys—Y

[X—(SEQ ID NO:73)—Y]

wherein X, Y, $R_1$, $R_2$, $R_6$, $R_8$, $R_{10}$, $R_{12}$, $R_{16}$, $R_{17}$, $R_{19}$, $R_{22}$, $R_{24}$, and $R_{27}$ are as above for Formula V.

The invention is further directed to compositions containing such peptides as well as to methods of using such peptides for treating bronchotracheal constrictive disorders.

The nomenclature used to define the peptides is that typically used in the art wherein the amino group at the N-terminus appears to the left and the carboxyl group at the C-terminus appears to the right. By natural amino acids is meant one of the naturally occurring amino acids found in proteins, i.e., Gly, Ala, Val, Leu, Ile, Ser, Thr, Lys, Arg, Asp, Asn, Glu, Gln, Cys, Met, Phe, Tyr, Pro, Trp, and His. Where the amino acid has isomeric forms, it is the L form of the amino acid that is represented unless otherwise expressly indicated.

The following abbreviations or symbols are used to represent amino acids in addition to those described above, protecting groups, solvents, reagents and the like.

| Symbol | Meaning |
|---|---|
| Ac | Acetyl |
| Orn | Ornithine |
| Nle | Norleucine |
| Fmoc | 9-Fluorenylmethyloxycarbonyl |
| Fm | 9-Fluorenylmethyl |
| Boc | t-Butyloxycarbonyl |
| Bom | Benzyloxymethyl |
| CH2Cl2 | Methylene chloride |
| CH3CN | Acetonitrile |
| DMF | Dimethylformamide |
| DIPEA | N,N-Diisopropylethylamine |
| TFA | Trifluoroacetic acid |
| HOBT | N-Hydroxybenzotriazole |
| DCC | N,N'-Dicyclohexylcarbodiimide |
| DIC | N,N'-Diisopropylcarbodiimide |
| BOP | Benzotriazol-1-yloxy-tri-(dimethylamino)phosphonium hexafluorophosphate |
| N—Me—Ala | 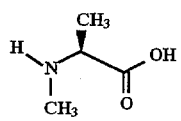 |
| 2-Nal | 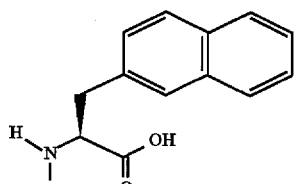 |
| p-F—Phe | 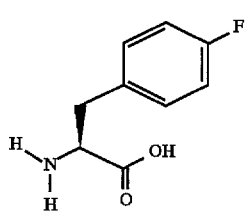 |
| FAB-MS | Fast atom bombardment mass spectrometry |

Analogs of the native VIP peptide sequence are indicated by setting forth the substituted amino acid in brackets before "VIP". Derivatization of the N-terminal amino group, i.e. as by X above, is indicated to the left of the bracketed substitutions. Sequence numbers appearing in parentheses to the right of "VIP" indicate amino acid deletions and additions to the native sequence numbering. That is, for example, Ac-[$Lys^{12}$,$Nle^{17}$,$Gly^{29}$]-VIP(1-29)-$NH_2$ indicates a polypeptide having an amino acid sequence corresponding to native human VIP in which an acetyl group has been substituted for hydrogen at the N-terminus, a lysine has been substituted for arginine at position 12 and a norleucine has been substituted for methionine at position 17. Additionally, a glycine has been coupled onto the carboxyl site of asparagine 28, termed position 29. The suffixes "-OH" and "-$NH_2$" following "VIP" or the parentheses refer to the free acid and amide forms of the polypeptide, respectively. In the event neither suffix is used, the expression is intended to encompass both forms.

As stated above, a cyclic peptide, as defined herein, is a peptide wherein the side chain carboxy terminus of one amino acid in the peptide is attached covalently to the side chain amino terminus of another amino acid in the peptide chain via formation of an amide bond. Several nomenclatures and symbols are utilized to represent a cyclic peptide. The following are examples:

Ac—His—Ser—Asp—Ala—Val—Phe—Thr—Asp—Asn—Tyr—Thr—Lys—Leu—Arg—Lys—Gln—Nle—Ala—Val—Lys—Lys—Tyr—Leu—Asp—Ser—Val—Leu—Thr—$NH_2$.    a

[Ac—(SEQ ID NO:20)—$NH_2$]

-continued

Ac—[Lys¹², Nle¹⁷, Val²⁶, Thr²⁸]-VIP cyclo (8 ⟶ 12).  b

[Ac—(SEQ ID NO:20)—NH₂]

Ac—[Lys¹², Nle¹⁷, Val²⁶, Thr²⁸]-VIP cyclo (Asp⁸ ⟶ Lys¹²).  c

[Ac—(SEQ ID NO:20)—NH₂]

The above three structures (a–c), and the accompanying representation using the SEQ ID NO: and the Sequence Listing below, each represent and define the same polypeptide having an amino acid sequence corresponding to native human VIP in which an acetyl group has been substituted for hydrogen at the N-terminus, a lysine has been substituted for arginine at position 12, a norleucine has been substituted for methionine at position 17, a valine has been substituted for isoleucine at position 26, and a threonine has been substituted at position 28 for asparagine. Additionally, an amide bond has been formed between the side chain carboxyl of the aspartic acid at position 8 and the side chain amine of the lysine at position 12, thus forming the cyclic peptide analog. The above representations for the peptide structure are considered to be equivalent and interchangeable.

As used herein, the terms "$R_n$" for an amino acid at position n in one of the structures shown herein and "Xaa" for an amino acid at position n in the corresponding sequence in the Sequence Listing below are equivalent and interchangeable in those instances where Xaa represents a selection from among two or more amino acids.

In the cyclic peptides of the present invention, the following configurations apply unless otherwise stated.

| Amino Acid in chain | Terminus of amino acid bound to make cyclic peptide |
|---|---|
| Lys | ε amino ε |
| Orn | δ amino (= δ delta) |
| Asp | β carboxyl (β = beta) |
| Glu | γ carboxyl (γ = gamma) |

Representative compounds of the present invention include peptides having the following amino acid sequences:

Ac-[Lys¹²,Nle¹⁷,Val²⁶,Thr²⁸]-VIP cyclo (Asp⁸→Lys¹²) [Ac-(SEQ ID NO:20)-NH₂]
Ac-[Glu⁸,Lys¹²,Nle¹⁷,Val²⁶,Thr²⁸]-VIP cyclo (Glu⁸→Lys¹²) [Ac-(SEQ ID NO:21)-NH₂]
Ac-[Asn⁸,Asp⁹,Lys¹²,Nle¹⁷,Val²⁶,Thr²⁸]-VIP cyclo (Asp⁹→Lys¹²) [Ac-(SEQ ID NO:22)-NH₂]
Ac-[Orn¹²,Nle¹⁷,Val²⁶,Thr²⁸]-VIP cyclo (Asp⁸→Orn¹²) [Ac-(SEQ ID NO:23)-NH₂]
Ac-[Lys⁸,Asp¹²,Nle¹⁷,Val²⁶,Thr²⁸]-VIP cyclo (Lys⁸→Asp¹²) [Ac-(SEQ ID NO:24)-NH₂]
Ac-[Glu⁸,Orn¹²,Nle¹⁷,Val²⁶,Thr²⁸]-VIP cyclo (Glu⁸→Orn¹²) [Ac-(SEQ ID NO:25)-NH₂]
Ac-[Lys¹²,Glu¹⁶,Nle¹⁷,Val²⁶,Thr²⁸]-VIP cyclo (Lys¹²→Glu¹⁶) [Ac-(SEQ ID NO:26)-NH₂]
Ac-[Lys¹²,Nle¹⁷,Asp²⁴,Val²⁶,Thr²⁸]-VIP cyclo (Lys²⁰→Asp²⁴) [Ac-(SEQ ID NO:27)-NH₂]
Ac-[Lys¹²,Nle¹⁷,Asp²⁵,Val²⁶,Thr²⁸]-VIP cyclo (Lys²¹→Asp²⁵) [Ac-(SEQ ID NO:28)-NH₂]
Ac-[Lys¹²,Nle¹⁷,Ala¹⁹,Asp²⁵,Val²⁶,Thr²⁸]-VIP cyclo (Lys²¹→Asp²⁵) [Ac-(SEQ ID NO:29)-NH₂]
Ac-[p-F-Phe⁶,2-Nal¹⁰,Lys¹²,Nle¹⁷,Asp²⁵,Val²⁶,Thr²⁸,Gly²⁹,³⁰,Met³¹]-VIP cyclo (Lys²¹→Asp²⁵) [Ac-(SEQ ID NO:30)-NH₂]
Ac-[Glu⁸,Orn¹²,Nle¹⁷,Asp²⁵,Val²⁶,Thr²⁸]-VIP cyclo (Lys²¹→Asp²⁵) [Ac-(SEQ ID NO:31)-NH₂]
Ac-[p-F-Phe⁶,Lys¹²,Nle¹⁷,Ala¹⁹,Asp²⁵,Val²⁶,Thr²⁸,Gly²⁹,³⁰,Cys(Acm)³¹]-VIP cyclo (Lys²¹→Asp²⁵) [Ac-(SEQ ID NO:32)-NH₂]
Ac-[Ala²,Lys¹²,Nle¹⁷,Ala¹⁹,Asp²⁵,Val²⁶,Thr²⁸]-VIP cyclo (Lys²¹→Asp²⁵) [Ac-(SEQ ID NO:33)-NH₂]
Ac-[N-Me-Ala¹,Lys¹²,Nle¹⁷,Ala¹⁹,Asp²⁵,Val²⁶,Thr²⁸]-VIP cyclo(Lys²¹→Asp²⁵) [Ac-(SEQ ID NO:34)-NH₂]
Ac-[2-Nal¹⁰,Leu¹²,Nle¹⁷,Ala¹⁹,Asp²⁵,Val²⁶,Thr²⁸]-VIP cyclo (Lys²¹→Asp²⁵) [Ac-(SEQ ID NO:35)-NH₂]
Ac-[O-CH₃-Tyr¹⁰,Leu¹²,Nle¹⁷,Ala¹⁹,Asp²⁵,Val²⁶,Thr²⁸]-VIP cyclo (Lys²¹→Asp²⁵) [Ac-(SEQ ID NO:36)-NH₂]
Ac-[p-F-Phe⁶,p-NH₂-Phe¹⁰,Leu¹²,Nle¹⁷,Ala¹⁹,Asp²⁵,Val²⁶,Thr²⁸]-VIP cyclo (Lys²¹→Asp²⁵) [Ac-(SEQ ID NO:37)-NH₂]
Ac-[Lys¹²,Nle¹⁷,Ala¹⁹,Asp²⁵,Leu²⁶,Lys²⁷,²⁸]-VIP cyclo (Lys²¹→Asp²⁵) [Ac-(SEQ ID NO:38)-NH₂]
Ac-[N-Me-Ala¹,Lys¹²,Nle¹⁷,Ala¹⁹,Asp²⁵,Leu²⁶,Lys²⁷,²⁸]-VIP cyclo (Lys²¹→Asp²⁵) [Ac-(SEQ ID NO:39)-NH₂]
Ac-[Glu⁸,Lys¹²,Nle¹⁷,Ala¹⁹,Asp²⁵,Leu²⁶,Lys²⁷,²⁸]-VIP cyclo (Lys²¹→Asp²⁵) [Ac-(SEQ ID NO:40)-NH₂]
Ac-[O-Me-Tyr¹⁰,Lys¹²,Nle¹⁷,Ala¹⁹,Asp²⁵,Val²⁶,Thr²⁸]-VIP cyclo (Lys²¹→Asp²⁵) [Ac-(SEQ ID NO:41)-NH₂]
Ac-[Glu⁸,Lys¹²,Nle¹⁷,Ala¹⁹,Asp²⁵,Leu²⁶,Lys²⁷,²⁸,Ala²⁹⁻³¹]-VIP cyclo (Lys²¹→Asp²⁵) [Ac-(SEQ ID NO:42)-NH₂]
Ac-[Ala²,Glu⁸,Lys¹²,Nle¹⁷,Ala¹⁹,Asp²⁵,Leu²⁶,Lys²⁷,²⁸,Ala²⁹⁻³¹]-VIP cyclo (Lys²¹→Asp²⁵) [Ac-(SEQ ID NO:43)-NH₂]
Ac-[N-Me-Ala¹,Glu⁸,Lys¹²,Nle¹⁷,Ala¹⁹,Asp²⁵,Leu²⁶,Lys²⁷,²⁸]-VIP cyclo (Lys²¹→Asp²⁵) [Ac-(SEQ ID NO:44)-NH₂]
Ac-[p-F-Phe⁶,Glu⁸,Lys¹²,Nle¹⁷,Ala¹⁹,Asp²⁵,Leu²⁶,Lys²⁷,²⁸]-VIP cyclo (Lys²¹→Asp²⁵) [Ac-(SEQ ID NO:45)-NH₂]
Ac-[1-Nal⁶,Glu⁸,Lys¹²,Nle¹⁷,Ala¹⁹,Asp²⁵,Leu²⁶,Lys²⁷,²⁸]-VIP cyclo (Lys²¹→Asp²⁵) [Ac-(SEQ ID NO:46)-NH₂]
Ac-[Glu⁸,p-NH₂-Phe¹⁰,Lys¹²,Nle¹⁷,Ala¹⁹,Asp²⁵,Leu²⁶,Lys²⁷,²⁸]-VIP cyclo (Lys²¹→Asp²⁵) [Ac-(SEQ ID NO:47)-NH₂]
Ac-[Glu⁸,O-CH₃-Tyr¹⁰,Lys¹²,Nle¹⁷,Ala¹⁹,Asp²⁵,Leu²⁶,Lys²⁷,²⁸]-VIP cyclo (Lys²¹→Asp²⁵) [Ac-(SEQ ID NO:48)-NH₂]
Ac-[p-F-Phe⁶,Lys¹²,Nle¹⁷,Ala¹⁹,Asp²⁵,Val²⁶,Thr²⁸]-VIP cyclo (Lys²¹→Asp²⁵) [Ac-(SEQ ID NO:49)-NH₂] Ac-[1-Nal¹⁶,Lys¹²,Nle¹⁷,Ala¹⁹,Asp²⁵,Val²⁶,Thr²⁸]-VIP cyclo (Lys²¹→Asp²⁵) [Ac-(SEQ ID NO:50)-NH₂]
Ac-[Ala²,Glu⁸,Lys¹²,Nle¹⁷,Ala¹⁹,Asp²⁵,Leu²⁶,Lys²⁷,²⁸,Gly²⁹,³⁰,Thr³¹]-VIP cyclo (Lys²¹→Asp²⁵) [Ac-(SEQ ID NO:51)-NH₂]
Ac-[Glu⁸,Lys¹²,Nle¹⁷,Ala¹⁹,Asp²⁵,Leu²⁶,Lys²⁷,²⁸,Gly²⁹,³⁰,Thr³¹]-VIP cyclo (Lys²¹→Asp²⁵) [Ac-(SEQ ID NO:52)-NH₂]
Ac-[Ala²,Glu⁸,Lys¹²,Nle¹⁷,Ala¹⁹,Asp²⁵,Leu²⁶,Lys²⁷,²⁸]-VIP cyclo (Lys²¹→Asp²⁵) [Ac-(SEQ ID NO:53)-NH₂]
Ac-[p-NH₂-Phe¹⁰,Lys¹²,Nle¹⁷,Ala¹⁹,Asp²⁵,Val²⁶,Thr²⁸]-VIP cyclo (Lys²¹→Asp²⁵) [Ac-(SEQ ID NO:54)-NH₂]
Ac-[Lys¹²,Nle¹⁷,Ala¹⁹,m-OCH₃-Tyr²²,Asp²⁵,Val²⁶,Thr²⁸]-VIP cyclo (Lys²¹→Asp²⁵) [Ac-(SEQ ID NO:55)-NH₂]
Ac-[Lys¹²,Nle¹⁷,Ala¹⁹,m-F-L-Tyr²²,Asp²⁵,Val²⁶,Thr²⁸]-VIP cyclo (Lys²¹→Asp²⁵) [Ac-(SEQ ID NO:56)-NH₂]

Ac-[Glu$^8$,Lys$^{12}$,Nle$^{17}$,Ala$^{19}$,m-OCH$_3$-Tyr$^{22}$,Asp$^{25}$,Leu$^{26}$, Lys$^{27,28}$]-VIP cyclo (Lys$^{21}$→Asp$^{25}$) [Ac-(SEQ ID NO:57)-NH$_2$]

Ac-[Glu$^8$,Lys$^{12}$,Nle$^{17}$,Ala$^{19}$,m-F-L-Tyr$^{22}$,Asp$^{25}$,Leu$^{26}$, Lys$^{27,28}$]-VIP cyclo (Lys$^{21}$→Asp$^{25}$) [Ac-(SEQ ID NO:58)-NH$_2$]

Ac-[Ala$^8$,Lys$^{12}$,Nle$^{17}$,Ala$^{19}$,Ala$^{24}$,Asp$^{25}$,Leu$^{26}$,Lys$^{27,28}$]-VIP cyclo (Lys$^{21}$→Asp$^{25}$) [Ac-(SEQ ID NO:59)-NH$_2$]

Ac-[Glu$^8$,Lys$^{12}$,Ala$^{16,17,19}$,Asp$^{25}$,Leu$^{26}$,Lys$^{27,28}$]-VIP cyclo (Lys$^{21}$→Asp$^{25}$) [Ac-(SEQ ID NO:60)-NH$_2$]

Ac-[Ala$^8$,Lys$^{12}$,Ala$^{16}$,Nle$^{17}$,Ala$^{19}$,Ala$^{24}$,Asp$^{25}$,Leu$^{26}$,Lys$^{27,28}$]-VIP cyclo (Lys$^{21}$→Asp$^{25}$) [Ac-(SEQ ID NO:61)-NH$_2$]

Ac-[Ala$^8$,Lys$^{12}$,Ala$^{16,17,19}$,Ala$^{24}$,Asp$^{25}$,Leu$^{26}$,Lys$^{27,28}$]-VIP cyclo (Lys$^{21}$→Asp$^{25}$) [Ac-(SEQ ID NO:62)-NH$_2$]

Ac-[Glu$^8$,Lys$^{12}$,Ala$^{16}$,Nle$^{17}$,Ala$^{19}$,Asp$^{25}$,Leu$^{26}$,Lys$^{27,28}$]-VIP cyclo (Lys$^{21}$→Asp$^{25}$) [Ac-(SEQ ID NO:63)-NH$_2$]

Ac-[Glu$^8$,Lys$^{12}$,Ala$^{16,17,19}$,Ala$^{24}$,Asp$^{25}$,Leu$^{26}$,Lys$^{27,28}$]-VIP cyclo (Lys$^{21}$→Asp$^{25}$) [Ac-(SEQ ID NO:64)-NH$_2$]

Ac-[Glu$^8$,Lys$^{12}$,Nle$^{17}$,Ala$^{19}$,Asp$^{25}$,Val$^{26}$,Thr$^{28}$,Gly$^{29,30}$, Thr$^{31}$]-VIP cyclo (Lys$^{21}$→Asp$^{25}$) [Ac-(SEQ ID NO:65)-NH$_2$]

Ac-[p-F-Phe$^6$,Glu$^8$,Lys$^{12}$,Nle$^{17}$,Asp$^{25}$,Val$^{26}$,Thr$^{28}$,Gly$^{29,30}$, Thr$^{31}$]-VIP cyclo (Lys$^{21}$→Asp$^{25}$) [Ac-(SEQ ID NO:66)-NH$_2$]

Ac-[Ala$^2$,Glu$^8$,Lys$^{12}$,Nle$^{17}$,Asp$^{25}$,Leu$^{26}$,Lys$^{27,28}$,Gly$^{29,30}$, Thr$^{31}$]-VIP cyclo (Lys$^{21}$→Asp$^{25}$) [Ac-(SEQ ID NO:67)-NH$_2$]

Ac-[Glu$^8$,Lys$^{12}$,Nle$^{17}$,Asp$^{25}$,Leu$^{26}$,Lys$^{27,28}$,Gly$^{29,30}$,Thr$^{31}$]-VIP cyclo (Lys$^{21}$→Asp$^{25}$) [Ac-(SEQ ID NO:68)-NH$_2$]

Ac-[Lys$^{12}$,Nle$^{17}$,Ala$^{19}$,Asp$^{25}$,Leu$^{26}$,Lys$^{27,28}$,Ala$^{29-31}$]-VIP cyclo (Lys$^{21}$→Asp$^{25}$) [Ac-(SEQ ID NO:69)-NH$_2$]

The compounds of the present invention may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group or other reactive groups protected and the free primary carboxyl group of another amino acid or residue thereof having its amino group or other reactive groups protected.

The process for synthesizing the compounds of the present invention may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Such conventional procedures for synthesizing the novel compounds of the present invention include for example any solid phase peptide synthesis method. In such a method, the synthesis of the novel compounds can be carried out by sequentially incorporating the desired amino acid residues one at a time into the growing peptide chain according to the general principles of solid phase methods [Merrifield, R. B., J. Amer. Chem. Soc. 85, 2149–2154 (1963); Barany et al., The Peptides, Analysis, Synthesis and Biology, Vol. 2, Gross, E. and Meienhofer, J., Eds. Academic Press 1–284 (1980)].

Common to chemical syntheses of peptides is the protection of reactive side chain groups of the various amino acid moieties with suitable protecting groups which will prevent a chemical reaction from occuring at that site until the protecting group is ultimately removed. Usually also common is the protection of the alpha amino group on an amino acid or fragment while that entity reacts at the carboxyl group, followed by the selective removal of the alpha amino protecting group to allow a subsequent reaction to take place at that site. While specific protecting groups have been disclosed in regard to the solid phase synthesis method, it should be noted that each amino acid can be protected by an protective group conventionally used for the respective amino acid in solution phase synthesis.

Alpha amino groups may be protected by a suitable protecting group selected from aromatic urethane-type protecting groups, such as benzyloxycarbonyl (Z) and substituted benzyloxycarbonyl, such as p-chlorobenzyloxycarbonyl, p-nitrobenzyloxycarbonyl, p-bromobenzyl-oxycarbonyl, p-biphenyl-isopropyloxycarbonyl, 9-fluorenylmethyl-oxycarbonyl (Fmoc) and p-methoxybenzyloxycarbonyl (Moz); aliphatic urethane-type protecting groups, such as t-butyloxycarbonyl (Boc), diisopropylmethyloxycarbonyl, isopropyloxycarbonyl, and allyloxycarbonyl. Boc is most preferred for alpha amino protection.

Carboxyl groups may be protected by a suitable protecting group selected from aromatic esters such as benzyl (OBzl) or benzyl substituted with lower alkyl, halo, nitro, thio, or substituted thio, i.e., lower alkyl (1–7 carbon atoms) thio; aliphatic esters such as lower alkyl, t-butyl (Ot-Bu), cyclopentyl, cyclohexyl (OcHx), cycloheptyl, and 9-fluorenylmethyl (OFm). OBzl and OFm are most preferred for glutamic acid (Glu). OChx, OBzl and OFm are most preferred for aspartic acid (Asp).

Hydroxyl groups may be protected by a suitable protecting group selected from ethers such as benzyl (Bzl) or benzyl substituted with lower alkyl, halo, such as 2,6-dichlorobenzyl (DCB), nitro, or methoxy; t-butyl (t-Bu), tetrahydropyranyl, and triphenylmethyl (trityl). Bzl is most preferred for serine (Ser) and threonine (Thr). Bzl and DCB are most preferred for tyrosine (Tyr).

Side chain amino groups may be protected by a suitable protecting group selected from aromatic urethane-type protecting groups such as benzyloxycarbonyl (Z) and substituted benzyloxycarbonyl, such as p-chlorobenzyloxycarbonyl, 2-chlorobenzyloxycarbonyl (2-Cl-Z), p-nitro-benzyloxycarbonyl, p-bromobenzyloxycarbonyl, p-biphenyl-isopropyloxycarbonyl, 9-fluorenylmethyloxycarbonyl (Fmoc) and p-methoxy-benzyloxycarbonyl (Moz); aliphatic urethane-type protecting groups, such as t-butyloxycarbonyl (Boc), diisopropylmethyloxycarbonyl, isopropyloxycarbonyl, and allyloxycarbonyl. Z is most preferred for ornithine (Orn). 2-Cl-Z and Fmoc are most preferred for lysine (Lys).

Guanidino groups may be protected by a suitable protecting group selected from nitro, p-toluenesulfonyl (Tos), Z, adamantyloxycarbonyl, and Boc. Tos is most preferred for arginine (Arg).

Side chain amide groups may be protected by xanthyl (Xan). No protection is preferred for asparagine (Asn) and glutamine (Gln).

Imidazole groups may be protected by a suitable protecting group selected from p-toluenesulfonyl (Tos), 9-fluorenylmethyloxycarbonyl (Fmoc), triphenylmethyl (trityl), 2,4-dinitrophenyl (Dnp), Boc and benzyloxymethyl (Bom). Tos and Bom are most preferred for histidine (His).

All solvents, isopropanol (iPrOH), methylene chloride (CH$_2$Cl$_2$), and dimethylformamide (DMF) were purchased from Fisher or Burdick & Jackson and were used without additional distillation. Trifluoroacetic acid was purchased from Halocarbon and used without further purification. Diisopropylethylamine (DIPEA) was purchased from Pfaltz and Bauer and distilled from CaO and ninhydrin prior to use. Dicyclohexylcarbodiimide (DCC) and diisopropylcarbodiimide (DIC) were purchased from Fluka and used without further purification. Hydroxybenzotriazole (HOBT) and 1,2-ethanedithiol (EDT) were purchased from Sigma Chemical Co. and used without further purification. Protected amino acids were generally of the L configuration and were obtained commercially from Chemical Dynamics Corp. or Bachem. Purity of these reagents were confirmed by thin layer chromatography, NMR and melting point prior to use. Boc-O-Me-Tyr, Boc-2-Nal, and Boc-p-F-Phe were prepared as reported. [Bolin, D. R., U.S. Pat. No. 5,141,924 issued Aug. 25, 1992. Boc-Asp(OFm) and Boc-Glu(OFm) were prepared as reported. [Bolin, D. R., et al., Org. Prep. Proc. Int., 21, 67–74 (1989)]. Benzhydrylamine resin (BHA) was a copolymer of styrene—1% divinylbenzene (100–200 or 200–400 mesh) obtained from Biomega, Bachem, Omni or Advanced Chemtech. Total nitrogen content of these resins were generally between 0.3–1.2 meq/g.

Thin layer chromatography (TLC) was performed on glass backed precoated silica gel 60 F254 plates (Merck) using appropriate solvent systems. Detection of compounds was performed by UV fluorescence quenching (254 nm absorption), iodine staining, or ninhydrin spray (for primary and secondary amines).

For amino acid composition analyses, peptides were hydrolyzed in 6N HCl, containing 1–4 mg of phenol, at 115° C. for 22–24 hours in sealed, evacuated hydrolysis tubes. Analyses were performed on either a BECKMAN 121M amino acid analyzer or a WATERS HPLC-based amino acid analysis system using either a WATERS CAT EX resin or a PIERCE AA511 column and ninhydrin detection.

High performance liquid chromatography (HPLC) was conducted on an LDC apparatus consisting of CONSTAMETRIC I and III pumps, a GRADIENT MASTER solvent programmer and mixer, and a SPECTROMONITOR III variable wavelength UV detector. Analytical HPLC was performed in reversed phase mode using WATERS BONDAPAK $C_{18}$ columns (0.4×30 cm). Preparative HPLC separations were run on WHATMAN MAGNUM 20 PARTISIL 10 ODS-3 columns (2×25 cm or 2×50 cm) equipped with a WATERS GUARD-PAK $C_{18}$ precolumn. Gel chromatography was performed using a 2×85 cm column, an LKB VARIOPERPEX peristaltic pump, and an IBM variable wavelength UV detector.

Peptides were preferably prepared using solid phase synthesis by the method generally described by Merrifield, [J. Amer. Chem. Soc., 85, 2149 (1963)], although other equivalent chemical synthesis known in the art could be used as previously mentioned. Solid phase synthesis is commenced from the C-terminal end of the peptide by coupling a protected alpha-amino acid to a suitable resin. Such a starting material can be prepared by attaching an alpha-amino-protected amino acid by an ester linkage to a chloromethylated resin or a hydroxymethyl resin, or by an amide bond to a benzhydrylamine (BHA) or para-methylbenzhydrylamine (MBHA) resin. Preparation of the hydroxymethyl resin is well known in the art. Chloromethylated resins are commercially available and the preparation is also well known in the art. BHA and MBHA resin supports are commercially available and generally used when the desired peptide being synthesized has an unsubstituted amide at the C-terminus.

In general, the first amino acid to be coupled onto the BHA resin was added as the Boc-amino acid symmetrical anhydride, using 2–10 equivalents of activated amino acid per resin nitrogen equivalent. After coupling, the resin was washed and dried under vacuum. Loading of the amino acid onto the resin may be determined by amino acid analysis of an aliquot of Boc-amino acid resin. Loadings generally ranged from 0.2 to 0.4 mmol/g resin. Any unreacted amino groups, may be capped by reacting the resin with acetic anhydride and diisopropylethylamine in methylene chloride.

Following addition of the Boc-amino acid, the resins were carried through several repetitive cycles to add amino acids sequentially. The alpha amino Boc protection was removed under acidic conditions. Trifluoroacetic acid (TFA) in methylene chloride, HCl in dioxane or formic acid/acetic acid mixtures may be used for this purpose. Preferably 50% TFA in methylene chloride (v/v) is utilized. This may also contain 1–5% by volume of EDT or dimethylsulfide as a scavenger for t-butyl carbonium ions. Other standard cleavage reagents as known in the art may also be used.

Following the removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. For example, appropriate reagents for such syntheses are benzotriazol-1-yloxy-tri-(dimethylamino)phosphonium hexafluorophosphate (BOP), dicyclohexylcarbodiimide (DCC), and diisopropylcarbodiimide (DIC). Preferred here are DCC and DIC. Other activating agents are described by Barany and Merrifield [in The Peptides, Vol. 2, J. Meienhofer, ed., Academic Press, 1979, pp 1–284] may be utilized. Various reagents such as 1-hydroxybenzotriazole (HOBT), N-hydroxysuccinimide (HOSu) and 3,4-dihydro-3-hydroxy-4-oxo-1,2,3-benzotriazine (HOOBT) may be added to the coupling mixtures in order to optimize the synthetic cycles. Preferred here is HOBT.

The protocol for a typical synthetic cycle was as follows:

| Protocol 1 | | |
|---|---|---|
| Step | Reagent | Time |
| 1 | $CH_2Cl_2$ | 2 × 30 sec |
| 2 | 50% TFA/$CH_2Cl_2$ | 1 min |
| 3 | 50% TFA/$CH_2Cl_2$ | 15 min |
| 4 | $CH_2Cl_2$ | 2 × 30 sec |
| 5 | iPrOH | 2 × 30 sec |
| 6 | $CH_2Cl_2$ | 4 × 30 sec |
| 7 | 6% DIPEA/$CH_2Cl_2$ | 3 × 2 min |
| 8 | $CH_2Cl_2$ | 3 × 30 sec |
| 9 | coupling | 10 min–18 hours |
| 10 | $CH_2Cl_2$ | 2 × 30 sec |
| 11 | iPrOH | 1 × 30 sec |
| 12 | $CH_2Cl_2$ | 1 × 30 sec |
| 13 | DMF | 2 × 30 sec |
| 14 | $CH_2Cl_2$ | 3 × 30 sec |

Solvents for all washings and couplings were measured to volumes of 10–40 ml/g resin. Couplings were performed using either the preformed symmetrical anhydrides of the Boc-amino acids or as the O-acyl isourea derivatives. Generally, 2–10 equivalents of activated Boc-amino acid was added per equivalent of amine resin using methylene chloride as solvent. Boc-Arg(Tos), Boc-Gln, Boc-Asn, Boc-His(Tos), and Boc-His(Bom) were coupled in 20–25% DMF/$CH_2Cl_2$. Boc-Asn, Boc-Gln, and Boc-His(Bom) were coupled as their HOBT active esters in order to minimize known side reactions.

The peptides were generally cyclized in the following manner. At the amino acid sites within the peptide where the side chains are to be linked, different protecting groups were utilized. For the amine site amino acids, Lys and Orn, the $N^\epsilon$- and $N^\delta$-Fmoc derivatives were incorporated into the peptide chain. For the carboxyl site amino acids, Asp and Glu, the $O^\beta$- and $O^\gamma$-Fm derivatives were incorporated. The peptide, while still attached to the resin, was treated with 20–40% piperidine in DMF to remove, selectively, the Fmoc and Fm protecting groups. The free side chain amine and carboxyl groups were then linked covalently by treatment with an appropriate amide forming reagent such as diphenylphosphoryl azide (DPPA), DCC, DIC or BOP. Preferred here are DCC and BOP.

The protocol for a typical cyclization process was as follows:

Protocol 2

| Step | Reagent | Time |
|---|---|---|
| 1 | DMF | 1 × 30 sec |
| 2 | 20–40% piperidine/DMF | 1 min |
| 3 | DMF | 1 × 30 sec |
| 4 | 20–40% piperidine/DMF | 20 min |
| 5 | iPrOH | 1 × 30 sec |
| 6 | DMF | 1 × 30 sec |
| 7 | iPrOH | 2 × 30 sec |
| 8 | DMF | 2 × 30 sec |
| 9 | 6% DIPEA/CH$_2$Cl$_2$ | 2 × 2 min |
| 10 | CH$_2$Cl$_2$ | 1 × 30 sec |
| 11 | DMF | 1 × 30 sec |
| 12 | coupling | 1–24 hours |
| 13 | iPrOH | 1 × 30 sec |
| 14 | CH$_2$Cl$_2$ | 1 × 30 sec |
| 15 | DMF | 2 × 30 sec |
| 16 | CH$_2$Cl$_2$ | 3 × 30 sec |

Coupling reactions throughout the synthesis were monitored by the Kaiser ninhydrin test to determine extent of completion [Kaiser et al., Anal. Biochem., 34, 595–598 (1970)]. Slow reaction kinetics were observed for Boc-Arg (Tos), Boc-Asn, and Boc-Gln. Any incomplete coupling reactions were either recoupled with freshly prepared activated amino acid or capped by treating the peptide resin with acetic anhydride as described above. The fully assembled peptide-resins were dried in vacuo for several hours.

For each compound, the blocking groups were removed and the peptide cleaved from the resin by the following procedure. Generally, the peptide-resins were treated with 25–100 µL ethanedithiol, 1 mL anisole, and 9 mL liquid hydrogen fluoride, per gram of resin, at 0° C. for 45–60 min, in a TEFLON HF apparatus (Peninsula). Alternatively, a modified two step cleavage procedure [Tam et al., Tetrahedron Letters, 23, 2939–2940 (1982)] could be used wherein the peptide-resin was treated with 3 mL dimethyl sulfide and 1 mL hydrogen fluoride for 2 hours at 0° C. and evaporated prior to the 90% HF treatment. Volatile reagents were then removed under vacuum at ice bath temperature. The residue was washed with two or three 20 mL volumes each of Et$_2$O and EtOAc and filtered. The peptides were extracted from the resin by washing with three or four 20 mL volumes of 10% AcOH and filtered. The combined aqueous filtrates were lyophilized to yield the crude product.

The crude peptides were initially purified by gel chromatography on SEPHADEX G-25 fine media in order to separate monomeric from oligomeric materials. The peptides were dissolved in a minimal volume of 10% AcOH and applied to the gel column. The column was eluted with 10% AcOH at a flow rate of 0.5–1.5 mL/min. The effluent was monitored at 254 nm and the fractions containing the desired band were pooled and lyophilized to yield semi-purified products.

Purification of the semi-purified peptides were generally carried out by preparative HPLC. The peptides were applied to the columns in a minimum volume of either 1% AcOH or 0.1% TFA. Gradient elution was generally started at 10% B buffer, 10–25% B in 10 minutes, and 25–35% B in 3 hours (buffer A: 0.1% TFA/H$_2$O, buffer B: 0.1% TFA/CH$_3$CN) at a flow rate of 8.0 mL/min. UV detection was made at 220 nm. Fractions were collected at 1.5–2.5 minute intervals and inspected by analytical HPLC. Fractions judged to be of high purity were pooled and lyophilized.

Purity of the final products were checked by analytical HPLC on a reversed phase column as stated above. Generally, a gradient elution of 20–40% B (buffer A: 0.022% TFA/H$_2$O, buffer B: 0.022% TFA/CH$_3$CN) in 15 minutes at 2.0 mL/min. UV detection was at 210 nm. Purity of all products was judged to be approximately 97–99%. Amino acid analyses of the individual peptides were performed and the values obtained were within acceptable limits. In general, all final products were also subjected to fast atom bombardment mass spectrometry (FAB-MS). All products yielded the expected parent M+H ions within acceptable limits.

The novel compounds of the present invention have valuable pharmacological properties. They have tracheal relaxant activity, and they are potent bronchodilators. The compounds also have no cardiovascular side effects. The bronchodilation produced by these novel peptides can be sustained for greater than two hours. Thus, being highly active bronchodilators, the compounds are valuable pharmaceutical agents for treatment of bronchoconstrictive disorders, e.g., asthma.

The novel compounds of formulas I–V may be combined with various typical pharmaceutical carriers to provide compositions suitable for use in the treatment of bronchoconstrictive disorders such as asthma. The dosage of these compounds is dependant upon various factors such as the particular compound employed and the particular formulation. An effective dosage can be determined by one of ordinary skill in the art from the effective concentration (EC$_{50}$) disclosed herein. Typical dosages in humans would be 0.01–100 µg/kg. For compounds having a low ED$_{50}$, such as 0.1 µg, typical dosages in humans would be from about 0.02–20 µg/kg.

Novel compounds of formulas I–V form pharmaceutically acceptable acid addition salts with a variety of inorganic and organic acids such as sulfuric, phosphoric, hydrochloric, hydrobromic, hydroiodic, nitric, sulfamic, citric, lactic, pyruvic, oxalic, maleic, succinic, tartaric, cinnamic, acetic, trifluoroacetic, benzoic, salicylic, gluconic, ascorbic, and related acids.

The instant compounds may be administered to a patient by parenteral application either intravenously, subcutaneously, intramuscularly, orally, or intranasally. A preferred route for parenteral administration is by aerosol via oral or intranasal administration.

The present invention is further illustrated by the examples which follow.

EXAMPLE 1

Preparation of Boc-Thr(Bzl)-BHA Resin

Benzhydrylamine copolystyrene-1% divinylbenzene cross-linked resin (9.5 g, 3.6 mequiv, 200–400 ASTM mesh, Vega Biochem) was swelled in 100 mL methylene chloride, filtered and washed using steps 7–8 of protocol 1. Boc-Thr (Bzl) (3.35 g, 10.8 mmole) and dicyclohexylcarbodiimide (1.12 g, 5.42 mmol) were reacted in 50 mL CH$_2$Cl$_2$ for 1 hour, filtered and added in 50 mL CH$_2$Cl$_2$ to the swelled resin. This mixture was shaken for 18 hours at room temperature. DIPEA (630 mL, 3.6 mmol) was added and then shaken for an additional 1 hour, filtered and then steps 10–14 of protocol 1 were performed. Kaiser ninhydrin analysis was negative. Any unreacted amine groups were capped by treating the resin with 1 mL acetic anhydride and 1 mL DIPEA in 50 mL methylene chloride for 30 minutes, filtered and washed with steps 13–14 of protocol 1. The resin was dried under vacuum overnight to yield 9.8 g of Boc-Thr(Bzl)-BHA resin. A portion of this resin was subjected to amino acid analysis which indicated a loading of 0.17 mmol Thr/g.

EXAMPLE 2

Preparation of Ac-[$Lys^{12}$,$Nle^{17}$,$Val^{26}$,$Thr^{28}$]-VIP cyclo ($Asp^8 \rightarrow Lys^{12}$) [Ac-(SEQ ID No:20)-$NH_2$]

The Boc-Thr(Bzl)-BHA resin (9.8 g, 1.7 mmol) from Example 1 was subjected to solid phase synthesis using protocol 1 above. All couplings were performed using preformed symmetrical anhydrides prepared from Boc-amino acid and dicyclohexylcarbodiimide. Boc-asparagine, Boc-glutamine, and Boc-histidine(benzyloxymethyl) were coupled as the respective HOBT active esters. Reaction times were generally 1–18 hours for completion of the coupling step. Five coupling cycles were performed of one cycle each with Boc-Leu (1.5 g, 6.0 mmol), Boc-Val (1.3 g, 6.0 mmol), Boc-Ser(Bzl) (1.8 g, 6.0 mmol), Boc-Asn (773 mg, 3.3 mmol), and Boc-Leu (1.5 g, 6.0 mmol). The resin was dried under vacuum to give 12.2 g of Boc-hexapeptide resin.

A 8.2 g (1.13 mmol) portion of this resin was coupled with six cycles of one cycle each with Boc-Tyr(2,6-DCB) (1.77 g, 4.0 mmol), Boc-Lys(2-Cl-Z) (1.67 g, 4.0 mmol), Boc-Lys(2-Cl-Z) (1.67 g, 4.0 mmol), Boc-Val (876 mg, 4.0 mmol), Boc-Ala (762 mg, 4.0 mmol), and Boc-Nle (932 mg, 4.0 mmol) to give 10.2 g of Boc-dodecapeptide resin.

A 1.26 g (0.139 mmol) portion of this resin was carried through two coupling cycles of one cycle each with Boc-Gln (205 mg, 0.93 mmol) and Boc-Lys(2-Cl-Z) (627 mg, 1.5 mmol). One half of this resin (0.069 mmol) was carried through fourteen coupling cycles of one cycle each with Boc-Arg(Tos) (324 mg, 0.76 mmol), Boc-Leu (188 mg, 0.76 mmol), Boc-Lys(Fmoc) (354 mg, 0.76 mmol), Boc-Thr(Bzl) (234 mg, 0.76 mmol), Boc-Tyr(2,6-DCB) (333 mg, 0.76 mmol), Boc-Asn (97 mg, 0.76 mmol), Boc-Asp(OFm) (311 mg, 0.76 mmol), Boc-Thr(Bzl) (234 mg, 0.76 mmol), Boc-Phe (201 mg, 0.76 mmol), Boc-Val (164 mg, 0.76 mmol), Boc-Ala (143 mg, 0.76 mmol), Boc-Asp(OcHx) (238 mg, 0.76 mmol), Boc-Ser(Bzl) (223 mg, 0.76 mmol), and Boc-His(Bom) (156 mg, 0.41 mmol). The peptide resin was carried through steps 1–8 of protocol 1 and treated with 1.0 mL acetic anhydride and 66 mL DIPEA (0.38 mmol) in 20 mL methylene chloride for 30 minutes. The resin was washed using steps 10–14.

The resin was then selectively deblocked by treating with steps 1–11 of protocol 2 and reacted seven times with DCC (49 mg, 0.24 mmol) and HOBT (32 mg, 0.24 mmol) in 20 mL distilled DMF for 24 hours. Kaiser ninhydrin analysis was negative. The resin was washed using steps 13–16 of protocol 2 and dried under vacuum to yield 0.72 g.

This resin was treated with 6 mL dimethylsulfide and 2 mL liquid HF for 2 hours and 0° C. The reaction mixture was evaporated and the residue was treated with 0.7 mL anisole and 6 mL liquid HF for 45 minutes at 0° C. The reaction mixture was evaporated and the residue was washed with 1×15 mL $Et_2O$ and 3×15 mL EtOAc. The resin was extracted with 3×20 mL 10% AcOH. The combined aqueous filtrates were lyophilized to yield 227 mg of a white solid.

This crude material was purified by preparative HPLC on a WHATMAN MAGNUM-20 ODS-3 column (2×25 cm) and eluted with a linear gradient of 10–40% B (buffer A: 0.1% TFA/$H_2O$, buffer B: 0.1% TFA/CH3CN) in 4 hours. The main peak was cut by analytical HPLC analysis of collected fractions, pooled and lyophilized to yield 26.7 mg of semi-pure product. This material was reapplied to a MAGNUM-20 ODS-3 column (2×50 cm) and eluted with the same gradient. The main peak was cut and lyophilized to yield 9.5 mg of a white, amorphous powder. This compound was homogeneous by HPLC and gave a correct amino acid analysis. FAB-MS: MH calc. 3277.8, found 3276.1.

EXAMPLE 3

Preparation of Ac-[$Glu^8$,$Lys^{12}$,$Nle^{17}$,$Val^{26}$,$Thr^{28}$]-VIP cyclo ($Glu^8 \rightarrow Lys^{12}$) [Ac-(SEQ ID No:21)-$NH_2$]

Benzhydrylamine copolystyrene-1% divinylbenzene cross-linked resin (17.7 g, 2.6 mequiv, 200–400 ASTM mesh, Vega Biochem) was swelled in 160 mL methylene chloride, filtered and washed using steps 7–8 of protocol 1. The resin was resuspended in 160 mL methylene chloride and to this was added Boc-Thr(Bzl) (6.25 g, 20.2 mmole) and dicyclohexylcarbodiimide (2.10 g, 10.1 mmol). This mixture was shaken for 8 hours at room temperature, filtered and then steps 10–14 of protocol 1 were performed. Kaiser ninhydrin analysis was negative. Unreacted amine groups were capped by treating the resin with 5 mL acetic anhydride and 5 mL DIPEA in 150 mL methylene chloride for 60 minutes, filtered and washed with steps 13–14. The resin was dried under vacuum overnight to yield 18.0 g of Boc-Thr(Bzl)-BHA resin. A portion of this resin was subjected to amino acid analysis which indicated a loading of 0.17 mmol Thr/g.

The Boc-Thr(Bzl)-BHA resin (18.0 g, 3.06 mmol) was subjected to solid phase synthesis using the above protocol 1. All couplings were performed using preformed symmetrical anhydrides prepared from Boc-amino acid and dicyclohexylcarbodiimide. Boc-asparagine, Boc-glutamine, and Boc-histidine(benzyloxymethyl) were coupled as the respective HOBT active esters. Five coupling cycles were performed of one cycle each with Boc-Leu (6.1 g, 24.5 mmol), Boc-Val (5.32 g, 24.5 mmol), Boc-Ser(Bzl) (7.23 g, 24.5 mmol), Boc-Asn (3.13 g, 13.5 mmol), and Boc-Leu (6.1 g, 24.5 mmol). The resin was dried under vacuum to give 22.9 g of Boc-hexapeptide resin.

A 7.48 g (1.0 mmol) portion of this resin was carried through ten coupling cycles of one cycle each with Boc-Tyr (2,6-DCB) (1.76 g, 4.0 mmol), Boc-Lys(2-Cl-Z) (1.66 g, 4.0 mmol), Boc-Lys(2-Cl-Z) (1.66 g, 4.0 mmol), Boc-Val (869 mg, 4.0 mmol), Boc-Ala (1.5 g, 8.0 mmol), Boc-Nle (925 mg, 4.0 mmol), Boc-Gln (1.08 g, 4.4 mmol), Boc-Lys(2-Cl-Z) (1.66 g, 4.0 mmol), Boc-Arg(Tos) (1.71 g, 4.0 mmol) and Boc-Leu (998 mg, 4.0 mmol) to give 9.6 g of Boc-hexadecapeptide resin.

A 7.68 g (0.8 mmol) portion of this resin was carried through one coupling cycle with Boc-Lys(Fmoc) (1.5 g, 3.2 mmol) to give 8.32 g of Boc heptadecapeptide resin.

A 6.24 g (0.6 mmol) portion of this resin was carried through two coupling cycles of one cycle each with Boc-Thr(Bzl) (742 mg, 2.4 mmol) and Boc-Tyr(2,6-DCB) (1.06 g, 2.4 mmol) to give 6.28 g of Boc-nonadecapeptide resin.

A 2.09 g (0.2 mmol) portion of this resin was carried through nine coupling cycles of one cycle each with Boc-Asn (204 mg, 0.88 mmol), Boc-Asp (OFm) (340 mg, 0.8 mmol), Boc-Thr (Bzl) (248 mg, 0.8 mmol), Boc-Phe (212 mg, 0.8 mmol), Boc-Val (174 mg, 0.8 mmol), Boc-Ala (151 mg, 0.8 mmol), Boc-Asp(OcHx) (258 mg, 0.8 mmol), Boc-Ser(Bzl) (236 mg, 0.8 mmol), and Boc-His(Bom) (330 mg, 0.88 mmol). The peptide resin was carried through steps 1–8 of protocol 1 and treated with 0.25 mL acetic anhydride and 70 mL DIPEA in 20 mL methylene chloride for 20 minutes. The resin was washed using steps 10–14.

The resin was then selectively deblocked by treating with steps 1–11 of protocol 2. Three quarters of this resin (0.15 mmol) was reacted with DCC (77 mg, 0.37 mmol) and HOBT (51 mg, 0.37 mmol) in 20 mL distilled DMF for 72 hours and in 20 mL toluene for 24 hours. Kaiser ninhydrin analysis was negative. The resin was washed using steps 13–16 of protocol 2 and dried under vacuum to yield 1.72 g.

A 1.14 g (0.099 mmol) portion of this resin was deblocked by treatment as in Example 2 except that 1 mL anisole and 9 mL HF was used in the second step. The reaction mixture was evaporated and the residue was washed with 1×15 mL Et$_2$O and 3×15 mL EtOAc. The resin was extracted with 3×20 mL 10% AcOH. The combined aqueous filtrates were lyophilized to yield 535 mg of a white solid.

This crude material was purified by gel filtration on SEPHADEX G-25 fine (2×100 cm column) by elution with 10% AcOH. The monomeric peak was cut by analytical HPLC analysis of collected fractions, pooled and lyophilized to give 83.5 mg of semipurified product. This material was further purified by preparative HPLC as in Example 2 except that a linear gradient of 20–40% in 3 hours was run. The main peak was cut by analytical HPLC analysis of collected fractions, pooled and lyophilized to yield 18.9 mg of a white, amorphous powder. This compound was homogeneous by HPLC and gave a correct amino acid analysis. FAB-MS: MH calc. 3292.0, found 3291.8.

EXAMPLE 4

Preparation of Ac-[Asn$^8$,Asp$^9$,Lys$^{12}$,Nle$^{17}$,Val$^{26}$,Thr$^{28}$]-VIP cyclo (Asp$^9$→Lys$^{12}$) [Ac-(SEQ ID No:22)-NH$_2$]

A 1.55 g (0.15 mmol) portion of the Boc-nonadecapeptide resin from Example 3 was carried through nine coupling cycles of one cycle each with Boc-Asp(OFm) (247 mg, 0.6 mmol), Boc-Asn (153 mg, 0.66 mmol), Boc-Thr(Bzl) (248 mg, 0.8 mmol), Boc-Phe (159 mg, 0.6 mmol), Boc-Val (130 mg, 0.6 mmol), Boc-Ala (113 mg, 0.6 mmol), Boc-Asp (OcHx) (189 mg, 0.6 mmol), Boc-Ser(Bzl) (177 mg, 0.6 mmol), and Boc-His(Bom) (248 mg, 0.66 mmol). The peptide resin was carried through steps 1–8 of protocol 1 and treated with 0.25 mL acetic anhydride and 70 mL DIPEA in 20 mL methylene chloride for 30 minutes. The resin was washed using steps 10–14.

The resin was then selectively deblocked by treating with steps 1–11 of protocol 2 and reacted twice with DCC (77 mg, 0.37 mmol) and HOBT (51 mg, 0.37 mmol) in 20 mL distilled DMF for 24 and 72 hours and twice in 20 mL toluene for 24 and 48 hours. Kaiser ninhydrin analysis was negative. The resin was washed using steps 13–15 of protocol 2 and dried under vacuum to yield 1.54 g.

A 1.26 g (0.122 mmol) portion of this resin was deblocked by treatment with HF as in Example 3. The reaction mixture was evaporated and the residue was washed with 1×15 mL Et$_2$O and 3×15 mL EtOAc. The resin was extracted with 3×20 mL 10% AcOH. The combined aqueous filtrates were lyophilized to yield 485 mg of a white solid.

This crude material was purified by gel filtration on SEPHADEX G-25 fine as in Example 3 to give 83.5 mg of semipurified product. This material was further purified by preparative HPLC as in Example 3 except that a linear gradient of 20–45% in 3 hours was run. The main peak was cut by analytical HPLC analysis of collected fractions, pooled and lyophilized to yield 11.5 mg of a white, amorphous powder. This compound was homogeneous by HPLC and gave a correct amino acid analysis. FAB-MS: MH calc. 3277.8, found 3277.6.

EXAMPLE 5

Preparation of Ac-[Orn$^{12}$,Nle$^{17}$,Val$^{26}$,Thr$^{28}$]-VIP cyclo (Asp$^8$→Orn$^{12}$) [Ac-(SEQ ID No:23)-NH$_2$]

A 1.92 g (0.2 mmol) portion of the Boc-hexadecapeptide resin from Example 3 was carried through twelve coupling cycles of one cycle each with Boc-Orn (Fmoc) (364 mg, 0.8 mmol), Boc-Thr(Bzl) (495 mg, 1.6 mmol), Boc-Tyr(2,6-DCB) (352 mg, 0.8 mmol), Boc-Asn (102 mg, 0.44 mmol), Boc-Asp(OFm) (329 mg, 0.8 mmol), Boc-Thr(Bzl) (495 mg, 1.6 mmol), Boc-Phe (212 mg, 0.8 mmol), Boc-Val (174 mg, 0.8 mmol), Boc-Ala (151 mg, 0.8 mmol), Boc-Asp(OcHx) (252 mg, 0.8 mmol), Boc-Ser(Bzl) (236 mg, 0.8 mmol), and Boc-His(Bom) (330 mg, 0.88 mmol). The peptide resin was carried through steps 1–8 of protocol 1 and treated with 0.25 mL acetic anhydride and 70 mL DIPEA in 20 mL methylene chloride for 30 minutes. The resin was washed using steps 10–14 and dried overnight to yield 2.38 g.

A 1.38 g (0.11 mmol) portion of this resin was then selectively deblocked by treating with steps 1–11 of protocol 2 and reacted with DCC (55 mg, 0.27 mmol) and HOBT (37 mg, 0.27 mmol) in 20 mL distilled DMF for 24 hours, in 20 mL toluene for 24 hours and five times in 20 mL distilled DMF for 24 hours. Kaiser ninhydrin analysis was slightly positive. The resin was washed using steps 13–16 of protocol 2 and dried under vacuum.

A 0.8 g (0.05 mmol) portion of this resin was deblocked by treatment with HF as in Example 3. The reaction mixture was evaporated and the residue was washed with 1×15 mL Et$_2$O and 3×15 mL EtOAc. The resin was extracted with 3×20 mL 10% AcOH. The combined aqueous filtrates were lyophilized to yield 429 mg of a gummy solid.

This crude material was purified by gel filtration on SEPHADEX G-25 fine as in Example 3 to give 107 mg of semipurified product. This material was further purified by preparative HPLC as in Example 3 except that a linear gradient of 10–40% in 3 hours was run. The main peak was cut by analytical HPLC analysis of collected fractions, pooled and lyophilized to yield 17.5 mg of a white, amorphous powder. This compound was homogeneous by HPLC and gave a correct amino acid analysis. FAB-MS: MH calc. 3263.7, found 3264.1.

EXAMPLE 6

Preparation of Ac-[Lys$^8$,Asp$^{12}$,Nle$^{17}$,Val$^{26}$,Thr$^{28}$]-VIP cyclo (Lys$^8$→Asp$^{12}$) [Ac-(SEQ ID No:24)-NH$_2$]

A 1.0 g (0.1 mmol) portion of the Boc-hexadecapeptide resin from Example 3 was carried through twelve coupling cycles of one cycle each with Boc-Asp(OFm) (165 mg, 0.4 mmol), Boc-Thr(Bzl) (124 mg, 0.4 mmol), Boc-Tyr(2,6-DCB) (176 mg, 0.4 mmol), Boc-Asn (102 mg, 0.44 mmol), Boc-Lys(Fmoc) (187 mg, 0.4 mmol), Boc-Thr(Bzl) (124 mg, 0.4 mmol), Boc-Phe (106 mg, 0.4 mmol), Boc-Val (87 mg, 0.4 mmol), Boc-Ala (76 mg, 0.4 mmol), Boc-Asp (OcHx) (126 mg, 0.4 mmol), Boc-Ser(Bzl) (118 mg, 0.4 mmol), and Boc-His(Bom) (150 mg, 0.4 mmol). The peptide resin was carried through protocol steps 1–8 and treated with 0.5 mL acetic anhydride and 35 mL DIPEA in 20 mL methylene chloride for 30 minutes. The resin was washed using steps 10–14 and dried overnight to yield 1.2 g.

A 0.8 g (0.066 mmol) portion of this resin was then selectively deblocked by treating with steps 1–11 of protocol 2 and reacted with BOP (58 mg, 0.13 mmol) in 20 mL distilled DMF for 24 hours. Kaiser ninhydrin analysis was negative. The resin was washed using steps 13–16 of protocol 2 and dried under vacuum.

This resin was deblocked by treatment with HF as in Example 3. The reaction mixture was evaporated and the residue was washed with 1×15 mL Et$_2$O and 3×15 mL EtOAc. The resin was extracted with 3×20 mL 10% AcOH. The combined aqueous filtrates were lyophilized to yield a gummy solid.

This crude material was purified by gel filtration on SEPHADEX G-25 fine as in Example 3 to give 43.8 mg of semipurified product. This material was further purified by preparative HPLC as in Example 3 except that a linear gradient of 10–40% in 3 hours was run. The main peak was cut by analytical HPLC analysis of collected fractions, pooled and lyophilized to yield 7.5 mg of a white, amorphous powder. This compound was homogeneous by HPLC and gave a correct amino acid analysis. FAB-MS: MH calc. 3277.8, found 3276.4.

EXAMPLE 7

Preparation of Ac-[Glu$^8$,Orn$^{12}$,Nle$^{17}$,Val$^{26}$,Thr$^{28}$]-VIP cyclo (Glu$^8$→Orn$^{12}$) [Ac-(SEQ ID No:25)-NH$_2$]

Benzhydrylamine copolystyrene-1% divinylbenzene cross-linked resin (25.0 g, 17.5 mequiv, 200–400 ASTM mesh, Bachem) was swelled in 160 mL methylene chloride, filtered and washed using steps 7–8 of the protocol in Table 1. The resin was resuspended in 160 mL methylene chloride and to this was added Boc-Thr(Bzl) (16.2 g, 52.5 mmole) and dicyclohexylcarbodiimide (5.4 g, 26.2 mmol). This mixture was shaken for 6 hours at room temperature, filtered and then steps 10–14 of protocol 1 were performed. Kaiser ninhydrin analysis was negative. Unreacted amine groups were capped by treating the resin with 5 mL acetic anhydride and 5 mL DIPEA in 150 mL methylene chloride for 60 minutes, filtered and washed with protocol steps 13–14. The resin was dried under vacuum overnight to yield 29.6 g of Boc-Thr(Bzl)-BHA resin. A portion of this resin was subjected to amino acid analysis which indicated a loading of 0.21 mmol Thr/g.

A 14.0 g (2.94 mmol) portion of this resin was subjected to solid phase synthesis using the above protocol as in Example 2. Eleven coupling cycles were performed of one cycle each with Boc-Leu (5.9 g, 23.5 mmol), Boc-Val (5.1 g, 23.5 mmol), Boc-Ser(Bzl) (6.9 g, 23.5 mmol), Boc-Asn (3.0 g, 13.0 mmol), Boc-Leu (5.9 g, 23.5 mmol) Boc-Tyr (2,6-DCB) (10.3 g, 23.5 mmol), Boc-Lys(2-Cl-Z) (9.8 g, 23.5 mmol), Boc-Lys(2-Cl-Z) (9.8 g, 23.5 mmol), Boc-Val (5.1 g, 23.5 mmol), Boc-Ala (4.4 g, 23.5 mmol), and Boc-Nle (5.4 g, 23.5 mmol) to give 26 g of Boc-decapeptide resin.

A 5.5 g (0.61 mmol) portion of this resin was coupled with four cycles of one cycle each with Boc-Gln (655 mg, 2.7 mmol), Boc-Lys(2-Cl-Z) (2.0 g, 4.8 mmol), Boc-Arg(Tos) (2.1 g, 4.8 mmol), and Boc-Leu (1.2 g, 4.8 mmol). The resin was dried under vacuum to give 6.12 g of Boc-hexadecapeptide resin.

A 2.0 g (0.2 mmol) portion of this resin was carried through twelve coupling cycles of one cycle each with Boc-Orn(Fmoc) (91 mg, 0.2 mmol), Boc-Thr(Bzl) (250 mg, 0.8 mmol), Boc-Tyr(2,6-DCB) (352 mg, 0.8 mmol), Boc-Asn (102 mg, 0.44 mmol), Boc-Glu(OFm) (340 mg, 0.8 mmol), Boc-Thr(Bzl) (248 mg, 0.8 mmol), Boc-Phe (212 mg, 0.8 mmol), Boc-Val (174 mg, 0.8 mmol), Boc-Ala (152 mg, 0.8 mmol), Boc-Asp(OcHx) (252 mg, 0.8 mmol), Boc-Ser(Bzl) (236 mg, 0.8 mmol), and Boc-His(Bom) (150 mg, 0.4 mmol). The peptide resin was carried through steps 1–8 of protocol 1 and treated with 0.5 mL acetic anhydride and 38 mL DIPEA in 30 mL methylene chloride for 180 minutes. The resin was washed using steps 10–14 and dried under vacuum to yield 2.4 g.

A 1.15 g (0.1 mmol) portion of this resin was then selectively deblocked by treating with steps 1–11 of protocol 2 and reacted twice with BOP (58 mg, 0.13 mmol) and 400 mL DIPEA in 20 mL distilled DMF for 24 and 6 hours. Kaiser ninhydrin analysis was negative. The resin was washed using steps 13–16 of protocol 2 and dried under vacuum to give 1.05 g.

This resin was deblocked by treatment with 9 mL HF, 1 mL anisole, and 100 mL ethanedithiol for 1 hr at 0° C. The reaction mixture was evaporated and the residue was washed with 2×15 mL Et$_2$O and 2×15 mL EtOAc. The resin was extracted with 4×20 mL 10% AcOH. The combined aqueous filtrates were lyophilized to yield 385 mg of a light, yellow solid.

This crude material was purified by gel filtration on SEPHADEX G-25 fine as in Example 3 to give 134 mg of semipurified product. This material was further purified by preparative HPLC as in Example 3 except that a linear gradient of 26–36% in 3 hours was run. The main peak was cut by analytical HPLC analysis of collected fractions, pooled and lyophilized to yield 23.2 mg of a white, amorphous powder. This compound was homogeneous by HPLC and gave a correct amino acid analysis. FAB-MS: MH calc. 3277.8, found 3276.3.

EXAMPLE 8

Preparation of Ac-[Lys$^{12}$,Glu$^{16}$,Nle$^{17}$,Val$^{26}$,Thr$^{28}$]-VIP cyclo (Lys$^{12}$→Glu$^{16}$) [Ac-(SEQ ID No:26)-NH$_2$]

Benzhydrylamine copolystyrene-1% divinylbenzene cross-linked resin (30 g, 21.4 mequiv, 200–400 ASTM mesh, Bachem) was treated as in Example 22 except that 19.9 g Boc-Thr(Bzl) (64.3 mmole) and 6.6 g dicyclohexylcarbodiimide (32.1 mmol)were used. This mixture was shaken for 18 hours at room temperature, filtered and then steps 10–14 of protocol 1 were performed. Kaiser ninhydrin analysis was negative. Unreacted amine groups were capped by treating the resin with 8 mL acetic anhydride and 8 mL DIPEA in 200 mL methylene chloride for 60 minutes, filtered and washed with protocol steps 13–14. The resin was dried under vacuum overnight to yield 34.2 g of Boc-Thr (Bzl)-BHA resin. A portion of this resin was subjected to amino acid analysis which indicated a loading of 0.47 mmol Thr/g.

A 0.85 g (0.4 mmol) portion of this Boc-Thr(Bzl)-BHA resin was subjected to solid phase synthesis on an Applied Biosystems model 430A peptide synthesizer. All couplings were performed using preformed symmetrical anhydrides prepared from Boc-amino acid and dicyclohexylcarbodiimide. Boc-asparagine, Boc-glutamine, and Boc-arginine (tosyl) were routinely coupled as the respective HOBT active esters. Eleven coupling cycles were performed of one cycle each with Boc-Leu (499 mg, 2.0 mmol), Boc-Val (435 mg, 2.0 mmol), Boc-Ser(Bzl) (590 mg, 2.0 mmol), Boc-Asn (464 mg, 2.0 mmol), Boc-Leu (499 mg, 2.0 mmol), Boc-Tyr(2,6-DCB) (880 mg, 2.0 mmol), Boc-Lys(2-Cl-Z) (830 mg, 2.0 mmol), Boc-Lys(2-Cl-Z) (830 mg, 2.0 mmol), Boc-Val (435 mg, 2.0 mmol), Boc-Ala (378 mg, 2.0 mmol), and Boc-Nle (462 mg, 2.0 mmol) to give the Boc-dodecapeptide resin.

This resin was then carried through five coupling cycles, as in Example 2, of one cycle each with Boc-Glu(OFm) (340 mg, 0.8 mmol), Boc-Lys(2-Cl-Z) (664 mg, 1.6 mmol), Boc-Arg(Tos) (685 mg, 1.6 mmol), Boc-Leu (398 mg, 1.6 mmol), and Boc-Lys(Fmoc) (375 mg, 0.8 mmol). The resin was dried under vacuum to give 2.12 g of Boc-heptadecapeptide resin.

A 1.06 g (0.2 mmol) portion of this resin was then selectively deblocked by treating with steps 1–11 of protocol 2 and reacted twice with BOP (177 mg, 0.4 mmol) and 200 mL DIPEA in 20 mL distilled DMF for 2 and 8 hours. Kaiser ninhydrin analysis was very slightly positive. Unreacted amine groups were capped by treating the resin with 0.5 mL acetic anhydride in 20 mL 6% DIPEA/methylene chloride for 10 minutes, filtered and washed with protocol 2 steps 13–16. This resin was then carried through one coupling cycle with Boc-Thr(Bzl) (495 mg, 1.6 mmol) and then placed back on the APPLIED BIOSYSTEMS 430A peptide synthesizer as above. Ten coupling cycles were performed of one cycle each with Boc-Tyr(2,6-DCB) (880 mg, 2.0 mmol), Boc-Asn (464 mg, 2.0 mmol), Boc-Asp(OcHx) (630 mg, 2.0 mmol), Boc-Thr(Bzl) (618 mg, 2.0 mmol), Boc-Phe (531 mg, 2.0 mmol), Boc-Val (435 mg, 2.0 mmol), Boc-Ala (378 mg, 2.0 mmol), Boc-Asp(OcHx) (630 mg, 2.0 mmol), Boc-Ser(Bzl) (590 mg, 2.0 mmol), and Boc-His(Tos) (819 mg, 2.0 mmol). The peptide-resin was then carried through steps 1–8 of protocol 1 and reacted with 0.5 mL acetic anhydride and 100 mL DIPEA in 20 mL methylene chloride for 30 minutes. The resin was washed using steps 10–14 and dried under vacuum.

The peptide-resin was deblocked as in Example 7 to yield 340 mg of crude peptide. The peptide was purified by gel filtration as in Example 3 to yield 35 mg of semi-pure product. This material was further purified by preparative HPLC as in Example 3, except that a linear gradient of 25–35% was run, to yield 15.6 mg of a white, amorphous powder. The compound was homogeneous by HPLC and gave a correct amino acid analysis. FAB-MS: MH calc. 3276.6, found 3278.0.

EXAMPLE 9

Preparation of Ac-[Lys$^{12}$,Nle$^{17}$,Asp$^{24}$,Val$^{26}$,Thr$^{28}$]-VIP cyclo (Lys$^{20}$→Asp$^{24}$) [Ac-(SEQ ID No:27)-NH$_2$]

A 0.42 g (0.2 mmol) portion of the Boc-Thr(Bzl) resin from Example 8 was carried through nine coupling cycles of one cycle each with Boc-Leu (200 mg, 0.8 mmol), Boc-Val (174 mg, 0.8 mmol), Boc-Ser(Bzl) (236 mg, 0.8 mmol), Boc-Asp(OFm) (329 mg, 0.8 mmol), Boc-Leu (200 mg, 0.8 mmol), Boc-Tyr(2,6-DCB) (352 mg, 0.8 mmol), Boc-Lys (2-Cl-Z) (332 mg, 0.8 mmol), Boc-Lys(Fmoc) (375 mg, 0.8 mmol), and Boc-Val (174 mg, 0.8 mmol).

This resin was then selectively deblocked by treating with steps 1–11of protocol 2 and reacted with BOP (177 mg, 0.4 mmol) and 200 mL DIPEA in 20 mL distilled DMF for 6 hours. Kaiser ninhydrin analysis was negative.

This resin was then subjected to solid phase synthesis on an APPLIED BIOSYSTEMS model 430A peptide synthesizer as in Example 8. Seventeen coupling cycles were performed of one cycle each with Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Asp(OcHx) (630 mg, 2.0 mmol), Boc-Thr(Bzl) (618 mg, 2.0 mmol), Boc-Phe (531 mg, 2.0 mmol), Boc-Val (435 mg, 2.0 mmol), Boc-Ala (378 mg, 2.0 mmol), Boc-Asp(OcHx) (630 mg, 2.0 mmol), and Boc-Ser(Bzl) (590 mg, 2.0 mmol). This resin was carried through one coupling cycle with Boc-His(Tos) (164 mg, 0.4 mmol) and then carried through steps 1–8 of protocol 1 and treated with 1 mL acetic anhydride in 20 mL 6% DIPEA/methylene chloride for 30 minutes. The resin was washed using steps 10–14 of protocol 1 and dried under vacuum to yield 1.94 g.

A 0.97 g (0.1 mmol) portion of this peptide-resin was deblocked as in Example 7 to yield 265 mg of crude peptide. The peptide was purified by gel filtration as in Example 3 to yield 149 mg of semi-pure product. This material was further purified by preparative HPLC as in Example 3, except that a linear gradient of 25–35% was run, to yield 28.1 mg of a white, amorphous powder. The compound was homogeneous by HPLC and gave a correct amino acid analysis. FAB-MS: MH calc. 3278.6, found 3278.8.

EXAMPLE 10

Preparation of Ac-[Lys$^{12}$,Nle$^{17}$,Asp$^{25}$,Val$^{26}$,Thr$^{28}$]-VIP cyclo (Lys$^{21}$→Asp$^{25}$) [Ac-(SEQ ID No:28)-NH$_2$]

Benzhydrylamine copolystyrene-1% divinylbenzene cross-linked resin (5.0 g, 2.6 mequiv, 200–400 ASTM mesh, Vega Biochem) was swelled in 50 mL methylene chloride, filtered and washed using steps 7–8 of protocol 1. The resin was resuspended in 60 mL methylene chloride and to this was added Boc-Thr(Bzl) (2.32 g, 7.5 mmole) and dicyclohexylcarbodiimide (774 mg, 3.75 mmol). This mixture was shaken for 4 hours at room temperature, filtered and then steps 10–14 of protocol 1 were performed. Kaiser ninhydrin analysis was negative. Any unreacted amine groups were capped by treating the resin with 5 mL acetic anhydride and 5 mL DIPEA in 50 mL methylene chloride for 60 minutes, filtered and washed with protocol steps 13–14. The resin was dried under vacuum overnight to yield 5.8 g of Boc-Thr (Bzl)-BHA resin. A portion of this resin was subjected to amino acid analysis which indicated a loading of 0.276 mmol Thr/g.

A 1.44 g (0.4 mmol) portion of this resin was subjected to solid phase synthesis using the above protocol 1 as in Example 2. Three coupling cycles were performed of one cycle each with Boc-Leu (399 mg, 1.6 mmol), Boc-Val (348 mg, 1.6 mmol), and Boc-Asp(OFm) (329 mg, 0.8 mmol). One half of this resin (0.2 mmol) was carried through four coupling cycles of one cycle each with Boc-Asn (204 mg, 0.88 mmol), Boc-Leu (199 mg, 0.8 mmol) Boc-Tyr(2,6-DCB) (352 mg, 0.8 mmol), and Boc-Lys(Fmoc) (375 g, 0.8 mmol).

This resin was then selectively deblocked by treating with steps 1–11 of protocol 2 and reacted with BOP (177 mg, 0.4 mmol) in 20 mL 1% DIPEA/DMF for 2 hours. Kaiser ninhydrin analysis was negative.

This resin was carried through one coupling cycle with Boc-Lys(2-Cl-Z) (332 mg, 0.8 mmol) and then subjected to solid phase synthesis on an APPLIED BIOSYSTEMS model 430A peptide synthesizer as in Example 8. Nineteen coupling cycles were performed of one cycle each with Boc-Val (435 mg, 2.0 mmol), Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2, 6-DCB) (880 mg, 2.0 mmol), Boc-Asn (464 mg, 2.0 mmol), Boc-Asp(OcHx) (630 mg, 2.0 mmol), Boc-Thr(Bzl) (618 mg, 2.0 mmol), Boc-Phe (531 mg, 2.0 mmol), Boc-Val (435 mg, 2.0 mmol), Boc-Ala (378 mg, 2.0 mmol), Boc-Asp(OcHx) (630 mg, 2.0 mmol), Boc-Ser(Bzl) (590 mg, 2.0 mmol), and Boc-His(Tos) (819 mg, 2.0 mmol) and then carried through steps 1–8 of protocol 1 and treated with 1 mL acetic anhydride in 20 mL 6% DIPEA/methylene chloride for 30 minutes. The resin was washed using steps 10–14 of protocol 1 and dried under vacuum.

This peptide-resin was deblocked as in Example 7 to yield 210 mg of crude peptide. The peptide was purified by gel filtration as in Example 3 to yield 93 mg of semi-pure product. This material was further purified by preparative HPLC as in Example 3, except that a linear gradient of 27–37% was run, to yield 26.2 mg of a white, amorphous powder. The compound was homogeneous by HPLC and gave a correct amino acid analysis. FAB-MS: MH calc. 3305.8, found 3305.8.

EXAMPLE 11

Preparation of Ac-[$Lys^{12}$,$Nle^{17}$,$Ala^{19}$,$Asp^{25}$,$Val^{26}$,$Thr^{28}$]-VIP cyclo ($Lys^{21} \rightarrow Asp^{25}$) [Ac-(SEQ ID No:29)-$NH_2$]

A 0.4 g (0.1 mmol) portion of benzhydrylamine resin (100–200 ASTM mesh, Bachem) was subjected to solid phase synthesis using the above stated protocol. All couplings were performed using equal molar equivalents of Boc-amino acid and diisopropylcarbodiimide. Boc-asparagine and Boc-glutamine were incorporated as the respective active esters by addition of 1.5 molar excess HOBT to the coupling mixture. Reaction times were generally 2–18 hours for completion of the coupling step. Nine coupling cycles were performed of one cycle each with Boc-Thr(Bzl) (309 mg, 1.0 mmol) Boc-Leu (249 mg, 1.0 mmol), Boc-Val (217 mg, 1.0 mmol), Boc-Asp(OFm) (206 mg, 0.5 mmol), Boc-Asn (232 mg, 1.0 mmol), Boc-Leu (249 mg, 1.0 mmol), Boc-Tyr(2,6-DCB) (440 mg, 1.0 mmol), Boc-Lys(Fmoc) (234 mg, 0.5 mmol), and Boc-Lys(2-Cl-Z) (415 mg, 1.0 mmol).

This resin was then selectively deblocked by treating with steps 1–11 of protocol 2 and reacted with BOP (88 mg, 0.2 mmol) in 20 mL 1% DIPEA/DMF for 2 hours. Kaiser ninhydrin analysis was negative.

Nineteen coupling cycles were performed of one cycle each with Boc-Ala (189 mg, 1.0 mmol), Boc-Ala (189 mg, 1.0 mmol), Boc-Nle (231 mg, 1.0 mmol), Boc-Gln (246 mg, 1.0 mmol), Boc-Lys(2-Cl-Z) (415 mg, 1.0 mmol), Boc-Arg (Tos) (428 mg, 1.0 mmol), Boc-Leu (249 mg, 1.0 mmol), Boc-Lys(2-Cl-Z) (415 mg, 1.0 mmol), Boc-Thr(Bzl) (309 mg, 1.0 mmol), Boc-Tyr(2,6-DCB) (440 mg, 1.0 mmol), Boc-Asn (232 mg, 1.0 mmol), Boc-Asp(OcHx) (315 mg, 1.0 mmol), Boc-Thr(Bzl) (309 mg, 1.0 mmol), Boc-Phe (265 mg, 1.0 mmol), Boc-Val (217 mg, 1.0 mmol), Boc-Ala (189 mg, 1.0 mmol), Boc-Asp(OcHx) (315 mg, 1.0 mmol), Boc-Ser(Bzl) (295 mg, 1.0 mmol), and Boc-His(Tos) (409 mg, 1.0 mmol). The peptide-resin was then carried through steps 1–8 of protocol 1 and treated with 0.5 ml acetic anhydride in 10 mL 6% DIPEA/methylene chloride for 30 minutes. The resin was washed using steps 10–14 and dried under vacuum.

This peptide-resin was deblocked as in Example 7 to yield 304 mg of crude peptide. The peptide was purified by gel filtration as in Example 3 to yield 215 mg of semi-pure product. This material was further purified by preparative HPLC as in Example 3, except that a linear gradient of 26–36% was run, to yield 20.1 mg of a white, amorphous powder. The compound was homogeneous by HPLC and gave a correct amino acid analysis. FAB-MS: MH calc. 3277.6, found 3277.7.

EXAMPLE 12

Preparation of Ac-[p-F-$Phe^6$,2-$Nal^{10}$,$Lys^{12}$,$Nle^{17}$,$Asp^{25}$, $Val^{26}$,$Thr^{28}$,$Gly^{29,30}$,$Met^{31}$]-VIP (1-31)-$NH_2$ cyclo ($Lys^{21} \rightarrow Asp^{25}$) [Ac-(SEQ ID No:30)-$NH_2$]

A 0.4 g (0.1 mmol) portion of benzhydrylamine resin (100–200 ASTM mesh, Bachem) was subjected to solid phase synthesis as in Example 11. Three coupling cycles were performed of one cycle each with Boc-Met (249 mg, 1.0 mmol), Boc-Gly (175 mg, 1.0 mmol), and Boc-Gly (175 mg, 1.0 mmol). Nine coupling cycles and the cyclization were performed as in Example 11. Nineteen coupling cycles were performed as in Example 11 except that Boc-Ala in the tenth cycle was replaced by Boc-Val (217 mg, 1.0 mmol), Boc-Tyr(2,6-DCB) in the nineteenth cycle was replaced by Boc-2-Nal (158 mg, 0.5 mmol), and Boc-Phe in the twenty-third cycle was replaced by Boc-p-F-Phe (142 mg, 0.5 mmol).

This peptide-resin was deblocked as in Example 7 to yield 345 mg of crude peptide. The peptide was purified by gel filtration as in Example 3 to yield 215 mg of semi-pure product. This material was further purified by preparative HPLC as in Example 3, except that a linear gradient of 30–40% was run, to yield 16.4 mg of a white, amorphous powder. The compound was homogeneous by HPLC and gave a correct amino acid analysis. FAB-MS: MH calc. 3574.7, found 3575.1.

EXAMPLE 13

Preparation of Ac-[$Glu^8$,$Orn^{12}$,$Nle^{17}$,$Asp^{25}$,$Val^{26}$,$Thr^{28}$]-VIP cyclo ($Lys^{21} \rightarrow Asp^{25}$) [Ac-(SEQ ID No:31)-$NH_2$]

A 0.4 g (0.1 mmol) portion of benzhydrylamine resin (100–200 ASTM mesh, Bachem) was subjected to solid phase synthesis as in Example 11. Nine coupling cycles and the cyclization were performed as in Example 11. Nineteen coupling cycles were performed as in Example 11 except that Boc-Ala in the tenth cycle was replaced by Boc-Val (217 mg, 1.0 mmol), Boc-Lys(2-Cl-Z) in the seventeenth cycle was replaced by Boc-Orn(Z) (366 mg, 1.0 mmol), and Boc-Asp(OcHx) in the twenty-first cycle was replaced by Boc-Glu(Bzl) (337 mg, 1.0 mmol).

This peptide-resin was deblocked as in Example 7 to yield 255 mg of crude peptide. The peptide was purified by gel filtration as in Example 3 to yield 200 mg of semi-pure product. This material was further purified by preparative HPLC as in Example 3, except that a linear gradient of 28–38% was run, to yield 30.7 mg of a white, amorphous powder. The compound was homogeneous by HPLC and gave a correct amino acid analysis. FAB-MS: MH calc. 3305.8, found 3305.5.

EXAMPLE 14

Preparation of Ac-[p-F-$Phe^6$,$Lys^{12}$,$Nle^{17}$,$Ala^{19}$,$Asp^{25}$,$Val^{26}$, $Thr^{28}$,$Gly^{29,30}$,$Cys(Acm)^{31}$]-VIP (1-31)-$NH_2$ cyclo ($Lys^{21} \rightarrow Asp^{25}$) [Ac-(SEQ ID No:32)-$NH_2$]

Benzhydrylamine resin (0.4 g, 0.1 mmol, 100–200 ASTM mesh, Bachem) was subjected to solid phase synthesis as in Example 11. Three coupling cycles were performed of one cycle each with Boc-Cys(Acm) (292 mg, 1.0 mmol), Boc-Gly (175 mg, 1.0 mmol), and Boc-Gly (175 mg, 1.0 mmol). Nine coupling cycles and cyclization were performed as in Example 11. Nineteen coupling cycles were performed as in Example 11 except that Boc-Phe in the twenty-third cycle was replaced by Boc-p-F-Phe (142 mg, 0.5 mmol).

This peptide-resin was deblocked as in Example 7 to yield 268 mg of crude peptide. The peptide was purified by gel filtration as in Example 3 to yield 165 mg of semi-pure product. This material was further purified by preparative HPLC as in Example 3, except that a linear gradient of 25–35% was run, to yield 28.1 mg of a white, amorphous powder. The compound was homogeneous by HPLC and gave a correct amino acid analysis. FAB-MS: MH calc. 3584.1, found 3584.0.

EXAMPLE 15

Preparation of Ac-[Ala$^2$,Lys$^{12}$,Nle$^{17}$,Ala$^{19}$,Asp$^{25}$,Val$^{26}$, Thr$^{28}$]-VIP cyclo (Lys$^{21}$→Asp$^{25}$) [Ac-(SEQ ID No:33)-NH$_2$]

Benzhydrylamine resin (1.5 g, 0.4 mmol, 100–200 ASTM mesh, Bachem) was subjected to solid phase synthesis on an Applied Biosystems model 430A peptide synthesizer as in Example 11. Eight coupling cycles were performed of one cycle each with Boc-Thr(Bzl) (619 mg, 2.0 mmol), Boc-Leu (499 mg, 2.0 mmol), Boc-Val (435 mg, 2.0 mmol), Boc-Asp(OFm) (822 mg, 2.0 mmol), Boc-Asn (464 mg, 2.0 mmol), Boc-Leu (499 mg, 2.0 mmol), Boc-Tyr(2,6-DCB) (880 mg, 2.0 mmol), and Boc-Lys(Fmoc) (938 mg, 2.0 mmol).

This resin was then selectively deblocked by treating with steps 1–11 of protocol 2 and reacted with BOP (356 mg, 0.8 mmol) in 20 mL 1% DIPEA/DMF for 2 hours. Kaiser ninhydrin analysis was negative. The resin was washed using steps 13–16 of protocol 2 and dried under vacuum to yield 1.9 g of Boc-octapeptide resin.

A 0.95 g (0.2 mmol) portion of this resin was again subjected to solid phase synthesis on an APPLIED BIOSYSTEMS model 430A peptide synthesizer as in Example 11. Eighteen coupling cycles were performed of one cycle each with Boc-Lys(2-Cl-Z) (830 mg, 2.0 mmol), Boc-Ala (378 mg, 2.0 mmol), Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Asp(OcHx) (630 mg, 2.0 mmol), Boc-Thr (Bzl) (618 mg, 2.0 mmol), Boc-Phe (531 mg, 2.0 mmol), Boc-Val (435 mg, 2.0 mmol), Boc-Ala (378 mg, 2.0 mmol), and Boc-Asp(OcHx) (630 mg, 2.0 mmol) to give 1.54 g of Boc-hexacosapeptide resin.

A 0.77 g (0.1 mmol) portion of this resin was subjected to solid phase synthesis using the above protocol as in Example 2. Two coupling cycles were performed of one cycle each with Boc-Ala (76 mg, 0.4 mmol) and Boc-His(Tos) (328 mg, 0.8 mmol). The peptide resin was carried through steps 1–8 of protocol 1 and treated with 0.5 mL acetic anhydride in 20 mL 6% DIPEA/methylene chloride for 60 minutes. The resin was washed using steps 10–14 and dried under vacuum to give 0.74 g.

This peptide-resin was deblocked as in Example 7 to yield 172 mg of crude peptide. The peptide was purified by gel filtration as in Example 3 to yield 110 mg of semi-pure product. This material was further purified by preparative HPLC as in Example 3, except that a linear gradient of 22–37% was run, to yield 40.0 mg of a white, amorphous powder. The compound was homogeneous by HPLC and gave a correct amino acid analysis. FAB-MS: MH calc. 3261.7, found 3261.8.

EXAMPLE 16

Preparation of Ac-[N-Me-Ala$^1$,Lys$^{12}$,Nle$^{17}$,Ala$^{19}$,Asp$^{25}$, Val$^{26}$,Thr$^{28}$]-VIP cyclo (Lys$^{21}$→Asp$^{25}$) [Ac-(SEQ ID No:34)-NH$_2$]

A 0.77 g (0.1 mmol) portion of the Boc-hexaocosapeptide resin from Example 15 was subjected to solid phase synthesis using the above protocol as in Example 2. Two coupling cycles were performed of one cycle each with Boc-Ser(Bzl) (118 mg, 0.4 mmol) and Boc-N-Me-Ala (81 mg, 0.4 mmol). The peptide resin was carried through steps 1–8 of protocol 1 and treated with BOP (442 mg, 1.0 mmol), acetic acid (57 mL, 1.0 mmol), and DIPEA (523 mL, 3.0 mmol) in 20 mL DMF for 6 hours and then with 0.5 mL acetic anhydride in 20 mL 6% DIPEA/methylene chloride for 60 minutes. The resin was washed using steps 10–14 and dried under vacuum to give 0.73 g.

This peptide-resin was deblocked as in Example 7 to yield 191 mg of crude peptide. The peptide was purified by gel filtration as in Example 3 to yield 138 mg of semi-pure product. This material was further purified by preparative HPLC as in Example 3, except that a linear gradient of 22–37% was run, to yield 28.0 mg of a white, amorphous powder. The compound was homogeneous by HPLC and gave a correct amino acid analysis. FAB-MS: MH calc. 3225.4, found 3225.8.

EXAMPLE 17

Preparation of Ac-[2-Nal$^{10}$,Leu$^{12}$,Nle$^{17}$,Ala$^{19}$,Asp$^{25}$,Val$^{26}$, Thr$^{28}$]-VIP cyclo (Lys$^{21}$→Asp$^{25}$) [Ac-(SEQ ID No:35)-NH$_2$]

Benzhydrylamine resin (4.0 g, 1.08 mmol, 100–200 ASTM mesh, Bachem) was subjected to solid phase synthesis using protocol 1 as in Example 2. Eight coupling cycles were performed of one cycle each with Boc-Thr(Bzl) (1.34 g, 4.3 mmol), Boc-Leu (925 mg, 4.3 mmol), Boc-Val (938 mg, 4.3 mmol), Boc-Asp(OFm) (889 mg, 2.1 mmol), Boc-Asn (557 mg, 2.4 mmol), Boc-Leu (925 mg, 4.3 mmol), Boc-Tyr(2,6-DCB) (1.9 g, 4.3 mmol), and Boc-Lys(Fmoc) (1.1 g, 4.3 mmol).

This resin was then selectively deblocked by treating with steps 1–11 of protocol 2 and reacted with BOP (885 mg, 2.0 mmol) in 20 mL 1% DIPEA/DMF for 2 hours. Kaiser ninhydrin analysis was negative. The resin was washed using steps 13–16 of protocol 2.

This resin was carried through one coupling cycle with Boc-Lys(2-Cl-Z) (1.79 g, 4.3 mmol) and dried under vacuum to give 6.3 g of Boc-nonapeptide resin.

A 1.89 g (0.3 mmol) portion of this resin was carried through nine coupling cycles of one cycle each with Boc-Ala (227 mg, 1.2 mmol), Boc-Ala (227 mg, 1.2 mmol), Boc-Nle (278 mg, 1.2 mmol), Boc-Gln (325 mg, 1.32 mmol), Boc-Lys(2-Cl-Z) (498 mg, 1.2 mmol), Boc-Arg(Tos) (514 mg, 1.2 mmol), Boc-Leu (299 mg, 1.2 mmol), Boc-Leu (498 mg, 2.0 mmol), and Boc-Thr(Bzl) (371 mg, 1.2 mmol) to give 2.06 g of Boc-octadecapeptide resin.

A 0.68 g (0.1 mmol) portion of this resin was carried through ten coupling cycles of one cycle each with Boc-2-Nal (126 mg, 0.4 mmol), Boc-Asn (102 mg, 0.44 mmol), Boc-Asp(OcHx) (126 mg, 0.4 mmol), Boc-Thr(Bzl) (124 mg, 0.4 mmol), Boc-Phe (106 mg, 0.4 mmol), Boc-Val (87 mg, 0.4 mmol), Boc-Ala (76 mg, 0.4 mmol), Boc-Asp (OcHx) (126 mg, 0.4 mmol), Boc-Ser(Bzl) (118 mg, 0.4 mmol), and Boc-His(Tos) (164 mg, 0.4 mmol). The peptide resin was carried through steps 1–8 of protocol 1 and treated with 0.5 mL acetic anhydride in 20 mL 6% DIPEA/methylene chloride for 60 minutes. The resin was washed using steps 10–14 and dried under vacuum to give 0.82 g.

This peptide-resin was deblocked as in Example 7 to yield 261 mg of crude peptide. The peptide was purified by gel filtration as in Example 3 to yield 186 mg of semi-pure product. This material was further purified by preparative HPLC as in Example 3, except that a linear gradient of 30–40% was run, to yield 60.1 mg of a white, amorphous powder. The compound was homogeneous by HPLC and gave a correct amino acid analysis. FAB-MS: MH calc. 3296.8, found 3295.6.

EXAMPLE 18

Preparation of Ac-[O-Me-Tyr$^{10}$,Leu$^{12}$,Nle$^{17}$,Ala$^{19}$,Asp$^{25}$, Val$^{26}$,Thr$^{28}$]-VIP cyclo (Lys$^{21}$→Asp$^{25}$) [Ac-(SEQ ID No:36)-NH$_2$]

A 0.68 g (0.1 mmol) portion of the Boc-octadecapeptide resin from Example 17 was carried through ten coupling cycles as in Example 17 except that Boc-2-Nal in the nineteenth cycle was replaced by Boc-Tyr(O-Me) (59 mg, 0.2 mmol) to give 0.61 g.

This peptide-resin was deblocked as in Example 7 to yield 175 mg of crude peptide. The peptide was purified by gel filtration as in Example 3 to yield 136 mg of semi-pure product. This material was further purified by preparative HPLC as in Example 3, except that a linear gradient of 28–38% was run, to yield 42.4 mg of a white, amorphous powder. The compound was homogeneous by HPLC and gave a correct amino acid analysis. FAB-MS: MH calc. 3276.7, found 3276.0.

EXAMPLE 19

Preparation of Ac-[p-F-Phe$^6$,p-NH$_2$-Phe$^{10}$,Leu$^{12}$,Nle$^{17}$, Ala$^{19}$,Asp$^{25}$,Val$^{26}$,Thr$^{28}$]-VIP cyclo (Lys$^{21}$→Asp$^{25}$) [Ac-(SEQ ID No:37)-NH$_2$]

A 0.625 g (0.09 mmol) portion of the Boc-octadecapeptide resin was carried through ten coupling cycles as in Example 17 except that Boc-2-Nal in the nineteenth cycle was replaced by Boc-p-NH(Z)-Phe (166 mg, 0.4 mmol) and Boc-Phe in the twenty-third cycle was replaced by Boc-p-F-Phe (113 mg, 0.4 mmol) to give 0.84 g.

This peptide-resin was deblocked as in Example 7 to yield 182 mg of crude peptide. The peptide was purified by gel filtration as in Example 3 to yield 160 mg of semi-pure product. This material was further purified by preparative HPLC as in Example 3, except that a linear gradient of 25–35% was run, to yield 47.2 mg of a white, amorphous powder. The compound was homogeneous by HPLC and gave a correct amino acid analysis. FAB-MS: MH calc. 3279.7, found 3279.8.

EXAMPLE 20

Preparation of Ac-[Lys$^{12}$,Nle$^{17}$,Ala$^{19}$,Asp$^{25}$,Leu$^{26}$,Lys$^{27,28}$]-VIP cyclo (Lys$^{21}$→Asp$^{25}$) [Ac-(SEQ ID No:38)-NH$_2$]

Benzhydrylamine resin (1.25 g, 1.0 mmol, 100–200 ASTM mesh, Bachem) was subjected to solid phase synthesis using protocol 1 as in Example 2. Eight coupling cycles were performed of one cycle each with Boc-Lys(2-Cl-Z) (1.66 g, 4.0 mmol), Boc-Lys(2-Cl-Z) (1.66 g, 4.0 mmol), Boc-Leu (925 mg, 4.0 mmol), Boc-Asp(OFm) (823 mg, 2.0 mmol), Boc-Asn (511 mg, 2.2 mmol), Boc-Leu (925 mg, 4.0 mmol), Boc-Tyr(2,6-DCB) (1.76 g, 4.0 mmol), and Boc-Lys(Fmoc) (937 mg, 2.0 mmol).

This resin was then selectively deblocked by treating with steps 1–11 of protocol 2 and reacted with BOP (885 mg, 2.0 mmol) in 20 mL 1% DIPEA/DMF for 2 hours. Kaiser ninhydrin analysis was negative. The resin was washed using steps 13–16 of protocol 2.

This resin was carried through one coupling cycle with Boc-Lys(2-Cl-Z) (1.66 g, 4.0 mmol) and dried under vacuum to give 2.7 g of Boc-nonapeptide resin.

A 0.54 g (0.2 mmol) portion of this resin was subjected to solid phase synthesis on an APPLIED BIOSYSTEMS model 430A peptide synthesizer as in Example 8. Eighteen coupling cycles were performed of one cycle each with Boc-Ala (378 mg, 2.0 mmol), Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Asp(OcHx) (630 mg, 2.0 mmol), Boc-Thr(Bzl) (618 mg, 2.0 mmol), Boc-Phe (531 mg, 2.0 mmol), Boc-Val (435 mg, 2.0 mmol), Boc-Ala (378 mg, 2.0 mmol), Boc-Asp(OcHx) (630 mg, 2.0 mmol), and Boc-Ser (Bzl) (590 mg, 2.0 mmol) to give 1.16 g of Boc-heptacosapeptide resin.

A 0.54 g (0.1 mmol) portion of this resin was carried through one coupling cycle with Boc-His(Tos) (819 mg, 2.0 mmol) and then carried through steps 1–8 of protocol 1 and treated with 0.5 mL acetic anhydride in 20 mL 6% DIPEA/methylene chloride for 60 minutes. The resin was washed using steps 10–14 of protocol 1 and dried under vacuum to yield 0.5 g.

This peptide-resin was deblocked as in Example 7, except that 5 mL HF and 0.5 mL anisole were used, to yield 127 mg of crude peptide. The peptide was purified by gel filtration as in Example 3 to yield 74.6 mg of semi-pure product. This material was further purified by preparative HPLC as in Example 3, except that a linear gradient of 24–34% was run, to yield 17.1 mg of a white, amorphous powder. The compound was homogeneous by HPLC and gave a correct amino acid analysis. FAB-MS: MH calc. 3333.8, found 3333.4.

EXAMPLE 21

Preparation of Ac-[N-Me-Ala$^1$,Lys$^{12}$,Nle$^{17}$,Ala$^{19}$,Asp$^{25}$, Leu$^{26}$,Lys$^{27,28}$]-VIP cyclo (Lys$^{21}$→Asp$^{25}$) [Ac-(SEQ ID No:39)-NH$_2$]

A 0.58 g (0.1 mmol) portion of the Boc-heptacosapeptide resin from Example 20 was carried through one coupling cycle with Boc-N-Me-Ala (81 mg, 0.4 mmol) and then carried through steps 1–8 of protocol 1 and treated with BOP (443 mg, 1.0 mmol), acetic acid (57 mL, 1.0 mmol), and DIPEA (523 mL, 3.0 mmol) in 20 mL DMF for 6 hours and with 0.5 mL acetic anhydride in 20 mL 6% DIPEA/methylene chloride for 60 minutes. The resin was washed using steps 10–14 of protocol 1 and dried under vacuum to yield 0.4 g.

This peptide-resin was deblocked as in Example 20 to yield 165 mg of crude peptide. The peptide was purified by gel filtration as in Example 3 to yield 101 mg of semi-pure product. This material was further purified by preparative HPLC as in Example 3, except that a linear gradient of 24–34% was run, to yield 19.8 mg of a white, amorphous powder. The compound was homogeneous by HPLC and gave a correct amino acid analysis. FAB-MS: MH calc. 3281.8, found 3281.9.

EXAMPLE 22

Preparation of Ac-[Glu$^8$,Lys$^{12}$,Nle$^{17}$,Ala$^{19}$,Asp$^{25}$,Leu$^{26}$, Lys$^{27,28}$]-VIP cyclo (Lys$^{21}$→Asp$^{25}$) [Ac-(SEQ ID No:40)-NH$_2$]

A 0.54 g (0.2 mmol) portion of the Boc-nonapeptide resin of Example 20 was subjected to solid phase synthesis on an APPLIED BIOSYSTEMS model 430A peptide synthesizer as in Example 8. Eighteen coupling cycles were performed of one cycle each with Boc-Ala (378 mg, 2.0 mmol), Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Glu (OBzl) (675 mg, 2.0 mmol), Boc-Thr(Bzl) (618 mg, 2.0 mmol), Boc-Phe (531 mg, 2.0 mmol), Boc-Val (435 mg, 2.0 mmol), Boc-Ala (378 mg, 2.0 mmol), Boc-Asp(OcHx) (630 mg, 2.0 mmol), and Boc-Ser(Bzl) (590 mg, 2.0 mmol) to give 0.58 g of Boc-heptacosapeptide resin.

This resin was carried through one coupling cycle with Boc-His(Tos) (164 mg, 0.4 mmol) and then carried through steps 1–8 of protocol 1 and treated with 0.5 mL acetic anhydride in 20 mL 6% DIPEA/methylene chloride for 60 minutes. The resin was washed using steps 10–14 of protocol 1 and dried under vacuum to yield 0.53 g.

This peptide-resin was deblocked as in Example 7, except that 5 mL HF and 0.5 mL anisole were used, to yield 151 mg of crude peptide. The peptide was purified by gel filtration as in Example 3 to yield 110 mg of semi-pure product. This material was further purified by preparative HPLC as in Example 3, except that a linear gradient of 23.5–33.5% was run, to yield 22.8 mg of a white, amorphous powder. The compound was homogeneous by HPLC and gave a correct amino acid analysis. FAB-MS: MH calc. 3347.9, found 3347.0.

EXAMPLE 23

Preparation of Ac-[O-Me-Tyr$^{10}$,Lys$^{12}$,Nle$^{17}$,Ala$^{19}$,Asp$^{25}$, Val$^{26}$,Thr$^{28}$]-VIP cyclo (Lys$^{21}$→Asp$^{25}$) [Ac-(SEQ ID No:41)-NH$_2$]

A 1.84 g (0.3 mmol) portion of the Boc-nonapeptide resin from Example 17 was subjected to solid phase synthesis on an APPLIED BIOSYSTEMS model 430A peptide synthesizer as in Example 8. Nine coupling cycles were performed of one cycle each with Boc-Ala (378 mg, 2.0 mmol), Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), and Boc-Thr(Bzl) (618 mg, 2.0 mmol) to give 2.2 g of Boc-octadecapeptide resin.

A 0.73 g (0.1 mmol) portion of this resin was carried through ten coupling cycles of one cycle each with Boc-Tyr (O-Me) (59 mg, 0.2 mmol), Boc-Asn (102 mg, 0.44 mmol), Boc-Asp(OcHx) (126 mg, 0.4 mmol), Boc-Thr(Bzl) (124 mg, 0.4 mmol), Boc-Phe (106 mg, 0.4 mmol), Boc-Val (87 mg, 0.4 mmol), Boc-Ala (76 mg, 0.4 mmol), Boc-Asp (OcHx) (126 mg, 0.4 mmol), Boc-Ser(Bzl) (118 mg, 0.4 mmol), and Boc-His(Tos) (164 mg, 0.4 mmol). The peptide resin was carried through steps 1–8 of protocol 1 and treated with 0.5 mL acetic anhydride in 20 mL 6% DIPEA/methylene chloride for 60 minutes. The resin was washed using steps 10–14 and dried under vacuum to give 0.77 g.

This peptide-resin was deblocked as in Example 7 to yield 187 mg of crude peptide. The peptide was purified by gel filtration as in Example 3 to yield 131 mg of semi-pure product. This material was further purified by preparative HPLC as in Example 3, except that a linear gradient of 26–36% was run, to yield 5.3 mg of a white, amorphous powder. The compound was homogeneous by HPLC and gave a correct amino acid analysis. FAB-MS: MH calc. 3291.8, found 3291.7.

EXAMPLE 24

Preparation of Ac[Glu$^8$,Lys$^{12}$,Nle$^{17}$,Ala$^{19}$,Asp$^{25}$,Leu$^{26}$, Lys$^{27,28}$,Ala$^{29-31}$]-VIP cyclo (Lys$^{21}$→Asp$^{25}$) [Ac-(SEQ ID No:42)-NH$_2$]

Benzhydrylamine resin (1.1 g, 0.5 mmol, 200–400 ASTM mesh, Biomega) was subjected to solid phase synthesis using protocol 1 as in Example 2. Thirteen coupling cycles were performed of one cycle each with Boc-Ala (378 mg, 2.0 mmol), Boc-Ala (378 mg, 2.0 mmol), Boc-Ala (378 mg, 2.0 mmol), Boc-Lys(2-Cl-Z) (830 mg, 2.0 mmol), Boc-Lys (2-Cl-Z) (830 mg, 2.0 mmol), Boc-Leu (499 mg, 2.0 mmol), Boc-Asp(OFm) (823 mg, 2.0 mmol), Boc-Asn (511 mg, 2.2 mmol), Boc-Leu (499 mg, 2.0 mmol), Boc-Tyr(2,6-DCB) (881 mg, 2.0 mmol), Boc-Lys(Fmoc) (936 mg, 2.0 mmol), Boc-Lys(2-Cl-Z) (830 mg, 2.0 mmol), and Boc-Ala (378 mg, 2.0 mmol).

This resin was then selectively deblocked by treating with steps 1–11 of protocol 2 and reacted with BOP (443 mg, 1.0 mmol) in 20 mL 1% DIPEA/DMF for 1 hour. Kaiser ninhydrin analysis was negative. The resin was washed using steps 13–16 of protocol 2 and dried under vacuum to give 2.02 g of Boc-tridecapeptide resin.

A 0.8 g (0.2 mmol) portion of this resin was subjected to solid phase synthesis on an APPLIED BIOSYSTEMS model 430A peptide synthesizer as in Example 8. Sixteen coupling cycles were performed of one cycle each with Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Asp (OcHx) (630 mg, 2.0 mmol), Boc-Thr(Bzl) (618 mg, 2.0 mmol), Boc-Phe (531 mg, 2.0 mmol), Boc-Val (435 mg, 2.0 mmol), Boc-Ala (378 mg, 2.0 mmol), and Boc-Asp(OcHx) (630 mg, 2.0 mmol) to give 1.2 g of Boc-nonacosapeptide resin.

A 0.6 g (0.1 mmol) portion of this resin was carried through two coupling cycles as above with Boc-Ser(Bzl) (590 mg, 2.0 mmol) and Boc-His(Tos) (819 mg, 2.0 mmol) to give 0.72 g. This resin was then carried through steps 1–8 of protocol 1 and treated with 0.5 mL acetic anhydride in 20 mL 6% DIPEA/methylene chloride for 60 minutes. The resin was washed using steps 10–14 of protocol 1 and dried under vacuum to yield 0.645 g.

This peptide-resin was deblocked as in Example 7 to yield 280 mg of crude peptide. The peptide was purified by gel filtration as in Example 3 to yield 160 mg of semi-pure product. This material was further purified by preparative HPLC as in Example 3, except that a linear gradient of 22–32% was run, to yield 23.1 mg of a white, amorphous powder. The compound was homogeneous by HPLC and gave a correct amino acid analysis. FAB-MS: MH calc. 3561.1, found 3560.8.

EXAMPLE 25

Preparation of Ac-[Ala$^2$,Glu$^8$,Lys$^{12}$,Nle$^{17}$,Ala$^{19}$,Asp$^{25}$, Leu$^{26}$,Lys$^{27,28}$,Ala$^{29-31}$]-VIP cyclo (Lys$^{21}$→Asp$^{25}$) [Ac-(SEQ ID No:43)-NH$_2$]

A 0.6 g (0.1 mmol) portion of the Boc-nonacosapeptide resin of Example 24 was carried through two coupling cycles as above with Boc-Ser(Bzl) (590 mg, 2.0 mmol) and Boc-His(Tos) (819 mg, 2.0 mmol) to give 0.68 g. This resin was then carried through steps 1–8 of protocol 1 and treated with 0.5 mL acetic anhydride in 20 mL 6% DIPEA/ methylene chloride for 60 minutes. The resin was washed using steps 10–14 of protocol 1 and dried under vacuum to yield 0.56 g.

This peptide-resin was deblocked as in Example 7 to yield 160 mg of crude peptide. The peptide was purified by gel filtration as in Example 3 to yield 70 mg of semi-pure product. This material was further purified by preparative HPLC as in Example 3, except that a linear gradient of 25–35% was run, to yield 21.8 mg of a white, amorphous powder. The compound was homogeneous by HPLC and gave a correct amino acid analysis. FAB-MS: MH calc. 3545.1, found 3545.3.

EXAMPLE 26

Preparation of Ac-[N-Me-Ala$^1$,Glu$^8$,Lys$^{12}$,Nle$^{17}$,Ala$^{19}$, Asp$^{25}$,Leu$^{26}$,Lys$^{27,28}$]-VIP cyclo (Lys$^{21}$→Asp$^{25}$) [Ac-(SEQ ID No:44)-NH$_2$]

A 1.1 g (0.4 mmol) portion of the Boc-nonapeptide resin of Example 20 was subjected to solid phase synthesis on an APPLIED BIOSYSTEMS model 430A peptide synthesizer as in Example 8. Seventeen coupling cycles were performed of one cycle each with Boc-Ala (378 mg, 2.0 mmol), Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Asp(OcHx) (630 mg, 2.0 mmol), Boc-Thr(Bzl) (618 mg, 2.0 mmol), Boc-Phe (531 mg, 2.0 mmol), Boc-Val (435 mg, 2.0 mmol), Boc-Ala (378 mg, 2.0 mmol), and Boc-Asp(OcHx) (630 mg, 2.0 mmol) to give 2.24 g of Boc-hexacosapeptide resin.

A 1.1 g (0.2 mmol) portion of this resin was carried through two coupling cycle with Boc-Ser(Bzl) (238 mg, 0.8 mmol) and Boc-N-Me-Ala (163 mg, 0.8 mmol) and then carried through steps 1–8 of protocol 1 and treated with BOP-Cl (100 mg, 0.2 mmol), acetic acid (23 mL, 0.2 mmol), and DIPEA (140 mL, 0.4 mmol) in 20 mL DMF for 1 hour. The resin was washed using steps 10–14 of protocol 1 and dried under vacuum to yield 0.95 g.

This peptide-resin was deblocked as in Example 7 to yield 245 mg of crude peptide. The peptide was purified by gel filtration as in Example 3 to yield 165 mg of semi-pure product. This material was further purified by preparative HPLC as in Example 3, except that a linear gradient of 25–35% was run, to yield 33.7 mg of a white, amorphous powder. The compound was homogeneous by HPLC and gave a correct amino acid analysis. FAB-MS: MH calc. 3295.8, found 3294.5.

EXAMPLE 27

Preparation of Ac-[p-F-Phe$^6$,Glu$^8$,Lys$^{12}$,Nle$^{17}$,Ala$^{19}$,Asp$^{25}$, Leu$^{26}$,Lys$^{27,28}$]-VIP cyclo (Lys$^{21}$→Asp$^{25}$) [Ac-(SEQ ID NO:45)-NH$_2$]

Benzhydrylamine resin (2.49 g, 2.0 mmol, 100–200 ASTM mesh, Bachem) was subjected to solid phase synthesis using protocol 1 as in Example 2. Six coupling cycles were performed of one cycle each with Boc-Lys(2-Cl-Z) (3.32 g, 8.0 mmol), Boc-Lys(2-Cl-Z) (3.32 g, 8.0 mmol), Boc-Leu (1.85 g, 8.0 mmol), Boc-Asp(OFm) (823 mg, 2.0 mmol), Boc-Asn (1.02 g, 4.4 mmol), and Boc-Leu (1.05 g, 8.0 mmol). The resin was dried and 0.4 mmoles removed. Three coupling cycles were performed of one cycle each with Boc-Tyr(2,6-DCB) (2.52 g, 6.4 mmol), and Boc-Lys (Fmoc) (1.87 g, 6.4 mmol) and Boc-Lys(2-Cl-Z) (2.65 g, 6.4 mmol).

This resin was then selectively deblocked by treating with steps 1–11 of protocol 2 and reacted with BOP (1.42 g, 3.2 mmol) in 20 mL 1% DIPEA/DMF for 4.5 hours. Kaiser ninhydrin analysis was negative. The resin was washed using steps 13–16 of protocol 2 and dried to give 6.56 g of Boc-nonapeptide resin.

A 1.64 g (0.4 mmol) portion of this resin was subjected to solid phase synthesis on an APPLIED BIOSYSTEMS model 430A peptide synthesizer as in Example 8. Thirteen coupling cycles were performed of one cycle each with Boc-Ala (378 mg, 2.0 mmol), Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Asp(OcHx) (630 mg, 2.0 mmol), and Boc-Thr(Bzl) (618 mg, 2.0 mmol) to give 2.56 g of Boc-docosapeptide resin.

A 0.64 g (0.1 mmol) portion of this resin was carried through six coupling cycles of one cycle each with Boc-p-F-Phe (283 mg, 1.0 mmol), Boc-Val (218 mg, 1.0 mmol), Boc-Ala (189 mg, 1.0 mmol), Boc-Asp(OcHx) (315 mg, 1.0 mmol), Boc-Ser(Bzl) (295 mg, 1.0 mmol), and Boc-His (Tos) (818 mg, 2.0 mmol). The peptide resin was carried through steps 1–8 of protocol 1 and treated with 0.5 mL acetic anhydride in 20 mL 6% DIPEA/methylene chloride for 60 minutes. The resin was washed using steps 10–14 and dried under vacuum to give 0.69 g.

This peptide-resin was deblocked as in Example 7 to yield 224 mg of crude peptide. The peptide was purified by gel filtration as in Example 3 to yield 213 mg of semi-pure product. This material was further purified by preparative HPLC as in Example 3, except that a linear gradient of 27–37% was run, to yield 70.5 mg of a white, amorphous powder. The compound was homogeneous by HPLC and gave a correct amino acid analysis. FAB-MS: MH calc. 3365.9, found 3365.6.

EXAMPLE 28

Preparation of Ac-[1-Nal$^6$,Glu$^8$,Lys$^{12}$,Nle$^{17}$,Ala$^{19}$,Asp$^{25}$, Leu$^{26}$,Lys$^{27,28}$]-VIP cyclo (Lys$^{21}$→Asp$^{25}$) [Ac-(SEQ ID No:46)-NH$_2$]

A 1.28 g (0.2 mmol) portion of the Boc-docosapeptide resin of Example 27 was carried through six coupling cycles as in Example 27 except that Boc-p-F-Phe in the first cycle was replaced by Boc-1-Nal (315 mg, 1.0 mmol). The peptide resin was carried through steps 1–8 of protocol 1 and treated with 0.5 mL acetic anhydride in 20 mL 6% DIPEA/methylene chloride for 60 minutes. The resin was washed using steps 10–14 and dried under vacuum to give 1.41 g.

This peptide-resin was deblocked as in Example 7 to yield 420 mg of crude peptide. The peptide was purified by gel filtration as in Example 3 to yield 305 mg of semi-pure product. This material was further purified by preparative HPLC as in Example 3, except that a linear gradient of 25–35% was run, to yield 66.9 mg of a white, amorphous powder. The compound was homogeneous by HPLC and gave a correct amino acid analysis. FAB-MS: MH calc. 3398.0, found 3398.8.

EXAMPLE 29

Preparation of Ac-[Glu$^8$,p-NH$_2$-Phe$^{10}$,Lys$^{12}$,Nle$^{17}$,Ala$^{19}$, Asp$^{25}$,Leu$^{26}$,Lys$^{27,28}$]-VIP cyclo (Lys$^{21}$→Asp$^{25}$) [Ac-(SEQ ID No:47)-NH$_2$]

A 1.64 g (0.4 mmol) portion of the Boc-nonapeptide resin of Example 27 was subjected to solid phase synthesis on an APPLIED BIOSYSTEMS model 430A peptide synthesizer as in Example 8. Nine coupling cycles were performed of one cycle each with Boc-Ala (378 mg, 2.0 mmol), Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), and Boc-Thr(Bzl) (618 mg, 2.0 mmol) to give 2.2 g of Boc-octadecapeptide resin.

A 1.1 g (0.2 mmol) portion of this resin was carried through ten coupling cycles of one cycle each with Boc-p-NH(CBZ)-Phe (415 mg, 1.0 mmol), Boc-Asn (512 mg, 2.2 mmol), Boc-Glu(Bzl) (675 mg, 2.0 mmol), Boc-Thr(Bzl) (620 mg, 2.0 mmol), Boc-Phe (532 mg, 2.0 mmol), Boc-Val (436 mg, 2.0 mmol), Boc-Ala (378 mg, 2.0 mmol), Boc-Asp(OcHx) (630 mg, 2.0 mmol), Boc-Ser(Bzl) (590 mg, 2.0 mmol), and Boc-His(Tos) (1.64 g, 4.0 mmol). The peptide resin was carried through steps 1–8 of protocol 1 and treated with 0.5 mL acetic anhydride in 20 mL 6% DIPEA/methylene chloride for 60 minutes. The resin was washed using steps 10–14 and dried under vacuum to give 1.45 g.

This peptide-resin was deblocked as in Example 7 to yield 580 mg of crude peptide. The peptide was purified by gel filtration as in Example 3 to yield 400 mg of semi-pure product. This material was further purified by preparative HPLC as in Example 3, except that a linear gradient of 22–32% was run, to yield 60.9 mg of a white, amorphous powder. The compound was homogeneous by HPLC and gave a correct amino acid analysis. FAB-MS: MH calc. 3346.9, found 3346.8.

EXAMPLE 30

Preparation of Ac-[Glu$^8$,O-Me-Tyr$^{10}$,Lys$^{12}$,Nle$^{17}$,Ala$^{19}$, Asp$^{25}$,Leu$^{26,}$Lys$^{27,28}$]-VIP cyclo (Lys$^{21}$→Asp$^{25}$) [Ac-(SEQ ID No:48)-NH$_2$]

A 1.1 g (0.2 mmol) portion of the Boc-octadecapeptide resin of Example 29 was carried through ten coupling cycles as in Example 29 except that Boc-p-NH(CBZ)-Phe in the first cycle was replaced by Boc-O-Me-Tyr (148 mg, 0.5 mmol). The peptide resin was carried through steps 1–8 of protocol 1 and treated with 0.5 mL acetic anhydride in 20 mL 6% DIPEA/methylene chloride for 60 minutes. The resin was washed using steps 10–14 and dried under vacuum to give 1.45 g.

This peptide-resin was deblocked as in Example 7 to yield 555 mg of crude peptide. The peptide was purified by gel filtration as in Example 3 to yield 460 mg of semi-pure product. This material was further purified by preparative HPLC as in Example 3, except that a linear gradient of 25–35% was run, to yield 152.9 mg of a white, amorphous powder. The compound was homogeneous by HPLC and gave a correct amino acid analysis. FAB-MS: MH calc. 3361.9, found 3361.7.

EXAMPLE 31

Preparation of Ac-[p-F-Phe$^6$,Lys$^{12}$,Nle$^{17}$,Ala$^{19}$,Asp$^{25}$,Val$^{26}$, Thr$^{28}$]-VIP cyclo (Lys$^{21}$→Asp$^{25}$) [Ac-(SEQ ID No:49)-NH$_2$]

A 1.2 g (0.2 mmol) portion of the Boc-nonapeptide resin of example 17 was subjected to solid phase synthesis on an Applied Biosystems model 430A peptide synthesizer as in Example 8. Thirteen coupling cycles were performed of one cycle each with Boc-Ala (378 mg, 2.0 mmol), Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Asp(OcHx) (630 mg, 2.0 mmol), and Boc-Thr(Bzl) (618 mg, 2.0 mmol) to give 1.3 g of Boc-docosapeptide resin.

A 0.65 g (0.1 mmol) portion of this resin was carried through six coupling cycles as in Example 27. The peptide resin was carried through steps 1–8 of protocol 1 and treated with 0.5 mL acetic anhydride in 20 mL 6% DIPEA/methylene chloride for 60 minutes. The resin was washed using steps 10–14 and dried under vacuum to give 0.856 g.

This peptide-resin was deblocked as in Example 7 to yield 550 mg of crude peptide. The peptide was purified by gel filtration as in Example 3 to yield 225 mg of semi-pure product. This material was further purified by preparative HPLC as in Example 3, except that a linear gradient of 27–37% was run, to yield 80.9 mg of a white, amorphous powder. The compound was homogeneous by HPLC and gave a correct amino acid analysis. FAB-MS: MH calc. 3295.7, found 3296.2.

EXAMPLE 32

Preparation of Ac-[1-Nal$^6$,Lys$^{12}$,Nle$^{17}$,Ala$^{19}$,Asp$^{25}$,Val$^{26}$, Thr$^{28}$]-VIP cyclo (Lys$^{21}$→Asp$^{25}$) [Ac-(SEQ ID No:50)-NH$_2$]

A 0.65 g (0.1 mmol) portion of the Boc-docosapeptide resin of Example 31 was carried through six coupling cycles as in Example 27 except that Boc-p-F-Phe in the first cycle was replaced by Boc-1-Nal (315 mg, 1.0 mmol). The peptide resin was carried through steps 1–8 of protocol 1 and treated with 0.5 mL acetic anhydride in 20 mL 6% DIPEA/methylene chloride for 60 minutes. The resin was washed using steps 10–14 and dried under vacuum to give 0.801 g.

This peptide-resin was deblocked as in Example 7 to yield 250 mg of crude peptide. The peptide was purified by gel filtration as in Example 3 to yield 188 mg of semi-pure product. This material was further purified by preparative HPLC as in Example 3, except that a linear gradient of 27–37% was run, to yield 28.0 mg of a white, amorphous powder. The compound was homogeneous by HPLC and gave a correct amino acid analysis. FAB-MS: MH calc. 3327.8, found 3328.5.

EXAMPLE 33

Preparation of Ac-[Ala$^2$,Glu$^8$,Lys$^{12}$,Nle$^{17}$,Ala$^{19}$,Asp$^{25}$, Leu$^{26}$,Lys$^{27,28}$,Gly$^{29,30}$,Thr$^{31}$]-VIP cyclo (Lys$^{21}$→Asp$^{25}$) [Ac-(SEQ ID No:51)-NH$_2$]

Benzhydrylamine resin (1.1 g, 0.5 mmol, 200–400 ASTM mesh, Biomega) was subjected to solid phase synthesis using protocol 1 as in Example 2. Thirteen coupling cycles were performed as in Example 24 except that the Boc-Ala in the first cycle was replaced by Boc-Thr(Bzl) (619 mg, 2.0 mmol), Boc-Ala in the second cycle was replaced by Boc-Gly (350 mg, 2.0 mmol), and Boc-Ala in the third cycle was replaced by Boc Gly (350 mg, 2.0 mmol) to give 2.03 g of Boc-tridecapeptide resin.

A 1.22 g (0.3 mmol) portion of this resin was subjected to solid phase synthesis on an APPLIED BIOSYSTEMS model 430A peptide synthesizer as in Example 8. Sixteen coupling cycles were performed as in Example 24 except that Boc-Asp(OcHx) in the eleventh cycle was replaced by Boc-Glu(Bzl) (675 mg, 2.0 mmol) to give 1.95 g of Boc-nonacosapeptide resin.

A 0.975 g (0.15 mmol) portion of this resin was carried through two coupling cycles as above with Boc-Ala (378 mg, 2.0 mmol) and Boc-His(Tos) (819 mg, 2.0 mmol) to give 1.05 g. This resin was then carried through steps 1–8 of protocol 1 and treated with 0.5 mL acetic anhydride in 20 mL 6% DIPEA/methylene chloride for 60 minutes. The resin was washed using steps 10–14 of protocol 1 and dried under vacuum to yield 0.897 g.

This peptide-resin was deblocked as in Example 7 to yield 270 mg of crude peptide. The peptide was purified by gel filtration as in Example 3 to yield 150 mg of semi-pure product. This material was further purified by preparative HPLC as in Example 3, except that a linear gradient of 24–34% was run, to yield 28.7 mg of a white, amorphous powder. The compound was homogeneous by HPLC and gave a correct amino acid analysis. FAB-MS: MH calc. 3547.1, found 3546.9.

EXAMPLE 34

Preparation of Ac-[Glu$^8$,Lys$^{12}$,Nle$^{17}$,Ala$^{19}$,Asp$^{25}$,Leu$^{26}$, Lys$^{27,28}$,Gly$^{29,30}$,Thr$^{31}$]-VIP cyclo (Lys$^{21}$→Asp$^{25}$) [Ac-(SEQ ID No:52)-NH$_2$]

A 0.975 g (0.15 mmol) portion of the Boc-nonacosapeptide resin of Example 33 was carried through two coupling cycles as in Example 33 except that Boc-Ala in the first cycle was replaced by Boc-Ser(Bzl) (590 mg, 2.0 mmol) to yield 0.915 g.

This peptide-resin was deblocked as in Example 7 to yield 303 mg of crude peptide. The peptide was purified by gel filtration as in Example 3 to yield 180 mg of semi-pure product. This material was further purified by preparative HPLC as in Example 3, except that a linear gradient of 25–35% was run, to yield 42.8 mg of a white, amorphous powder. The compound was homogeneous by HPLC and gave a correct amino acid analysis. FAB-MS: MH calc. 3563.1, found 3562.6.

EXAMPLE 35

Preparation of Ac-[Ala$^2$,Glu$^8$,Lys$^{12}$,Nle$^{17}$,Ala$^{19}$,Asp$^{25}$, Leu$^{26}$,Lys$^{27,28}$]-VIP cyclo (Lys$^{21}$→Asp$^{25}$) [Ac-(SEQ ID No:53)-NH$_2$]

A 0.27 g (0.1 mmol) portion of the Boc-nonapeptide resin of Example 20 was subjected to solid phase synthesis on an Applied Biosystems model 430A peptide synthesizer as in Example 8. Nineteen coupling cycles were performed of one cycle each with Boc-Ala (378 mg, 2.0 mmol), Boc-Ala (378 mg, 2.0 mmol), Boc-Nle (462 mg, 2.0 mmol), Boc-Gln (493 mg, 2.0 mmol), Boc-Lys(2-Cl-Z) (830 mg, 2.0 mmol), Boc-Arg(Tos) (856 mg, 2.0 mmol), Boc-Leu (499 mg, 2.0 mmol), Boc-Lys(2-Cl-Z) (830 mg, 2.0 mmol), Boc-Thr(Bzl) (618 mg, 2.0 mmol), Boc-Tyr(2,6-DCB) (880 mg, 2.0 mmol), Boc-Asn (464 mg, 2.0 mmol), Boc-Glu(Bzl) (675 mg, 2.0 mmol), Boc-Thr(Bzl) (618 mg, 2.0 mmol), Boc-Phe (531 mg, 2.0 mmol), Boc-Val (435 mg, 2.0 mmol), Boc-Ala (378 mg, 2.0 mmol), Boc-Asp(OcHx) (630 mg, 2.0 mmol), Boc-Ser(Bzl) (590 mg, 2.0 mmol), and Boc-His(Tos) (818 mg, 2.0 mmol) to give 0.57 g of Boc-octacosapeptide resin.

This resin was then carried through steps 1–8 of protocol 1 and treated with 0.5 mL acetic anhydride in 20 mL 6% DIPEA/methylene chloride for 60 minutes. The resin was washed using steps 10–14 of protocol 1 and dried under vacuum to yield 0.506 g.

This peptide-resin was deblocked as in Example 7 to yield 160 mg of crude peptide. The peptide was purified by gel filtration as in Example 3 to yield 100 mg of semi-pure product. This material was further purified by preparative HPLC as in Example 3, except that a linear gradient of 25–35% was run, to yield 17.1 mg of a white, amorphous powder. The compound was homogeneous by HPLC and gave a correct amino acid analysis. FAB-MS: MH calc. 3331.9, found 3332.0.

EXAMPLE 36

Preparation of Ac-[p-NH$_2$-Phe$^{10}$,Lys$^{12}$,Nle$^{17}$,Ala$^{19}$,Asp$^{25}$, Val$^{26}$,Thr$^{28}$]-VIP cyclo (Lys$^{21}$→Asp$^{25}$) [Ac-(SEQ ID No:54)-NH$_2$]

A 0.6 g (0.1 mmol) portion of the Boc-nonapeptide resin from Example 17 was subjected to solid phase synthesis on an APPLIED BIOSYSTEMS model 430A peptide synthesizer as in Example 8. Nine coupling cycles were performed as in Example 23 to give 0.72 g of Boc-octadecapeptide resin. This resin was carried through one coupling cycle with Boc-p-NH(CBZ)-Phe (166 mg, 0.4 mmol) to give 0.79 g of Boc-nonadecapeptide resin. This resin was subjected to solid phase synthesis on an APPLIED BIOSYSTEMS model 430A peptide synthesizer as in Example 8. Nine coupling cycles were performed as in Example 23 to give 0.72 g of Boc-octadecapeptide resin. This resin was subjected to solid phase synthesis on an Applied Biosystems model 430A peptide synthesizer as in Example 8. Nine coupling cycles were performed of one cycle each with Boc-Asn (464 mg, 2.0 mmol), Boc-Asp(OcHx) (630 mg, 2.0 mmol), Boc-Thr(Bzl) (618 mg, 2.0 mmol), Boc-Phe (531 mg, 2.0 mmol), Boc-Val (435 mg, 2.0 mmol), Boc-Ala (378 mg, 2.0 mmol), Boc-Asp(OcHx) (630 mg, 2.0 mmol), Boc-Ser(Bzl) (590 mg, 2.0 mmol), and Boc-His(Tos) (819 mg, 2.0 mmol) to give 0.91 g. This resin was then carried through steps 1–8 of protocol 1 and treated with 0.5 mL acetic anhydride in 20 mL 6% DIPEA/methylene chloride for 60 minutes. The resin was washed using steps 10–14 of protocol 1 and dried under vacuum to yield 0.85 g.

This peptide-resin was deblocked as in Example 7 to yield 350 mg of crude peptide. The peptide was purified by gel filtration as in Example 3 to yield 138 mg of semi-pure product. This material was further purified by preparative HPLC as in Example 3, except that a linear gradient of 25–35% was run, to yield 25.2 mg of a white, amorphous powder. The compound was homogeneous by HPLC and gave a correct amino acid analysis. FAB-MS: MH calc. 3276.8, found 3276.2.

EXAMPLE 37

Preparation of Ac-[Lys$^{12}$,Nle$^{17}$,Ala$^{19}$,m-OCH$_3$-Tyr$^{22}$, Asp$^{25}$,Val$^{26}$,Thr$^{28}$]-VIP cyclo (Lys$^{21}$→Asp$^{25}$) [Ac-(SEQ ID No:55)-NH$_2$]

Benzhydrylamine resin (0.125 g, 0.1 mmol, 100–200 ASTM mesh, Bachem) was subjected to solid phase synthesis using protocol 1 as in Example 2. Nine coupling cycles were performed of one cycle each with Boc-Thr(Bzl) (310 mg, 1.0 mmol), Boc-Leu (267 mg, 1.0 mmol), Boc-Val (217 mg, 1.0 mmol), Boc-Asp(OFm) (212 mg, 0.5 mmol), Boc-Asn (255 mg, 1.1 mmol), Boc-Leu (249 mg, 1.0 mmol), Boc-m-OCH$_3$-Tyr (Bzl) (80 mg, 0.2 mmol), Boc-Lys (Fmoc) (234 mg, 0.5 mmol) and Boc-Lys(2-Cl-Z) (415 mg, 1.0 mmol). This resin was then selectively deblocked by treating with steps 1–11 of protocol 2 and reacted with BOP (132 mg, 0.3 mmol) in 10 mL 1% DIPEA/DMF for 3.5 hours. Kaiser ninhydrin analysis was negative. The resin was washed using steps 13–16 of protocol 2.

Nineteen coupling cycles were performed of one cycle each with Boc-Ala (189 mg, 1.0 mmol), Boc-Ala (189 mg, 1.0 mmol), Boc-Nle (231 mg, 1.0 mmol), Boc-Gln (270 mg, 1.1 mmol), Boc-Lys(2-Cl-Z) (415 mg, 1.0 mmol), Boc-Arg (Tos) (428 mg, 1.0 mmol), Boc-Leu (267 mg, 1.0 mmol), Boc-Lys(2-Cl-Z) (415 mg, 1.0 mmol), Boc-Thr(Bzl) (310 mg, 1.0 mmol), Boc-Tyr(2,6-DCB) (220 mg, 0.5 mmol), Boc-Asn (256 mg, 1.0 mmol), Boc-Asp(OcHx) (315 mg, 1.0 mmol), Boc-Thr(Bzl) (310 mg, 1.0 mmol), Boc-Phe (265 mg, 1.0 mmol), Boc-Val (217 mg, 1.0 mmol), Boc-Ala (189 mg, 1.0 mmol), Boc-Asp(OcHx) (315 mg, 1.0 mmol), Boc-Ser(Bzl) (295 mg, 1.0 mmol), and Boc-His(Tos) (409 mg, 1.0 mmol).

This resin was then carried through steps 1–8 of protocol 1 and treated with 0.5 mL acetic anhydride in 10 mL 6% DIPEA/methylene chloride for 60 minutes. The resin was washed using steps 10–14 of protocol 1 and dried under vacuum to yield 0.814 g.

This peptide-resin was deblocked as in Example 7 to yield 265 mg of crude peptide. The peptide was purified by gel filtration as in Example 3 to yield 150 mg of semi-pure product. This material was further purified by preparative HPLC as in Example 3, except that a linear gradient of 23–33% was run, to yield 8.1 mg of a white, amorphous powder. The compound was homogeneous by HPLC and gave a correct amino acid analysis. FAB-MS: MH calc. 3307.8, found 3306.8.

EXAMPLE 38

Preparation of Ac-[Lys$^{12}$,Nle$^{17}$,Ala$^{19}$,m-F-L-Tyr$^{22}$,Asp$^{25}$, Val$^{26}$,Thr$^{28}$]-VIP cyclo (Lys$^{21}$→Asp$^{25}$) [Ac-(SEQ ID No:56)-NH$_2$]

Benzhydrylamine resin (0.125 g, 0.1 mmol, 100–200 ASTM mesh, Bachem) was subjected to solid phase synthesis using protocol 1 as in Example 2. Twenty-eight coupling cycles were performed as in Example 37 except that the Boc-m-OCH$_3$-Tyr(Bzl) in the seventh cycle was replaced by Boc-m-F-DL-Tyr(Bzl) (78 mg, 0.2 mmol) to give 0.754 g.

This peptide-resin was deblocked as in Example 7 to yield 254 mg of crude peptide. The peptide was purified by gel filtration as in Example 3 to yield 114 mg of semi-pure product. This material was further purified by preparative HPLC as in Example 3, except that a linear gradient of 27–37% was run, to yield 15.1 mg of a white, amorphous powder. The compound was homogeneous by HPLC and gave a correct amino acid analysis. FAB-MS: MH calc. 3295.7, found 3295.5.

EXAMPLE 39

Preparation of Ac-[Glu$^8$,Lys$^{12}$,Nle$^{17}$,Ala$^{19}$,m-OCH$_3$-Tyr$^{22}$, Asp$^{25}$,Leu$^{26}$,Lys$^{27,28}$]-VIP cyclo (Lys$^{21}$→Asp$^{25}$) [Ac-(SEQ ID No:57)-NH$_2$]

Benzhydrylamine resin (0.125 g, 0.1 mmol, 100–200 ASTM mesh, Bachem) was subjected to solid phase synthesis using protocol 1 as in Example 2. Twenty-eight coupling cycles were performed as in Example 37 except that the Boc-Thr(Bzl) in the first cycle was replaced by Boc-Lys(2-Cl-Z) (415 mg, 1.0 mmol), Boc-Leu in the second cycle was replaced by Boc-Lys(2-Cl-Z) (415 mg, 1.0 mmol), Boc-Val in the third cycle was replaced by Boc-Leu (268 mg, 1.0 mmol), and Boc-Asp(OcHx) in the twenty-first cycle was replaced by Boc-Glu(O-Bzl) (337 mg, 1.0 mmol) to give 0.90 g.

This peptide-resin was deblocked as in Example 7 to yield 270 mg of crude peptide. The peptide was purified by gel filtration as in Example 3 to yield 155 mg of semi-pure product. This material was further purified by preparative HPLC as in Example 3, except that a linear gradient of 25–35% was run, to yield 29.6 mg of a white, amorphous powder. The compound was homogeneous by HPLC and gave a correct amino acid analysis. FAB-MS: MH calc. 3377.9, found 3377.9.

EXAMPLE 40

Preparation of Ac-[Glu$^8$,Lys$^{12}$,Nle$^{17}$,Ala$^{19}$,m-F-L-Tyr$^{22}$, Asp$^{25}$,Leu$^{26}$,Lys$^{27,28}$]-VIP cyclo (Lys$^{21}$→Asp$^{25}$) [Ac-(SEQ ID No:58)-NH$_2$]

Benzhydrylamine resin (0.125 g, 0.1 mmol, 100–200 ASTM mesh, Bachem) was subjected to solid phase synthesis using protocol 1 as in Example 2. Twenty-eight coupling cycles were performed as in Example 39 except that the Boc-m-OCH$_3$-Tyr(Bzl) in the seventh cycle was replaced by Boc-m-F-DL-Tyr(Bzl) (78 mg, 0.2 mmol) to give 0.83 g.

This peptide-resin was deblocked as in Example 7 to yield 240 mg of crude peptide. The peptide was purified by gel filtration as in Example 3 to yield 100 mg of semi-pure product. This material was further purified by preparative HPLC as in Example 3, except that a linear gradient of 25–35% was run, to yield 37.2 mg of a white, amorphous powder. The compound was homogeneous by HPLC and gave a correct amino acid analysis. FAB-MS: MH calc. 3365.9, found 3365.8.

EXAMPLE 41

Preparation of Ac-[Ala$^8$,Lys$^{12}$,Nle$^{17}$,Ala$^{19}$,Ala$^{24}$,Asp$^{25}$, Leu$^{26}$,Lys$^{27,28}$]-VIP cyclo (Lys$^{21}$→Asp$^{25}$) [Ac-(SEQ ID No:59)-NH$_2$]

Benzhydrylamine resin (0.125 g, 0.1 mmol, 100–200 ASTM mesh, Bachem) was subjected to solid phase synthesis using protocol 1 as in Example 2. Twenty-eight coupling cycles were performed as in Example 39 except that the Boc-Asn in the fifth cycle was replaced by Boc-Ala (189 mg, 1.0 mmol), Boc-m-OCH$_3$-Tyr(Bzl) in the seventh cycle was replaced by Boc-Tyr(2,6-DCB) (440 mg, 1.0 mmol), and Boc-Glu(OBzl) in the twenth-first cycle was replaced by Boc-Ala (189 mg, 1.0 mmol) to give 0.85 g.

This peptide-resin was deblocked as in Example 7 to yield 255 mg of crude peptide. The peptide was purified by gel filtration as in Example 3 to yield 112 mg of semi-pure product. This material was further purified by preparative HPLC as in Example 3, except that a linear gradient of 25–35% was run, to yield 12.0 mg of a white, amorphous powder. The compound was homogeneous by HPLC and gave a correct amino acid analysis. FAB-MS: MH calc. 3246.8, found 3246.7.

EXAMPLE 42

Preparation of Ac-[Glu$^8$,Lys$^{12}$,Ala$^{16,17,19}$,Asp$^{25}$,Leu$^{26}$, Lys$^{27,28}$]-VIP cyclo (Lys$^{21}$→Asp$^{25}$) [Ac-(SEQ ID No:60)-NH$_2$]

Benzhydrylamine resin (0.125 g, 0.1 mmol, 100–200 ASTM mesh, Bachem) was subjected to solid phase synthesis using protocol 1 as in Example 2. Twenty-eight coupling cycles were performed as in Example 41 except that the Boc-Ala in the fifth cycle was replaced by Boc-Asn (256 mg, 1.1 mmol), Boc-Nle in the twelfth cycle was replaced by Boc-Ala (189 mg, 1.0 mmol), Boc-Gln in the thirteenth cycle was replaced by Boc-Ala (189 mg, 1.0 mmol), and Boc-Ala in the twenth-first cycle was replaced by Boc-Glu(OBzl) (337 mg, 1.0 mmol) to give 0.80 g.

This peptide-resin was deblocked as in Example 7 to yield 254 mg of crude peptide. The peptide was purified by gel filtration as in Example 3 to yield 115 mg of semi-pure product. This material was further purified by preparative HPLC as in Example 3, except that a linear gradient of 20–30% was run, to yield 32.1 mg of a white, amorphous powder. The compound was homogeneous by HPLC and gave a correct amino acid analysis. FAB-MS: MH calc. 3248.7, found 3248.3.

EXAMPLE 43

Preparation of Ac-[Ala$^8$,Lys$^{12}$,Ala$^{16}$,Nle$^{17}$,Ala$^{19}$,Ala$^{24}$, Asp$^{25}$,Leu$^{26}$,Lys$^{27,28}$]-VIP cyclo (Lys$^{21}$→Asp$^{25}$) [Ac-(SEQ ID No:61)-NH$_2$]

Benzhydrylamine resin (0.125 g, 0.1 mmol, 100–200 ASTM mesh, Bachem) was subjected to solid phase synthesis using protocol 1 as in Example 2. Twenty-eight coupling cycles were performed as in Example 41 except that the Boc-Gln in the thirteenth cycle was replaced by Boc-Ala (189 mg, 1.0 mmol) to give 0.93 g.

This peptide-resin was deblocked as in Example 7 to yield 250 mg of crude peptide. The peptide was purified by gel filtration as in Example 3 to yield 100 mg of semi-pure product. This material was further purified by preparative HPLC as in Example 3, except that a linear gradient of 27–37% was run, to yield 23.6 mg of a white, amorphous powder. The compound was homogeneous by HPLC and gave a correct amino acid analysis. FAB-MS: MH calc. 3189.8, found 3189.9.

EXAMPLE 44

Preparation of Ac-[Ala$^8$,Lys$^{12}$,Ala$^{16,17,19}$,Ala$^{24}$,Asp$^{25}$, Leu$^{26}$,Lys$^{27,28}$]-VIP cyclo (Lys$^{21}$→Asp$^{25}$) [Ac-(SEQ ID No:62)-NH$_2$]

Benzhydrylamine resin (0.125 g, 0.1 mmol, 100–200 ASTM mesh, Bachem) was subjected to solid phase synthesis using protocol 1 as in Example 2. Twenty-eight coupling cycles were performed as in Example 43 except that the Boc-Nle in the twelfth cycle was replaced by Boc-Ala (159 mg, 1.0 mmol) to give 0.762 g.

This peptide-resin was deblocked as in Example 7 to yield 240 mg of crude peptide. The peptide was purified by gel filtration as in Example 3 to yield 150 mg of semi-pure product. This material was further purified by preparative HPLC as in Example 3, except that a linear gradient of 22–32% was run, to yield 55.3 mg of a white, amorphous powder. The compound was homogeneous by HPLC and gave a correct amino acid analysis. FAB-MS: MH calc. 3147.7, found 3148.0.

EXAMPLE 45

Preparation of Ac-[Glu$^8$,Lys$^{12}$,Ala$^{16}$,Nle$^{17}$,Ala$^{19}$,Asp$^{25}$, Leu$^{26}$,Lys$^{27,28}$]-VIP cyclo (Lys$^{21}$→Asp$^{25}$) [Ac-(SEQ ID No:63)-NH$_2$]

Benzhydrylamine resin (0.125 g, 0.1 mmol, 100–200 ASTM mesh, Bachem) was subjected to solid phase synthesis using protocol 1 as in Example 2. Twenty-eight coupling cycles were performed as in Example 42 except that the Boc-Ala in the twelfth cycle was replaced by Boc-Nle (231 mg, 1.0 mmol) to give 0.775 g. This peptide-resin was deblocked as in Example 7 to yield 203 mg of crude peptide. The peptide was purified by gel filtration as in Example 3 to yield 100 mg of semi-pure product. This material was further purified by preparative HPLC as in Example 3, except that a linear gradient of 27–37% was run, to yield 40.0 mg of a white, amorphous powder. The compound was homogeneous by HPLC and gave a correct amino acid analysis. FAB-MS: MH calc. 3290.8, found 3290.5.

EXAMPLE 46

Preparation of Ac-[Glu$^8$,Lys$^{12}$,Ala$^{16,17,19}$,Ala$^{24}$,Asp$^{25}$, Leu$^{26}$,Lys$^{27,28}$]-VIP cyclo (Lys$^{21}$→Asp$^{25}$) [Ac-(SEQ ID No:64)-NH$_2$]

Benzhydrylamine resin (0.125 g, 0.1 mmol, 100–200 ASTM mesh, Bachem) was subjected to solid phase synthesis using protocol 1 as in Example 2. Twenty-eight coupling cycles were performed as in Example 43 except that the Boc-Ala in the twenty-first cycle was replaced by Boc-Glu(OBzl) (337 mg, 1.0 mmol) to give 0.837 g.

This peptide-resin was deblocked as in Example 7 to yield 178 mg of crude peptide. The peptide was purified by gel filtration as in Example 3 to yield 126 mg of semi-pure product. This material was further purified by preparative HPLC as in Example 3, except that a linear gradient of 20–30% was run, to yield 24.9 mg of a white, amorphous powder. The compound was homogeneous by HPLC and gave a correct amino acid analysis. FAB-MS: MH calc. 3205.7, found 3205.2.

EXAMPLE 47

Preparation of Ac-[Glu$^8$,Lys$^{12}$,Nle$^{17}$,Ala$^{19}$,Asp$^{25}$,Val$^{26}$, Thr$^{28}$,Gly$^{29,30}$,Thr$^{31}$]-VIP cyclo (Lys$^{21}$→Asp$^{25}$) [Ac-(SEQ ID No: 65)-NH$_2$]

Benzhydrylamine resin (0.125 g, 0.1 mmol, 100–200 ASTM mesh, Bachem) was subjected to solid phase synthesis using protocol 1 as in Example 2. Three coupling cycles were performed of one cycle each with Boc-Thr(Bzl) (310 mg, 1.0 mmol), Boc-Gly (175 mg, 1.0 mmol), and Boc-Gly (175 mg, 1.0 mmol). Twenty-eight coupling cycles were performed as in Example 37 except that the Boc-m-OCH$_3$-Tyr(Bzl) in the seventh cycle was replaced by Boc-Tyr(2,6-DCB) (440 mg, 1.0 mmol), and Boc-Asp(OcHx) in the twenty-first cycle was replaced by Boc-Glu(O-Bzl) (337 mg, 1.0 mmol) to give 0.895 g.

This peptide-resin was deblocked as in Example 7 to yield 440 mg of crude peptide. The peptide was purified by gel filtration as in Example 3 to yield 120 mg of semi-pure product. This material was further purified by preparative HPLC as in Example 3, except that a linear gradient of 25–35% was run, to yield 27.7 mg of a white, amorphous powder. The compound was homogeneous by HPLC and gave a correct amino acid analysis. FAB-MS: MH calc. 3506.9, found 3205.8.

EXAMPLE 48

Preparation of Ac-[p-F-Phe$^6$,Glu$^8$,Lys$^{12}$,Nle$^{17}$,Asp$^{25}$,Val$^{26}$, Thr$^{28}$,Gly$^{29,30}$,Thr$^{31}$]-VIP cyclo (Lys$^{21}$→Asp$^{25}$) [Ac-(SEQ ID No:66)-NH$_2$]

Benzhydrylamine resin (0.125 g, 0.1 mmol, 100–200 ASTM mesh, Bachem) was subjected to solid phase synthesis using protocol 1 as in Example 2. Thirty-one coupling cycles were performed as in Example 47 except that the Boc-Ala in the thirteenth cycle was replaced by Boc-Val (217 mg, 1.0 mmol), and Boc-Phe in the twenty-sixth cycle was replaced by Boc-p-F-Phe (142 mg, 0.5 mmol) to give 0.754 g.

This peptide-resin was deblocked as in Example 7 to yield 280 mg of crude peptide. The peptide was purified by gel filtration as in Example 3 to yield 152 mg of semi-pure product. This material was further purified by preparative HPLC as in Example 3, except that a linear gradient of 27–38% was run, to yield 53.4 mg of a white, amorphous powder. The compound was homogeneous by HPLC and gave a correct amino acid analysis. FAB-MS: MH calc. 3553.0, found 3552.2.

EXAMPLE 49

Preparation of Ac-[Ala$^2$,Glu$^8$,Lys$^{12}$,Nle$^{17}$,Asp$^{25}$,Leu$^{26}$, Lys$^{27,28}$,Gly$^{29,30}$,Thr$^{31}$]-VIP cyclo (Lys$^{21}$→Asp$^{25}$) [Ac-(SEQ ID No:67)-NH$_2$]

Benzhydrylamine resin (0.125 g, 0.1 mmol, 100–200 ASTM mesh, Bachem) was subjected to solid phase synthesis using protocol 1 as in Example 2. Thirty-one coupling cycles were performed as in Example 47 except that the Boc-Thr(Bzl) in the fourth cycle was replaced by Boc-Lys (2-Cl-Z) (414 mg, 1.0 mmol), Boc-Leu in the fifth cycle was replaced by Boc-Lys(2-Cl-Z) (414 mg, 1.0 mmol), Boc-Val in the sixth cycle was replaced by Boc-Leu (249 mg, 1.0 mmol), Boc-Ala in the thirteenth cycle was replaced by Boc-Val (217 mg, 1.0 mmol), and Boc-Ser(Bzl) in the thirtieth cycle was replaced by Boc-Ala (189 mg, 1.0 mmol) to give 0.838 g.

This peptide-resin was deblocked as in Example 7 to yield 370 mg of crude peptide. The peptide was purified by gel filtration as in Example 3 to yield 196 mg of semi-pure product. This material was further purified by preparative HPLC as in Example 3, except that a linear gradient of 23–33% was run, to yield 48.4 mg of a white, amorphous powder. The compound was homogeneous by HPLC and gave a correct amino acid analysis. FAB-MS: MH calc. 3575.1, found 3574.0.

EXAMPLE 50

Preparation of Ac-[Glu$^8$,Lys$^{12}$,Nle$^{17}$,Asp$^{25}$,Leu$^{26}$,Lys$^{27,28}$, Gly$^{29,30}$,Thr$^{31}$]-VIP cyclo (Lys$^{21}$→Asp$^{25}$) [Ac-(SEQ ID No:68)-NH$_2$]

Benzhydrylamine resin (0.125 g, 0.1 mmol, 100–200 ASTM mesh, Bachem) was subjected to solid phase synthesis using protocol 1 as in Example 2. Thirty-one coupling cycles were performed as in Example 49 except that the Boc-Ala in the thirtieth cycle was replaced by Boc-Ser(Bzl) (295 mg, 1.0 mmol) to give 0.913 g.

This peptide-resin was deblocked as in Example 7 to yield 378 mg of crude peptide. The peptide was purified by gel filtration as in Example 3 to yield 240 mg of semi-pure product. This material was further purified by preparative HPLC as in Example 3, except that a linear gradient of 25–35% was run, to yield 28.8 mg of a white, amorphous powder. The compound was homogeneous by HPLC and gave a correct amino acid analysis. FAB-MS: MH calc. 3591.1, found 3590.3.

EXAMPLE 51

Preparation of Ac-[Lys$^{12}$,Nle$^{17}$ Ala$^{19}$ Asp$^{25}$ Leu$^{26}$ Lys$^{27,28}$, Ala$^{29,31}$]-VIP cyclo (Lys$^{21}$→Asp$^{25}$) [Ac-(SEQ ID No:69)-NH$_2$]

Benzhydrylamine resin (0.125 g, 0.1 mmol, 100–200 ASTM mesh, Bachem) was subjected to solid phase synthesis using protocol 1 as in Example 2. Thirty-one coupling cycles were performed as in Example 47 except that the Boc-Thr(Bzl) in the first cycle was replaced by Boc-Ala (189 mg, 1.0 mmol), Boc-Gly in the second cycle was replaced by Boc-Ala (189 mg, 1.0 mmol), Boc-Gly in the third cycle was replaced by Boc-Ala (189 mg, 1.0 mmol), Boc-Thr(Bzl) in the fourth cycle was replaced by Boc-Lys (2-Cl-Z) (414 mg, 1.0 mmol), Boc-Leu in the fifth cycle was replaced by Boc-Lys(2-Cl-Z) (414 mg, 1.0 mmol), Boc-Val in the sixth cycle was replaced by Boc-Leu (249 mg, 1.0 mmol), and Boc-Glu(OBzl) in the twenty-fourth cycle was replaced by Boc-Asp(OcHx) (315 mg, 1.0 mmol) to give 0.844 g.

This peptide-resin was deblocked as in Example 7 to yield 360 mg of crude peptide. The peptide was purified by gel filtration as in Example 3 to yield 115 mg of semi-pure product. This material was further purified by preparative HPLC as in Example 3, except that a linear gradient of 24–34% was run, to yield 34.7 mg of a white, amorphous powder. The compound was homogeneous by HPLC and gave a correct amino acid analysis. FAB-MS: MH calc. 3547.1, found 3546.0.

EXAMPLE 52

Tracheal Relaxant Activity of VIP Analogs

The relaxant activity of the VIP analogs were studied in a model utilizing guinea pig trachea. [Wasserman, M. A. et al., in Vasoactive Intestinal Peptide, S. I. Said, ed., Raven Press, New York 1982, pp 177–184] All tissues were taken from male albino guinea pig weighing 400–600 g, anesthetized with urethane (2 g/kg, i.p.). After exanguination, the trachea were removed and divided into four ring segments (3 mm length). Each ring was suspended by 30 gauge stainless steel wires in a 10 mL jacketed tissue bath and attached via 4–0 silk thread to a GRASS force displacement transducer (model FT03C, Grass Instruments Co., Quincy, Mass.), for isometric recording of tension. The smooth muscle was bathed in modified Krebs solution of the following composition: NaCl, 120 mM; KCl, 4.7 mM; CaCl$_2$, 2.5 mM; MgSO$_4$.7H$_2$O, 1.2 mM; NaHCO$_3$, 25 mM; K$_2$HPO$_4$ monobasic, 1.2 mM; and dextrose, 10 mM. Tissue baths were maintained at 37° C. and constantly bubbled with 95% O$_2$ and 5% CO$_2$. Responses were recorded on an 8 channel and a 4 channel HEWLETT-PACKARD (model 7702B and 7754A, respectively) recorder (Hewlett- Packard, Paramus, N.J.). Tracheal rings were placed under a resting tension of 1.5 g which was determined to be at or near optimal in preliminary experiments. Frequent readjustments of tension were required during the 60 minute stabilization period which followed. Tissues were rinsed at 15 minute intervals.

Cumulative concentration response curves were obtained for each tissue by successive μL increases in the bath concentration of VIP or VIP analogs according to the method of VanRossum [Arch. Int. Pharmacodyn., 143, 299–330 (1963)]. Only one cumulative dose response curve was obtained on a single tissue. To minimize variability between tissues, relaxant responses were expressed as a percentage of the maximum response obtained to VIP (10$^-$6M=100%) added at the end of each concentration response experiment. Responses obtained from three tissues were pooled and EC$_{50}$ values were determined by linear regression.

The results summarized in Table I show the tracheal relaxant activity of the VIP analogs in comparison to native VIP.

TABLE I

Relaxant activity of VIP analogs on guinea pig tracheal smooth muscle

| Compound | $EC_{50}$ (nM) |
|---|---|
| VIP [(Seq ID NO:1)—$NH_2$] | 10 |
| Ac—[$Lys^{12}$,$Nle^{17}$,$Val^{26}$,$Thr^{28}$]-VIP cyclo ($Asp^8 \to Lys^{12}$) [Ac—(SEQ ID NO:20)—$NH_2$] | 14 |
| Ac—[$Glu^8$,$Lys^{12}$,$Nle^{17}$,$Val^{26}$,$Thr^{28}$]-VIP cyclo ($Glu^8 \to Lys^{12}$) [Ac—(SEQ ID NO:21)—$NH_2$] | 34 |
| Ac—[$Asn^8$,$Asp^9$,$Lys^{12}$,$Nle^{17}$,$Val^{26}$,$Thr^{28}$]-VIP cyclo ($Asp^9 \to Lys^{12}$) [Ac—(SEQ ID NO:22)—$NH_2$] | 17 |
| Ac—[$Orn^{12}$,$Nle^{17}$,$Val^{26}$,$Thr^{28}$]-VIP cyclo ($Asp^8 \to Orn^{12}$) [Ac—(SEQ ID NO:23)—$NH_2$] | 40 |
| Ac—[$Lys^8$,$Asp^{12}$,$Nle^{17}$,$Val^{26}$,$Thr^{28}$]-VIP cyclo ($Lys^8 \to Asp^{12}$) [Ac—(SEQ ID NO:24)—$NH_2$] | 38 |
| Ac—[$Glu^8$,$Orn^{12}$,$Nle^{17}$,$Val^{26}$,$Thr^{28}$]-VIP cyclo ($Glu^8 \to Orn^{12}$) [Ac—(SEQ ID NO:25)—$NH_2$] | 16 |
| Ac—[$Lys^{12}$,$Glu^{16}$,$Nle^{17}$,$Val^{26}$,$Thr^{28}$]-VIP cyclo ($Lys^{12} \to Glu^{16}$) [Ac—(SEQ ID NO:26)—$NH_2$] | 37 |
| Ac—[$Lys^{12}$,$Nle^{17}$,$Asp^{24}$,$Val^{26}$,$Thr^{28}$]-VIP cyclo ($Lys^{20} \to Asp^{24}$) [Ac—(SEQ ID NO:27)—$NH_2$] | 5.3 |
| Ac—[$Lys^{12}$,$Nle^{17}$,$Asp^{25}$,$Val^{26}$,$Thr^{28}$]-VIP cyclo ($Lys^{21} \to Asp^{25}$) [Ac—(SEQ ID NO:28)—$NH_2$] | 3.1 |
| Ac—[$Lys^{12}$,$Nle^{17}$,$Ala^{19}$,$Asp^{25}$,$Val^{26}$,$Thr^{28}$]-VIP cyclo ($Lys^{21} \to Asp^{25}$) [Ac—(SEQ ID NO:29)—$NH_2$] | 0.70 |
| Ac—[p-F-$Phe^6$,2-$Nal^{10}$,$Lys^{12}$,$Nle^{17}$,$Asp^{25}$,$Val^{26}$,$Thr^{28}$,$Gly^{29,30}$,$Met^{31}$]-VIP cyclo ($Lys^{21} \to Asp^{25}$) [Ac—(SEQ ID NO:30)—$NH_2$] | 1.3 |
| Ac—[$Glu^8$,$Orn^{12}$,$Nle^{17}$,$Asp^{25}$,$Val^{26}$,$Thr^{28}$]-VIP cyclo ($Lys^{21} \to Asp^{25}$) [Ac—(SEQ ID NO:31)—$NH_2$] | 2.2 |
| Ac—[p-F-$Phe^6$,$Lys^{12}$,$Nle^{17}$,$Ala^{19}$,$Asp^{25}$,$Val^{26}$,$Thr^{28}$,$Gly^{29,30}$,Cys(Acm)$^{31}$]-VIP cyclo ($Lys^{21} \to Asp^{25}$) [Ac—(SEQ ID NO:32)—$NH_2$] | 0.44 |
| Ac—[$Ala^2$,$Lys^{12}$,$Nle^{17}$,$Ala^{19}$,$Asp^{25}$,$Val^{26}$,$Thr^{28}$]-VIP cyclo ($Lys^{21} \to Asp^{25}$) [Ac—(SEQ ID NO:33)—$NH_2$] | 1.2 |
| Ac—[N—Me—$Ala^1$,$Lys^{12}$,$Nle^{17}$,$Ala^{19}$,$Asp^{25}$,$Val^{26}$,$Thr^{28}$]-VIP cyclo ($Lys^{21} \to Asp^{25}$) [Ac—(SEQ ID NO:34)—$NH_2$] | 0.71 |
| Ac—[2-$Nal^{10}$,$Leu^{12}$,$Nle^{17}$,$Ala^{19}$,$Asp^{25}$,$Val^{26}$,$Thr^{28}$]-VIP cyclo ($Lys^{21} \to Asp^{25}$) [Ac—(SEQ ID NO:35)—$NH_2$] | 4.2 |
| Ac—[O—$CH_3$—$Tyr^{10}$,$Leu^{12}$,$Nle^{17}$,$Ala^{19}$,$Asp^{25}$,$Val^{26}$,$Thr^{28}$]-VIP cyclo ($Lys^{21} \to Asp^{25}$) [Ac—(SEQ ID NO:36)—$NH_2$] | 0.84 |
| Ac—[p-F-$Phe^6$,p-$NH_2$—$Phe^{10}$,$Leu^{12}$,$Nle^{17}$,$Ala^{19}$,$Asp^{25}$,$Val^{26}$,$Thr^{28}$]-VIP cyclo ($Lys^{21} \to Asp^{25}$) [Ac—(SEQ ID NO:37)—$NH_2$] | 4.4 |
| Ac—[$Lys^{12}$,$Nle^{17}$,$Ala^{19}$,$Asp^{25}$,$Leu^{26}$,$Lys^{27,28}$]-VIP cyclo ($Lys^{21} \to Asp^{25}$) [Ac—(SEQ ID NO:38)—$NH_2$] | 0.13 |
| Ac—[N—Me—$Ala^1$,$Lys^{12}$,$Nle^{17}$,$Ala^{19}$,$Asp^{25}$,$Leu^{26}$,$Lys^{27,28}$]-VIP cyclo ($Lys^{21} \to Asp^{25}$) [Ac—(SEQ ID NO:39)—$NH_2$] | 0.95 |
| Ac—[$Glu^8$,$Lys^{12}$,$Nle^{17}$,$Ala^{19}$,$Asp^{25}$,$Leu^{26}$,$Lys^{27,28}$]-VIP cyclo ($Lys^{21} \to Asp^{25}$) [Ac—(SEQ ID NO:40)—$NH_2$] | 0.45 |
| Ac—[O—Me—$Tyr^{10}$,$Lys^{12}$,$Nle^{17}$,$Ala^{19}$,$Asp^{25}$,$Val^{26}$,$Thr^{28}$]-VIP cyclo ($Lys^{21} \to Asp^{25}$) [Ac—(SEQ ID NO:41)—$NH_2$] | 2.6 |
| Ac—[$Glu^8$,$Lys^{12}$,$Nle^{17}$,$Ala^{19}$,$Asp^{25}$,$Leu^{26}$,$Lys^{27,28}$,$Ala^{29-31}$]-VIP cyclo ($Lys^{21} \to Asp^{25}$) [Ac—(SEQ ID NO:42)—$NH_2$] | 0.61 |
| Ac—[$Ala^2$,$Glu^8$,$Lys^{12}$,$Nle^{17}$,$Ala^{19}$,$Asp^{25}$,$Leu^{26}$,$Lys^{27,28}$,$Ala^{29-31}$]-VIP cyclo ($Lys^{21} \to Asp^{25}$) [Ac—(SEQ ID NO:43)—$NH_2$] | 0.55 |
| Ac—[N—Me—$Ala^1$,$Glu^8$,$Lys^{12}$,$Nle^{17}$,$Ala^{19}$,$Asp^{25}$,$Leu^{26}$,$Lys^{27,28}$]-VIP cyclo ($Lys^{21} \to Asp^{25}$) [Ac—(SEQ ID NO:44)—$NH_2$] | 0.36 |
| Ac—[p-F-$Phe^6$,$Glu^8$,$Lys^{12}$,$Nle^{17}$,$Ala^{19}$,$Asp^{25}$,$Leu^{26}$,$Lys^{27,28}$]-VIP cyclo ($Lys^{21} \to Asp^{25}$) [Ac—(SEQ ID NO:45)—$NH_2$] | 0.47 |
| Ac—[1-$Nal^6$,$Glu^8$,$Lys^{12}$,$Nle^{17}$,$Ala^{19}$,$Asp^{25}$,$Leu^{26}$,$Lys^{27,28}$]-VIP cyclo ($Lys^{21} \to Asp^{25}$) [Ac—(SEQ ID NO:46)—$NH_2$] | 0.26 |
| Ac—[$Glu^8$,p-$NH_2$-$Phe^{10}$,$Lys^{12}$,$Nle^{17}$,$Ala^{19}$,$Asp^{25}$,$Leu^{26}$,$Lys^{27,28}$]-VIP cyclo ($Lys^{21} \to Asp^{25}$) [Ac—(SEQ ID NO:47)—$NH_2$] | 0.32 |
| Ac—[$Glu^8$,O—$CH_3$—$Tyr^{10}$,$Lys^{12}$,$Nle^{17}$,$Ala^{19}$,$Asp^{25}$,$Leu^{26}$,$Lys^{27,28}$]-VIP cyclo ($Lys^{21} \to Asp^{25}$) [Ac—(SEQ ID NO:48)—$NH_2$] | 0.41 |
| Ac—[p-F-$Phe^6$,$Lys^{12}$,$Nle^{17}$,$Ala^{19}$,$Asp^{25}$,$Val^{26}$,$Thr^{28}$]-VIP cyclo ($Lys^{21} \to Asp^{25}$) [Ac—(SEQ ID NO:49)—$NH_2$] | 0.39 |
| Ac—[1-$Nal^6$,$Lys^{12}$,$Nle^{17}$,$Ala^{19}$,$Asp^{25}$,$Val^{26}$,$Thr^{28}$]-VIP cyclo ($Lys^{21} \to Asp^{25}$) [Ac—(SEQ ID NO:50)—$NH_2$] | 2.9 |
| Ac—[$Ala^2$,$Glu^8$,$Lys^{12}$,$Nle^{17}$,$Ala^{19}$,$Asp^{25}$,$Leu^{26}$,$Lys^{27,28}$,$Gly^{29,30}$,$Thr^{31}$]-VIP cyclo ($Lys^{21} \to Asp^{25}$) [Ac—(SEQ ID NO:51)—$NH_2$ | 0.92 |

TABLE I-continued

Relaxant activity of VIP analogs on guinea pig tracheal smooth muscle

| Compound | EC$_{50}$ (nM) |
|---|---|
| Ac—[Glu$^8$,Lys$^{12}$,Nle$^{17}$,Ala$^{19}$,Asp$^{25}$,Leu$^{26}$,Lys$^{27,28}$,Gly$^{29,30}$,Thr$^{31}$]-VIP cyclo Lys$^{21}$→Asp$^{25}$) [Ac—(SEQ ID NO:52)—NH$_2$) | 0.35 |
| Ac—[Ala$^2$,Glu$^8$,Lys$^{12}$,Nle$^{17}$,Ala$^{19}$,Asp$^{25}$,Leu$^{26}$,Lys$^{27,28}$]-VIP cyclo (Lys$^{21}$→Asp$^{25}$) [Ac—(SEQ ID NO:53)—NH$_2$] | 0.78 |
| Ac—[p-NH$_2$-Phe$^{10}$,Lys$^{12}$,Nle$^{17}$,Ala$^{19}$,Asp$^{25}$,Val$^{26}$,Thr$^{28}$]-VIP cyclo (Lys$^{21}$→Asp$^{25}$) [Ac—(SEQ ID NO:54)—NH$_2$] | 0.96 |
| Ac—[Lys$^{12}$,Nle$^{17}$,Ala$^{19}$,m-OCH$_3$—Tyr$^{22}$,Asp$^{25}$,Val$^{26}$,Thr$^{28}$]-VIP cyclo (Lys$^{21}$→Asp$^{25}$) [Ac—(SEQ ID NO:55)—NH$_2$] | 0.31 |
| Ac—[Lys$^{12}$,Nle$^{17}$,Ala$^{19}$,m-F-L-Tyr$^{22}$,Asp$^{25}$,Val$^{26}$,Thr$^{28}$]-VIP cyclo (Lys$^{21}$→Asp$^{25}$) [Ac—(SEQ ID NO:56)—NH$_2$] | 0.52 |
| Ac—[Glu$^8$,Lys$^{12}$,Nle$^{17}$,Ala$^{19}$,m-OCH$_3$—Tyr$^{22}$,Asp$^{25}$,Leu$^{26}$,Lys$^{27,28}$]-VIP cyclo (Lys$^{21}$→Asp$^{25}$) [Ac—(SEQ ID NO:57)—NH$_2$] | 0.29 |
| Ac—[Glu$^8$,Lys$^{12}$,Nle$^{17}$,Ala$^{19}$,m-F-L-Tyr$^{22}$,Asp$^{25}$,Leu$^{26}$,Lys$^{27,28}$]-VIP cyclo (Lys$^{21}$→Asp$^{25}$) [Ac—(SEQ ID NO:58)—NH$_2$] | 0.31 |
| Ac—[Ala$^8$,Lys$^{12}$,Nle$^{17}$,Ala$^{19}$,Ala$^{24}$,Asp$^{25}$,Leu$^{26}$,Lys$^{27,28}$]-VIP cyclo (Lys$^{21}$→Asp$^{25}$) [Ac—(SEQ ID NO:59)—NH$_2$] | 1.1 |
| Ac—[Glu$^8$,Lys$^{12}$,Ala$^{16,17,19}$,Asp$^{25}$,Leu$^{26}$,Lys$^{27,28}$]-VIP cyclo (Lys$^{21}$→Asp$^{25}$) [Ac—(SEQ ID NO:60)—NH$_2$] | 0.26 |
| Ac—[Ala$^8$,Lys$^{12}$,Ala$^{16}$,Nle$^{17}$,Ala$^{19}$,Ala$^{24}$,Asp$^{25}$,Leu$^{26}$,Lys$^{27,28}$]-VIP cyclo (Lys$^{21}$→Asp$^{25}$) [Ac—(SEQ ID NO:61)—NH$_2$] | 2.4 |
| Ac—[Ala$^8$,Lys$^{12}$,Ala$^{16,17,19}$,Ala$^{24}$,Asp$^{25}$,Leu$^{26}$,Lys$^{27,28}$]-VIP cyclo (Lys$^{21}$→Asp$^{25}$) [Ac—(SEQ ID NO:62)—NH$_2$] | 0.1 |
| Ac—[Glu$^8$,Lys$^{12}$,Ala$^{16}$,Nle$^{17}$,Ala$^{19}$,Asp$^{25}$,Leu$^{26}$,Lys$^{27,28}$]-VIP cyclo (Lys$^{21}$→Asp$^{25}$) [Ac—(SEQ ID NO:63)—NH$_2$ | 0.9 |
| Ac—[Glu$^8$,Lys$^{12}$,Ala$^{16,17,19}$,Ala$^{24}$,Asp$^{25}$,Leu$^{26}$,Lys$^{27,28}$]-VIP cyclo (Lys$^{21}$→Asp$^{25}$) [Ac—(SEQ ID NO:64)—NH$_2$ | 0.22 |
| Ac—[Glu$^8$,Lys$^{12}$,Nle$^{17}$,Ala$^{19}$,Asp$^{25}$,Val$^{26}$,Thr$^{28}$,Gly$^{29,30}$,Thr$^{31}$]-VIP cyclo (Lys$^{21}$→Asp$^{25}$) [Ac—(SEQ ID NO:65)—NH$_2$ | 0.88 |
| Ac—[p-F-Phe$^6$,Glu$^8$,Lys$^{12}$,Nle$^{17}$,Asp$^{25}$,Val$^{26}$,Thr$^{28}$,Gly$^{29,30}$,Thr$^{31}$]-VIP cyclo (Lys$^{21}$→Asp$^{25}$) [Ac—(SEQ ID NO:66)—NH$_2$ | 0.57 |
| Ac—[Ala$^2$,Glu$^8$,Lys$^{12}$,Nle$^{17}$,Asp$^{25}$,Leu$^{26}$,Lys$^{27,28}$,Gly$^{29,30}$,Thr$^{31}$]-VIP cyclo Lys$^{21}$→Asp$^{25}$) [Ac—(SEQ ID NO:67)—NH$_2$] | 0.19 |
| Ac—[Glu$^8$,Lys$^{12}$,Nle$^{17}$,Asp$^{25}$,Leu$^{26}$,Lys$^{27,28}$,Gly$^{29,30}$,Thr$^{31}$]-VIP cyclo (Lys$^{21}$→Asp$^{25}$) [Ac—(SEQ ID NO:68)—NH$_2$] | 0.43 |
| Ac—[Lys$^{12}$,Nle$^{17}$,Ala$^{19}$,Asp$^{25}$,Leu$^{26}$,Lys$^{27,28}$,Ala$^{29-31}$]-VIP cyclo (Lys→Asp$^{25}$) [Ac—(SEQ ID NO:69)—NH$_2$] | 0.42 |

EXAMPLE 53

Bronchodilator Activity of VIP Analogs

The in vivo bronchodilator activity of VIP and VIP analogs in guinea pigs was assessed by the tracheal instillation route of administration. This technique utilized male guinea pigs (Hartley strain, Charles River) weighing 400–600 g. Animals were anesthetized with urethane (2 g/kg) intraperitoneally and a polyethylene cannula was inserted into the jugular vein for intraveneous drug administration.

The animals were tracheotomized and dosing solutions of distilled water or test compound dissolved in distilled water were administered into the trachea, approximately three-quarters the distance to the carina with a pipette. The concentration of the dosing solution was adjusted to deliver a constant volume of 100 mL. The animals were placed supine for one minute to aid drug delivery to the lung. One minute later, spontaneous breathing was arrested with succinylcholine chloride (1.2 mg/kg) administered intraveneously, and the animals were ventilated with a HARVARD Model 680 small animal respirator set at 40 breaths/min and 4.0 cm$^3$ stroke volume. The animals were challenged with a maximal constrictory dose of histamine (50 mg/kg, i.v.) and tracheal pressure (cm of water) was recorded from a STATHAM pressure transducer (P 32 AA).

The change in tracheal pressure was averaged for at least 3 control and 3 drug-treated animals and percent inhibition was calculated. The relative potency of compounds administered by the instillation route was determined by administering various doses of test compound and calculating the median effective dose (ED$_{50}$ value). The ED$_{50}$ was determined from log dose-response curves generated by at least 3 doses that caused inhibitory effects between 10% and 90%. The correlation coefficients for the regression line of each compound was always greater than 0.95.

For determination of the time course of inhibition for various compounds, the time between administration of compound and challenge with histamine was varied. The time course of activity was calculated as the time when inhibition decreased to 40%.

The results summarized in Table II show the in vivo bronchodilator activity of the VIP analogs in comparison to native VIP.

TABLE II

Bronchodilator activity of VIP analogs in guinea pigs

| Compound | $ED_{50}$ (µg) |
|---|---|
| VIP [SEQ ID NO:1)—$NH_2$] | 7.3 |
| Ac—[$Lys^{12}$,$Glu^{16}$,$Nle^{17}$,$Val^{26}$,$Thr^{28}$]-VIP cyclo ($Lys^{12} \rightarrow Glu^{16}$) [Ac—SEQ ID NO:26)—$NH_2$] | 39 |
| Ac—[$Lys^{12}$,$Nle^{17}$,$Asp^{24}$,$Val^{26}$,$Thr^{28}$]-VIP cyclo ($Lys^{20} \rightarrow Asp^{24}$) [Ac—SEQ ID NO:27)—$NH_2$] | 2.3 |
| Ac—[$Lys^{12}$,$Nle^{17}$,$Asp^{25}$,$Val^{26}$,$Thr^{28}$]-VIP cyclo ($Lys^{21} \rightarrow Asp^{25}$) [Ac—SEQ ID NO:28)—$NH_2$] | 1.2 |
| Ac—[$Lys^{12}$,$Nle^{17}$,$Ala^{19}$,$Asp^{25}$,$Val^{26}$,$Thr^{28}$]-VIP cyclo ($Lys^{21} \rightarrow Asp^{25}$) [Ac—SEQ ID NO:29)—$NH_2$] | 0.34 |
| Ac—[p-F-$Phe^6$,2-$Nal^{10}$,$Lys^{12}$,$Nle^{17}$,$Asp^{25}$,$Val^{26}$,$Thr^{28}$,$Gly^{29,30}$,$Met^{31}$]-VIP cyclo ($Lys^{21} \rightarrow Asp^{25}$) [Ac—SEQ ID NO:30)—$NH_2$] | 0.90 |
| Ac—[$Glu^8$,$Orn^{12}$,$Nle^{17}$,$Asp^{25}$,$Val^{26}$,$Thr^{28}$]-VIP cyclo ($Lys^{21} \rightarrow Asp^{25}$) [Ac—SEQ ID NO:31)—$NH_2$] | 0.19 |
| Ac—[p-F-$Phe^6$,$Lys^{12}$,$Nle^{17}$,$Ala^{19}$,$Asp^{25}$,$Val^{26}$,$Thr^{28}$,$Gly^{29,30}$,$Cys(Acm)^{31}$]-VIP cyclo ($Lys^{21} \rightarrow Asp^{25}$) [Ac—SEQ ID NO:32)—$NH_2$] | 0.19 |
| Ac—[$Ala^2$,$Lys^{12}$,$Nle^{17}$,$Ala^{19}$,$Asp^{25}$,$Val^{26}$,$Thr^{28}$]-VIP cyclo ($Lys^{21} \rightarrow Asp^{25}$) [Ac—SEQ ID NO:33)—$NH_2$] | 0.6 |
| Ac—[N—Me—$Ala^1$,$Lys^{12}$,$Nle^{17}$,$Ala^{19}$,$Asp^{25}$,$Val^{26}$,$Thr^{28}$]-VIP cyclo ($Lys^{21} \rightarrow Asp^{25}$) [Ac—SEQ ID NO:34)—$NH_2$] | 1.0 |
| Ac—[$Lys^{12}$,$Nle^{17}$,$Ala^{19}$,$Asp^{25}$,$Leu^{26}$,$Lys^{27,28}$]-VIP cyclo ($Lys^{21} \rightarrow Asp^{25}$) [Ac—SEQ ID NO:38)—$NH_2$] | 0.09 |
| Ac—[N—Me—$Ala^1$,$Lys^{12}$,$Nle^{17}$,$Ala^{19}$,$Asp^{25}$,$Leu^{26}$,$Lys^{27,28}$]-VIP cyclo ($Lys^{21} \rightarrow Asp^{25}$) [Ac—SEQ ID NO:39)—$NH_2$] | 0.06 |
| Ac—[$Glu^8$,$Lys^{12}$,$Nle^{17}$,$Ala^{19}$,$Asp^{25}$,$Leu^{26}$,$Lys^{27,28}$]-VIP cyclo ($Lys^{21} \rightarrow Asp^{25}$) [Ac—SEQ ID NO:40)—$NH_2$] | 0.022 |
| Ac—[$Glu^8$,$Lys^{12}$,$Nle^{17}$,$Ala^{19}$,$Asp^{25}$,$Leu^{26}$,$Lys^{27,28}$$Ala^{29-31}$]-VIP cyclo ($Lys^{21} \rightarrow Asp^{25}$) [Ac—SEQ ID NO:42)—$NH_2$] | 0.072 |
| Ac—[$Ala^2$,$Glu^8$,$Lys^{12}$,$Nle^{17}$,$Ala^{19}$,$Asp^{25}$,$Leu^{26}$,$Lys^{27,28}$$Ala^{29-31}$]VIP cyclo ($Lys^{21} \rightarrow Asp^{25}$) [Ac—SEQ ID NO:43)—$NH_2$] | 0.14 |
| Ac—[N—Me—$Ala^1$,$Glu^8$,$Lys^{12}$,$Nle^{17}$,$Ala^{19}$,$Asp^{25}$,$Leu^{26}$,$Lys^{27,28}$]-VIP-cyclo ($Lys^{21} \rightarrow Asp^{25}$) [Ac—SEQ ID NO:44)—$NH_2$] | 0.097 |
| Ac—[p-F-$Phe^6$,$Glu^8$,$Lys^{12}$,$Nle^{17}$,$Ala^{19}$,$Asp^{25}$,$Leu^{26}$,$Lys^{27,28}$]-VIP cyclo ($Lys^{21} \rightarrow Asp^{25}$) [Ac—SEQ ID NO:45)—$NH_2$] | 0.026 |
| Ac—[1-$Nal^6$,$Glu^8$,$Lys^{12}$,$Nle^{17}$,$Ala^{19}$,$Asp^{25}$,$Leu^{26}$,$Lys^{27,28}$]-VIP cyclo ($Lys^{21} \rightarrow Asp^{25}$) [Ac—SEQ ID NO:46)—$NH_2$] | 0.036 |
| Ac—[$Glu^8$,p-$NH_2$-$Phe^{10}$,$Lys^{12}$,$Nle^{17}$,$Ala^{19}$,$Asp^{25}$,$Leu^{26}$,$Lys^{27,28}$]-VIP cyclo ($Lys^{21} \rightarrow Asp^{25}$) [Ac—SEQ ID NO:47)—$NH_2$] | 0.075 |
| Ac—[$Glu^8$,O—$CH_3$—$Tyr^{10}$,$Lys^{12}$,$Nle^{17}$,$Ala^{19}$,$Asp^{25}$,$Leu^{26}$,$Lys^{27,28}$]-VIP cyclo ($Lys^{21} \rightarrow Asp^{25}$) [Ac—SEQ ID NO:48)—$NH_2$] | 0.094 |
| Ac—[p-F-$Phe^6$,$Lys^{12}$,$Nle^{17}$,$Ala^{19}$,$Asp^{25}$,$Val^{26}$,$Thr^{28}$]-VIP cyclo ($Lys^{21} \rightarrow Asp^{25}$) [Ac—SEQ ID NO:49)—$NH_2$] | 0.26 |
| Ac—[$Ala^2$,$Glu^8$,$Lys^{12}$,$Nle^{17}$,$Ala^{19}$,$Asp^{25}$,$Leu^{26}$,$Lys^{27,28}$$Gly^{29,30}$,$Thr^{31}$]-VIP cyclo ($Lys^{21} \rightarrow Asp^{25}$) [Ac—SEQ ID NO:51)—$NH_2$] | 0.1 |
| Ac—[$Glu^8$,$Lys^{12}$,$Nle^{17}$,$Ala^{19}$,$Asp^{25}$,$Leu^{26}$,$Lys^{27,28}$$Gly^{29,30}$,$Thr^{31}$]-VIP cyclo ($Lys^{21} \rightarrow Asp^{25}$) [Ac—SEQ ID NO:52)—$NH_2$] | 0.1 |
| Ac—[$Ala^2$,$Glu^8$,$Lys^{12}$,$Nle^{17}$,$Ala^{19}$,$Asp^{25}$,$Leu^{26}$,$Lys^{27,28}$]-VIP cyclo ($Lys^{21} \rightarrow Asp^{25}$) [Ac—SEQ ID NO:53)—$NH_2$] | 0.14 |
| Ac—[p-$NH_2$-$Phe^{10}$,$Lys^{12}$,$Nle^{17}$,$Ala^{19}$,$Asp^{25}$,$Val^{26}$,$Thr^{28}$]-VIP cyclo ($Lys^{21} \rightarrow Asp^{25}$) [Ac—SEQ ID NO:54)—$NH_2$] | 0.35 |
| Ac—[$Lys^{12}$,$Nle^{17}$,$Ala^{19}$,m-$OCH_3$—$Tyr^{22}$,$Asp^{25}$,$Val^{26}$,$Thr^{28}$]-VIP cyclo ($Lys^{21} \rightarrow Asp^{25}$) [Ac—SEQ ID NO:55)—$NH_2$] | 0.14 |
| Ac—[$Lys^{12}$,$Nle^{17}$,$Ala^{19}$,m-F-L-$Tyr^{22}$,$Asp^{25}$,$Val^{26}$,$Thr^{28}$]-VIP cyclo ($Lys^{21} \rightarrow Asp^{25}$) [Ac—SEQ ID NO:56)—$NH_2$] | 7.2 |
| Ac—[$Glu^8$,$Lys^{12}$,$Nle^{17}$,$Ala^{19}$,m-$OCH_3$—$Tyr^{22}$,$Asp^{25}$,$Leu^{26}$,$Lys^{27,28}$]-VIP cyclo ($Lys^{21} \rightarrow Asp^{25}$) [Ac—SEQ ID NO:57)—$NH_2$] | 0.019 |

TABLE II-continued

Bronchodilator activity of VIP analogs in guinea pigs

| Compound | $ED_{50}$ (μg) |
|---|---|
| Ac—[Glu$^8$,Lys$^{12}$,Nle$^{17}$,Ala$^{19}$,m-F-L-Tyr$^{22}$,Asp$^{25}$,Leu$^{26}$,Lys$^{27,28}$]-VIP cyclo (Lys$^{21}$→Asp$^{25}$) [Ac—SEQ ID NO:58)—NH$_2$] | 0.03 |
| Ac—[Ala$^8$,Lys$^{12}$,Nle$^{17}$,Ala$^{19}$,Ala$^{24}$,Asp$^{25}$,Leu$^{26}$,Lys$^{27,28}$]-VIP cyclo (Lys$^{21}$→Asp$^{25}$) [Ac—SEQ ID NO:59)—NH$_2$] | 0.17 |
| Ac—[Glu$^8$,Lys$^{12}$,Ala$^{16,17,19}$,Asp$^{25}$,Leu$^{26}$,Lys$^{27,28}$]-VIP cyclo (Lys$^{21}$→Asp$^{25}$) [Ac—SEQ ID NO:60)—NH$_2$] | 0.17 |
| Ac—[Ala$^8$,Lys$^{12}$,Ala$^{16}$,Nle$^{17}$,Ala$^{19}$,Ala$^{24}$,Asp$^{25}$,Leu$^{26}$,Lys$^{27,28}$]-VIP cyclo (Lys$^{21}$→Asp$^{25}$) [Ac—SEQ ID NO:61)—NH$_2$] | 0.045 |
| Ac—[Ala$^8$,Lys$^{12}$,Ala$^{16,17,19}$,Ala$^{24}$,Asp$^{25}$,Leu$^{26}$,Lys$^{27,28}$]-VIP cyclo (Lys$^{21}$→Asp$^{25}$) [Ac—SEQ ID NO:62)—NH$_2$] | 0.24 |
| Ac—[Glu$^8$,Lys$^{12}$,Ala$^{16,17,19}$,Ala$^{24}$,Asp$^{25}$,Leu$^{26}$,Lys$^{27,28}$]-VIP cyclo (Lys$^{21}$→Asp$^{25}$) [Ac—SEQ ID NO:64)—NH$_2$] | 0.13 |
| Ac—[Glu$^8$,Lys$^{12}$,Nle$^{17}$,Ala$^{19}$,Asp$^{25}$,Val$^{26}$,Thr$^{28}$,Gly$^{29,30}$,Thr$^{31}$]-VIP cyclo (Lys$^{21}$→Asp$^{25}$) [Ac—(SEQ ID No:65)—NH$_2$] | 0.84 |
| Ac—[p-F-Phe$^6$-Glu$^8$,Lys$^{12}$,Nle$^{17}$,Asp$^{25}$,Val$^{26}$,Thr$^{28}$,Gly$^{29,30}$,Thr$^{31}$]-VIP cyclo (Lys$^{21}$→Asp$^{25}$) [Ac—(SEQ ID No:66)—NH$_2$] | 0.12 |
| Ac—[Ala$^2$—Glu$^8$,Lys$^{12}$,Nle$^{17}$,Asp$^{25}$,Leu$^{26}$,Lys$^{27,28}$,Gly$^{29,30}$,Thr$^{31}$]-VIP cyclo (Lys$^{21}$→Asp$^{25}$) [Ac—(SEQ ID No:67)—NH$_2$] | 0.077 |
| Ac—[Glu$^8$,Lys$^{12}$,Nle$^{17}$,Asp$^{25}$,Leu$^{26}$,Lys$^{27,28}$,Gly$^{29,30}$,Thr$^{31}$]-VIP cyclo (Lys$^{21}$→Asp$^{25}$) [Ac—(SEQ ID No:68)—NH$_2$] | 0.04 |
| Ac—[Lys$^{12}$,Nle$^{17}$,Ala$^{19}$,Asp$^{25}$,Leu$^{26}$,Lys$^{27,28}$,Ala$^{29-31}$]-VIP cyclo (Lys$^{21}$→Asp$^{25}$) [Ac—(SEQ ID No:69)—NH$_2$] | 0.04 |

We claim:

1. A cyclic vasoactive intestinal peptide analog of the formula:

X—R$_1$—R$_2$—Asp—Ala—Val—R$_6$—Thr—R$_8$—Asn—R$_{10}$—Thr—R$_{12}$—

Leu—Arg—Lys—R$_{16}$—R$_{17}$—Ala—R$_{19}$—Lys—Lys—R$_{22}$—

Leu—R$_{24}$—Asp—Leu—Lys—Lys—Y

[X—(SEQ ID NO:16)—Y]

wherein R$_1$ is His, N-CH$_3$-Ala; R$_2$ is Ser or Ala; R$_6$ is

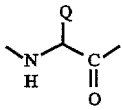

where Q is C$_{1-6}$ alkyl cyclohexyl, C$_{1-2}$ alkyl phenyl in which the phenyl ring is unsubstituted or substituted with one or more substitutents selected from the group consisting of OH, OCH$_3$, F, Cl, I, CH$_3$, CF$_3$, NO$_2$, NH$_2$, N(CH$_3$)$_2$, NHCOCH$_3$, NHCOC$_6$H$_5$, and C(CH$_3$)$_3$, or C$_{1-2}$ alkyl naphthyl in which the naphthyl rings are unsubstituted or substituted with one or more substituents selected from the group consisting of OH, OCH$_3$, F, Cl, I, CH$_3$, CF$_3$, NO$_2$, NH$_2$, N(CH$_3$)$_2$, NHCOCH$_3$, NHCOC$_6$H$_5$, and C(CH$_3$)$_3$; R$_8$ is Asp, Glu or Ala; R$_{10}$ is Tyr or R$_6$; R$_{12}$ is Arg, Leu, Orn or Lys; R$_{16}$ is Gln or Ala; R$_{17}$ is Met, Nle or Ala; R$_{19}$ is Val or Ala; R$_{22}$ is Tyr or R$_6$; R$_{24}$ is Asn or Ala; X is hydrogen or a hydrolyzable amino protecting group; Y is hydroxyl, a hydrolyzable carboxy protecting group, or R$_{29}$—R$_{30}$—R$_{31}$-Z; R$_{29}$ is Gly or Ala; R$_{30}$ is Gly or Ala; R$_{31}$ is Ala, Met, Cys(Acm), or Thr; Z is hydroxyl or a hydrolyzable carboxy protecting group; or pharmaceutically acceptable salts thereof.

2. The peptide of claim 1 wherein R$_{12}$ is Lys, R$_{17}$ is Ala, R$_{19}$ is Ala [X-(SEQ ID NO:17)-Y].

3. The peptide of claim 2 wherein said peptide is Ac-[Glu$^8$,Lys$^{12}$,Ala$^{16,17,19}$]-VIP cyclo (Lys$^{21}$→Asp$^{25}$) [Ac-(SEQ ID NO:60)-NH$_2$].

4. The peptide of claim 2 wherein said peptide is Ac-[Ala$^8$,Lys$^{12}$,Ala$^{16,17,19}$,Ala$^{24}$]-VIP cyclo (Lys$^{21}$→Asp$^{25}$) [Ac-(SEQ ID NO:62)-NH$_2$].

5. The peptide of claim 2 wherein said peptide is Ac-[Glu$^8$,Lys$^{12}$,Ala$^{16,17,19}$,Ala$^{24}$]-VIP cyclo (Lys$^{21}$→Asp$^{25}$) [Ac-(SEQ ID NO:64)-NH$_2$].

6. The peptide of claim 1 wherein R$_{12}$ is Lys, R$_{17}$ is Nle [X-(SEQ ID NO:18)-Y].

7. The peptide of claim 6 wherein said peptide is Ac-[Ala$^2$, Glu$^8$,Lys$^{12}$,Nle$^{17}$,Gly$^{29,30}$,Thr$^{31}$]-VIP cyclo (Lys$^{21}$→Asp$^{25}$) [Ac-(SEQ ID NO:67)-NH$_2$].

8. The peptide of claim 6 wherein said peptide is Ac-[Glu$^8$,Lys$^{12}$,Nle$^{17}$,Gly$^{29,30}$,Thr$^{31}$]-VIP cyclo (Lys$^{21}$→Asp$^{25}$) [Ac-(SEQ ID NO:68)-NH$_2$].

9. The peptide of claim 6 wherein R$_{12}$ is Lys, R$_{17}$ is Nle, R$_{19}$ is Ala [X-(SEQ ID NO:19)-Y].

10. The peptide of claim 9 wherein R$_{12}$ is Lys, R$_{16}$ is Gln, R$_{17}$ is Nle, R$_{19}$ is Ala [X-(SEQ ID NO:70)-Y].

11. The peptide is claim 10 wherein R$_2$ is Ser, R$_{12}$ is Lys, R$_{16}$ is Gln, R$_{17}$ is Nle, R$_{19}$ is Ala [X-(SEQ ID NO:71)-Y].

12. The peptide of claim 11 wherein said peptide is Ac-[Lys$^{12}$,Nle$^{17}$,Ala$^{19}$]-VIP cyclo (Lys$^{21}$→Asp$^{25}$) [Ac-(SEQ ID NO:38)-NH$_2$].

13. The peptide of claim 11 wherein said peptide is Ac-[N-Me-Ala$^1$,Lys$^{12}$,Nle$^{17}$,Ala$^{19}$]-VIP cyclo (Lys$^{21}$→Asp$^{25}$) [Ac-(SEQ ID NO:39)-NH$_2$].

14. The peptide of claim 11 wherein said peptide is Ac-[Glu$^8$,Lys$^{12}$,Nle$^{17}$,Ala$^{19}$]-VIP cyclo (Lys$^{21}$→Asp$^{25}$) [Ac-(SEQ ID NO:40)-NH$_2$].

15. The peptide of claim 11 wherein said peptide is Ac[Glu$^8$,Lys$^{12}$,Nle$^{17}$,Ala$^{19}$, Ala$^{29-31}$]-VIP cyclo [Ac-(SEQ ID NO:42)-NH$_2$].

16. The peptide of claim 11 wherein said peptide is Ac-[N-Me-Ala$^1$,Glu$^8$,Lys$^{12}$,Nle$^{17}$,Ala$^{19}$]-VIP cyclo (Lys$^{21}$→Asp$^{25}$) [Ac-(SEQ ID NO:44)-NH$_2$].

17. The peptide of claim 11 wherein said peptide is Ac-[p-F-Phe$^6$,Glu$^8$,Lys$^{12}$,Nle$^{17}$,Ala$^{19}$]-VIP cyclo (Lys$^{21}$→Asp$^{25}$) [Ac-(SEQ ID NO:45)-NH$_2$].

18. The peptide of claim 11 wherein said peptide is Ac-[1-Nal$^6$,Glu$^8$,Lys$^{12}$,Nle$^{17}$,Ala$^{19}$]-VIP cyclo (Lys$^{21}$→Asp$^{25}$) [Ac-(SEQ ID NO:46)-NH$_2$].

19. The peptide of claim 11 wherein said peptide is Ac-[Glu$^8$,p-NH$_2$-Phe$^{10}$,Lys$^{12}$,Nle$^{17}$,Ala$^{19}$]-VIP cyclo (Lys$^{21}$→Asp$^{25}$) [Ac-(SEQ ID NO:47)-NH$_2$].

20. The peptide of claim 11 wherein said peptide is Ac-[Glu$^8$,O-Me-Tyr$^{10}$,Lys$^{12}$,Nle$^{17}$,Ala$^{19}$]-VIP cyclo (Lys$^{21}$→Asp$^{25}$) [Ac-(SEQ ID NO:48)-NH$_2$].

21. The peptide of claim 11 wherein said peptide is Ac-[Glu$^8$,Lys$^{12}$,Nle$^{17}$,Ala$^{19}$,Gly$^{29,30}$,Thr$^{31}$]-VIP cyclo (Lys$^{21}$→Asp$^{25}$) [Ac-(SEQ ID NO:52)-NH$_2$].

22. The peptide of claim 11 wherein said peptide is Ac-[Glu$^8$,Lys$^{12}$,Nle$^{17}$,Ala$^{19}$,m-OCH$_3$-Tyr$^{22}$]-VIP cyclo (Lys$^{21}$→Asp$^{25}$) [Ac-(SEQ ID NO:57)-NH$_2$].

23. The peptide of claim 11 wherein said peptide is Ac-[Glu$^8$,Lys$^{12}$,Nle$^{17}$,Ala$^{19}$,m-F-L-Tyr$^{22}$]-VIP cyclo (Lys$^{21}$→Asp$^{25}$) [Ac-(SEQ ID NO:58)-NH$_2$].

24. The peptide of claim 11 wherein said peptide is Ac-[Ala$^8$,Lys$^{12}$,Nle$^{17}$,Ala$^{19}$,Ala$^{24}$]-VIP cyclo (Lys$^{21}$→Asp$^{25}$) [Ac-(SEQ ID NO:59)-NH$_2$].

25. The peptide of claim 11 wherein said peptide is Ac-[Lys$^{12}$,Nle$^{17}$,Ala$^{19}$,Ala$^{29-31}$]-VIP cyclo (Lys$^{21}$→Asp$^{25}$) [Ac-(SEQ ID NO:69)-NH$_2$].

26. The peptide of claim 10 wherein R$_2$ is Ala, R$_{12}$ is Lys, R$_{16}$ is Gln, R$_{17}$, is Nle, R$_{19}$ is Ala [X-SEQ ID NO:72)-Y].

27. The peptide of claim 26 wherein said peptide is Ac-[Ala$^2$,Glu$^8$,Lys$^{12}$,Nle$^{17}$,Ala$^{19}$,Ala$^{29-31}$]-VIP cyclo (Lys$^{21}$→Asp$^{25}$) [Ac-(SEQ ID NO:43)-NH$_2$].

28. The peptide of claim 26 wherein said peptide is Ac-[Ala$^2$,Glu$^8$,Lys$^{12}$,Nle$^{17}$,Ala$^{19}$,Gly$^{29,30}$,Thr$^{31}$]-VIP cyclo (Lys$^{21}$→Asp$^{25}$) [Ac-(SEQ ID NO:51)-NH$_2$].

29. The peptide of claim 26 wherein said peptide is Ac-[Ala$^2$,Glu$^8$,Lys$^{12}$,Nle$^{17}$,Ala$^{19}$]-VIP cyclo (Lys$^{21}$→Asp$^{25}$) [Ac-(SEQ ID NO:53)-NH$_2$].

30. The peptide of claim 9 wherein R$_{12}$ is Lys, R$_{16}$ is Ala, R$_{17}$ is Nle, R$_{19}$ is Ala [X-SEQ ID NO:73)-Y].

31. The peptide of claim 30 wherein said peptide is Ac-[Ala$^8$,Lys$^{12}$,Ala$^{16}$,Nle$^{17}$,Ala$^{19}$Ala$^{24}$]-VIP cyclo (Lys$^{21}$→Asp$^{25}$) [Ac-(SEQ ID NO:61)-NH$_2$].

32. The peptide of claim 30 wherein said peptide is Ac-[Glu$^8$,Lys$^{12}$,Ala$^{16}$,Nle$^{17}$,Ala$^{19}$]-VIP cyclo (Lys$^{21}$→Asp$^{25}$) [Ac-(SEQ ID NO:63)-NH$_2$].

\* \* \* \* \*